(12) United States Patent
Etter et al.

(10) Patent No.: US 11,571,436 B2
(45) Date of Patent: *Feb. 7, 2023

(54) ORAL FORMULATIONS OF CYTIDINE ANALOGS AND METHODS OF USE THEREOF

(71) Applicant: Celgene Corporation, Summit, NJ (US)

(72) Inventors: Jeffrey B. Etter, Boulder, CO (US); Mei Lai, Longmont, CO (US); Jay Thomas Backstrom, Leawood, KS (US)

(73) Assignee: CELGENE CORPORATION, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/533,033

(22) Filed: Nov. 22, 2021

(65) Prior Publication Data

US 2022/0079964 A1    Mar. 17, 2022

Related U.S. Application Data

(60) Continuation of application No. 16/833,410, filed on Mar. 27, 2020, now abandoned, which is a continuation of application No. 16/582,779, filed on Sep. 25, 2019, now Pat. No. 10,646,503, which is a continuation of application No. 16/244,014, filed on Jan. 9, 2019, now Pat. No. 10,463,683, which is a continuation of application No. 15/835,088, filed on Dec. 7, 2017, now Pat. No. 10,220,050, which is a division of application No. 14/788,606, filed on Jun. 30, 2015, now abandoned, which is a continuation of application No. 14/463,424, filed on Aug. 19, 2014, now abandoned, which is a continuation of application No. 12/466,213, filed on May 14, 2009, now Pat. No. 8,846,628.

(60) Provisional application No. 61/157,875, filed on Mar. 5, 2009, provisional application No. 61/201,145, filed on Dec. 5, 2008, provisional application No. 61/053,609, filed on May 15, 2008.

(51) Int. Cl.
| | |
|---|---|
| *A61K 31/706* | (2006.01) |
| *A61K 9/20* | (2006.01) |
| *A61K 9/28* | (2006.01) |
| *A61K 31/7068* | (2006.01) |
| *A61K 47/10* | (2017.01) |

(52) U.S. Cl.
CPC .......... *A61K 31/706* (2013.01); *A61K 9/2013* (2013.01); *A61K 9/2018* (2013.01); *A61K 9/2846* (2013.01); *A61K 9/2866* (2013.01); *A61K 9/2886* (2013.01); *A61K 31/7068* (2013.01); *A61K 47/10* (2013.01)

(58) Field of Classification Search
CPC .. A61K 31/706; A61K 9/2013; A61K 9/2018; A61K 9/2846; A61K 9/2866; A61K 9/2886; A61K 31/7068; A61K 47/10
See application file for complete search history.

(56) References Cited

U.S. PATENT DOCUMENTS

| | | |
|---|---|---|
| 3,350,388 A | 10/1967 | Sorm et al. |
| 3,817,980 A | 6/1974 | Vorbruggen et al. |
| 3,891,623 A | 6/1975 | Vorbruggen et al. |
| 4,082,911 A | 4/1978 | Vorbruggen |
| 4,209,613 A | 6/1980 | Vorbruggen |
| 5,700,640 A | 12/1997 | Voss et al. |
| 6,432,924 B1 | 8/2002 | Nyce |
| 6,566,395 B1 | 5/2003 | Moran |
| 6,642,206 B2 | 11/2003 | Ramasamy et al. |
| 6,794,400 B2 | 9/2004 | Cai et al. |
| 6,803,195 B1 | 10/2004 | Avivi et al. |
| 6,887,855 B2 | 5/2005 | Ionescu et al. |
| 6,890,547 B1 | 5/2005 | Takada et al. |
| 6,943,249 B2 | 9/2005 | Ionescu et al. |
| 7,038,038 B2 | 5/2006 | Ionescu et al. |
| 7,078,518 B2 | 7/2006 | Ionescu et al. |
| 7,189,740 B2 | 3/2007 | Zeldis |
| 7,192,781 B2 | 3/2007 | Luna et al. |
| 7,317,029 B2 | 1/2008 | Cai et al. |
| 7,642,247 B2 | 1/2010 | Daifuku et al. |
| 7,700,770 B2 | 4/2010 | Ionescu et al. |
| 7,759,481 B2 | 7/2010 | Gevenda et al. |
| 7,772,199 B2 | 8/2010 | Ionescu et al. |
| 7,858,774 B2 | 12/2010 | Ionescu et al. |
| 8,058,424 B2 | 11/2011 | Ionescu et al. |

(Continued)

FOREIGN PATENT DOCUMENTS

| | | |
|---|---|---|
| CZ | 114716 | 11/1964 |
| CZ | 116297 | 4/1965 |

(Continued)

OTHER PUBLICATIONS

Fallingbord. Intraluminal pH of the human gastrointestinal tract. Dan Med Bull. Jun. 1999;46(3):183-96. (Year: 1999).*

(Continued)

*Primary Examiner* — Robert A Wax
*Assistant Examiner* — Olga V. Tcherkasskaya
(74) *Attorney, Agent, or Firm* — Jones Day

(57) ABSTRACT

The present disclosure provides pharmaceutical compositions comprising cytidine analogs for oral administration, wherein the compositions release the cytidine analog substantially in the stomach. Also provided are methods of treating diseases and disorders using the oral formulations provided herein.

22 Claims, 29 Drawing Sheets

(56) References Cited

U.S. PATENT DOCUMENTS

| | | | |
|---|---|---|---|
| 8,211,862 | B2 | 7/2012 | Ionescu et al. |
| 8,846,628 | B2 | 9/2014 | Etter et al. |
| 9,125,884 | B2 | 9/2015 | MacBeth et al. |
| 10,220,050 | B2 | 3/2019 | Traverse et al. |
| 10,463,683 | B2 | 11/2019 | Traverse et al. |
| 10,646,503 | B2 | 5/2020 | Traverse et al. |
| 2001/0026807 | A1 | 10/2001 | Watts |
| 2002/0051820 | A1 | 5/2002 | Shell et al. |
| 2003/0039688 | A1 | 2/2003 | Shell et al. |
| 2003/0049311 | A1 | 3/2003 | McAllister et al. |
| 2003/0104053 | A1 | 6/2003 | Gusler et al. |
| 2003/0104062 | A1 | 6/2003 | Berner et al. |
| 2003/0220254 | A1 | 11/2003 | Khan et al. |
| 2004/0162263 | A1 | 8/2004 | Sands et al. |
| 2004/0186065 | A1 | 9/2004 | Ionescu et al. |
| 2005/0272675 | A1 | 12/2005 | Ionescu et al. |
| 2006/0063735 | A1 | 3/2006 | Redkar et al. |
| 2006/0069060 | A1 | 3/2006 | Redkar et al. |
| 2006/0074046 | A1 | 4/2006 | Redkar et al. |
| 2006/0128654 | A1 | 6/2006 | Tang et al. |
| 2006/0247189 | A1 | 11/2006 | Ionescu et al. |
| 2007/0190022 | A1 | 8/2007 | Bacopoulos et al. |
| 2007/0270374 | A1 | 11/2007 | Gallop |
| 2008/0057086 | A1 | 3/2008 | Etter |
| 2008/0182806 | A1 | 7/2008 | Pizzorno |
| 2009/0286752 | A1 | 11/2009 | Etter et al. |
| 2010/0035354 | A1 | 2/2010 | Bigatti et al. |
| 2010/0036112 | A1 | 2/2010 | Henschke et al. |
| 2010/0062992 | A1 | 3/2010 | Redkar et al. |
| 2010/0210833 | A1 | 8/2010 | Jungmann et al. |
| 2010/0292180 | A1 | 11/2010 | Ionescu et al. |
| 2010/0298253 | A1 | 11/2010 | Ionescu et al. |
| 2010/0311683 | A1 | 12/2010 | Beach et al. |
| 2011/0042247 | A1 | 2/2011 | Kocherlakota et al. |
| 2011/0092694 | A1 | 4/2011 | Ionescu et al. |
| 2011/0201800 | A1 | 8/2011 | Cherukupally et al. |
| 2011/0245485 | A1 | 10/2011 | De Ferra et al. |
| 2012/0029181 | A1 | 2/2012 | Ionescu et al. |
| 2012/0196823 | A1 | 8/2012 | Tutino et al. |
| 2013/0109644 | A1 | 5/2013 | MacBeth et al. |

FOREIGN PATENT DOCUMENTS

| | | |
|---|---|---|
| FR | 2123632 | 9/1972 |
| GB | 1227691 | 4/1971 |
| GB | 1227692 | 4/1971 |
| WO | WO 2004/082618 | 9/2004 |
| WO | WO 2004/082619 | 9/2004 |
| WO | WO 2004/082822 | 9/2004 |
| WO | WO 2006/034154 | 3/2006 |
| WO | WO 2006/089290 | 8/2006 |
| WO | WO 2006/094626 | 9/2006 |
| WO | WO 2008/028193 | 3/2008 |
| WO | WO 2008/088779 | 7/2008 |
| WO | WO 2009/016617 | 2/2009 |
| WO | WO 2009/052287 | 4/2009 |
| WO | WO 2009/139888 | 11/2009 |
| WO | WO 2010/059969 | 5/2010 |
| WO | WO 2011/014541 | 2/2011 |
| WO | WO 2012/135405 | 10/2012 |
| WO | WO 2013/022872 | 2/2013 |

OTHER PUBLICATIONS

Stomach acid test, in Medical Encyclopedia. National Library of Medicine. National Institute of Health. 1 page, //medlineplus.gov/ency/article/003883.htm (Year: 2022).*

Aparicio et al., Current Opinion in Investigational Drugs, 2002, 3(4), 627-33.

Argemi et al., Journal of Pharmaceutical and Biomedical Analysis, 2007, 44, 859-66.

Beisler et al., Journal of Medicinal Chemistry, 1977, 20(6), 806-12.

Bellet et al., Cancer Chemotherapy Reports, Part I, 1974, 58(2), 217-22.

Bellet et al., Medical and Pediatric Oncology, 1978, 4, 11-15.

Bhuyan et al., Cancer Research, 1972, 32, 398-407.

Bhuyan et al., Cancer Research, 1973, 33, 888-94.

Brock et al., New England Journal of Medicine, 2008, 358(11), 1118-28.

Chan et al., Journal of Pharmaceutical Sciences, 1979, 68(7), 807-12.

Christman et al., Oncogene, 2002, 21, 5483-95.

Cunningham et al., Cancer Chemotherapy Reports, Part I, 1974, 58(5), 677-81.

Curt et al., Cancer Research, 1985, 45, 3359-63.

Das et al., Molecular Cancer, 2006, 5(28), doi: 10.1186/1476-4598-5-28, available at http://www.molecular-cancer.com/content/5/1/28.

Dover et al., Blood, 1985, 66(3), 527-32.

Fenaux et al., The Lancet Oncology, 2009, 10(3), 223-32.

Garcia-Manero et al., Current Opinion in Oncology, 2008, 20, 705-10.

Gifford et al., Clinical Cancer Research, 2004, 10, 4420-26.

Israili et al., Cancer Research, 1976, 36, 1453-61.

Jordan et al., New England Journal of Medicine, 2006, 355(12), 1253-61.

Jubb, et al., Journal of Pathology, 2001, 195, 111-34.

Kornblith et al., Journal of Clinical Oncology, 2002, 20(10), 2441-52.

Li et al., Cancer Research, 1970, 30, 2770-75.

Lin et al., Journal of Pharmaceutical Sciences, 1981, 70(11), 1228-32.

Lomen et al., Cancer Chemotherapy Reports, Part I, 1975, 59(6), 1123-26.

Moertel et al., Cancer Chemotherapy Reports, Part I, 1972, 56(5), 649-52.

Mojaverian et al., Journal of Pharmacy and Pharmacology, 1984, 36, 728-33.

Neil et al., Cancer Chemotherapy Reports, Part I, 1975, 59(3), 459-65.

Notari et al., Journal of Pharmaceutical Sciences, 1975, 64(7), 1148-57.

Quagliana et al., Cancer Treatment Reports, 1977, 61(1), 51-54.

Sanderson et al., Nature News, Mar. 16, 2009, available at http://www.nature.com/news/2009/090316/full/458269a.html.

Shnider et al., Journal of Clinical Pharmacology, 1976, 205-12.

Silverman et al., Journal of Clinical Oncology, 2002, 20(10), 2429-40.

Silverman et al., Journal of Clinical Oncology, 2006, 24(24), 3895-3903.

Sktkne et al., "A Phase I, Open-Label, Dose-Escalation Study to Evaluate the Safety, Pharmacokinetics, and Pharmacodynamics of Oral Azacitidine in Subjects with Myelodysplastic Syndromes (MDS) or Acute Myelogenous Leukemia (AML)," Journal of Clinical Oncology (May 20, 2008 Supplement), 2008 ASCO Annual Meeting Proceedings (Meeting Date: May 30-Jun. 3, 2008), Part 1, 2008, 26(15S), poster # 7091.

Srinivasan et al., American Journal of Clinical Oncology, 1982, 5, 411-15.

Stoltz et al., "Development of an Oral Dosage Form of Azacitidine: Overcoming Challenges in Chemistry, Formulation, and Bioavailability," Blood, 48th ASH Annual Meeting (Meeting Date: Dec. 9-12, 2006), 2006, 108, poster # 4850.

Tan et al., "Clinical Trial of 5-Azacytidine (5-azaCR)," American Association for Cancer Research, 64th Annual Meeting, Abstract # 385, Apr. 11-13, 1973.

Troetel, et al., Cancer Chemotherapy Reports, Part I, 1972, 56(3), 405-11.

Velez-Garcia et al., Cancer Treatment Reports, 1977, 61(9), 1675-77.

Ward et al., "An Oral Dosage Formulation of Azacitidine: A Pilot Pharmacokinetic Study," Journal of Clinical Oncology (Jun. 20, 2007 Supplement), 2007 ASCO Annual Meeting Proceedings (Meeting Date: Jun. 1-5, 2007), Part I, 2007, 25(18S), poster # 7084.

International Search Report, for PCT/US2009/002999, filed May 14, 2009.

(56) References Cited

OTHER PUBLICATIONS

Beers et al. (eds.), Chapter 142, Section 11, in The Merck Manual of Diagnosis and Therapy, 18th Edition, pp. 1114-1116 (2006).
Beisler et al., "Chemistry of Antitumor Triazine Nucleosides. An Improved Synthesis of Dihydro-5-Azacytidine," J. Carbohydrates Nucleosides Nucleotides, 4(5): 281-99 (1977).
Beisler, "Isolation, Characterization, and Properties of a Labile Hydrolysis Product of the Antitumor Nucleoside, 5-Azacytidine," J. Med. Chem., 21(2): 204-08 (1978).
Bergy et al., "Microbiological Production of 5-Azacytidine II. Isolation and Chemical Structure," Antimicrobial Agents and Chemotherapy, 625-30 (1966).
Chen et al., "Highly Efficient Regioselective Synthesis of 5'-O-lauroyl-5-azacytidine Catalyzed by Candida Antarctica Lipase B," Appl. Biochem. Biotechnol., 151: 21-28 (2008).
Dintaman et al., "Inhibition of P-Glycoprotein by D-α-Tocopheryl Polyethylene Glycol 1000 Succinate (TPGS)," Pharmaceutical Research, 16(10): 1550-1556 (1999).
Garcia-Manero et al., "A Pilot Pharmacokinetic Study of Oral Azacitidine," Leukemia, 22: 1680-84 (2008).
Garcia-Manero et al., "Phase 1 Study of Oral Azacitidine in Myelodysplastic Syndromes, Chronic Myelomonocytic Leukemia, and Acute Myeloid Leukemia," J. Clin. Oncol., 29(18): 2521-27 (2011).
Gaubert et al., "Unnatural Enantiomers of 5-Azacytidine Analogues: Synthesis and Enzymatic Properties," Nucleosides, Nucleotides & Nucleic Acids, 20(4-7): 837-40 (2001).
Gut et al., "Aza Analogs of Pyrimidine and Purine Bases of Nucleic Acids," in Advances in Heterocyclic Chemistry, vol. 1, Katritzky ed., pp. 189-251 (1963).
Hanka et al., "Microbiological Production of 5-Azacytidine I. Production and Biological Activity," Antimicrobial Agents and Chemotherapy, 619-24 (1966).
Kritz et al., "Pilot Study of 5-Azacytidine (5-AZA) and Carboplatin (CBDCA) in Patients with Relapsed/Refractory Leukemia," American Journal of Hematology, 51(2): 117-21 (1996).
Niedballa et al., "A General Synthesis of N-Glycosides. V. Synthesis of 5-Azacytidines," J. Org. Chem., 39(25): 3672-74 (1974).
Notice of Allowance dated Sep. 20, 2011 in U.S. Appl. No. 12/729,116.
O'Neil et al. (eds.), The Merck Index, 13th Edition, p. 154-55 (2001).
O'Neil et al. (eds.), The Merck Index, 14th Edition, p. 150 (2006).
Office Action dated Sep. 23, 2011 in U.S. Appl. No. 12/787,214.
Office Action dated Nov. 28, 2011 in U.S. Appl. No. 12/729,116.
Piskala et al., "Nucleic Acids Components and Their Analogues. LI. Synthesis of 1-Glycosyl Derivatives of 5-Azauracil and 5-Azacytosine," Collect. Czech. Chem. Commun., 29: 2060-76 (1964).
Piskala et al., "Direct Synthesis of 5-Azapyrimidine Ribonucleosides," Nucleic Acids Research, Special Pub. No. 1: s17-20 (1975).
Piskala et al., "Direct Synthesis of a 5-Azapyrimidine Ribonucleoside by the Tri-methylsilyl Procedure," Nucleic Acid Chem., 1: 435-41 (1978).
Vogler et al., "5-Azacytidine (NSC 102816): A New Drug for the Treatment of Myeloblastic Leukemia," Blood, 48(3): 331-37 (1976).
Vorbruggen et al., "Nucleoside Synthesis with Trimethylsilyl Triflate and Perchlorate as Catalysts," Chem. Ber., 114: 1234-55 (1981).
Vorbruggen et al., "A New Simplified Nucleoside Synthesis," Chem. Ber., 114: 1279-86 (1981).
Vorbruggen et al., in Organic Reactions, vol. 55, 100 (L.A. Paquette ed., John Wiley & Sons, New York, 2000).
Winkley et al., "Direct Glycosylation of 1,3,5-Triazinones. A New Approach to the Synthesis of the Nucleoside Antibiotic 5-Azacytidine (4-Amino-1-β-D-ribofiiranosyl-1,3,5-triazin-2-one) and Related Derivatives," J. Org. Chem., 35(2): 491-95 (1970).
Wittenburg et al., "A New Synthesis of Nucleosides," Zeitschrift fur Chemie, 4: 303-04 (1964) (with English translation).
Zaitseva et al., "Convergent Syntheses and Cytostatic Properties of 2-Chloro-2'-Deoxy-2'-Fluoroadenosine and its N7-Isomer," Bioorg. & Med. Chem. Lett., 5(24): 2999-3002 (1995).

Ziemba et al., "Development of Oral Demethylating Agents for the Treatment of Myelodysplastic Syndromes," American Association of Cancer Research, 100th Annual Meeting, Apr. 18-22, Abstract #3369 (2009).
Notice of Allowability in U.S. Appl. No. 12/729,116, dated May 4, 2012.
Anonymous, "A Phase I/II Clinical Trial of Vidaza with Abraxane in the Treatment of Patients with Advanced or Metastatic Solid Tumors and Breast Cancer," ClinicalTrials.gov archive, pp. 1-3, retrieved from the Internet: http://clinicaltrials.gov/archive/NCT00748553/2011_08_05, on Jan. 31, 2013.
Anonymous, "Oral Azacitidine as a Single Agent and in Combination with Carboplatin or Abraxane in Subjects with Relapsed or Refractory Solid Tumors," ClinicalTrials.gov archive, pp. 1-4, retrieved from the Internet: http://clinicaltrials.gov/archive/NCT01478685/2011_11_22, on Jan. 31, 2013.
Bast et al., "A Phase IIa Study of a Sequential Regimen Using Azacitidine to Reverse Platinum Resistance to Carboplatin in Patients with Platinum Resistant or Refractory Epithelial Ovarian Cancer," Journal of Clinical Oncology, 26, Abstract 3500, (2008).
Cowan et al., "Will DNA Methylation Inhibitors Work in Solid Tumors? A Review of the Clinical Experience with Azacitidine and Decitabine in Solid Tumors," Epigenomics, Future Medicine Ltd, United Kingdom, 2(1):71-86 (2010).
Glaser, "HDAC Inhibitors: Clinical Update and Mechanism-Based Potential," Biochem. Pharm., 74:659-71 (2007).
Howell et al., "Demethylating Agents in the Treatment of Cancer," Pharmaceuticals, 3(7):2022-44 (2010).
Juergens et al., "Interim Analysis of a Phase II Trial of 5-Azacitidine (5AC) and Entinostat (SNDX-275) in Relapsed Advanced Lung Cancer (NSCLC)," Journal of Clinical Oncology, 27(15S):8055 (2009).
Mompabler, "Epigenetic Therapy of Cancer with 5-Aza-2'-Deoxycitidine (Decitabine)," Seminars in Oncology, 32(5):443-51 (2005).
Stathis et al., "Phase I Study of Decitabine in Combination with Vorinostat in Patients with Advanced Solid Tumors and Non-Hodgkin's Lymphomas," Clinical Cancer Research, 17(6):1582-90 (2011).
Vidaza™ Label (azacitidine for injectable suspension), Version: May 18, 2004.
Vidaza™ (azacitidine for injection) Prescribing Information, dated Jan. 2012.
Garcia-Manero et al., "Safety and efficacy of oral azacitidine (CC-486) administered in extended treatment schedules to patients with lower-risk myelodysplastic syndromes," Blood, 120:Abstract 424 (2012).
Vidaza™ (azacitidine for injection) Prescribing Information, dated Dec. 2012.
Cerny et al., "Preparation of Some Tritium Labelled Nucleosides by Catalyzed Exchange in Solution," Radiochem. Radioanal. Letters, 35(4-5), 211-213 (1978). (Year: 1978).
ONUREG (azacitidine) FDA approval label, revised Sep. 2020.
Aulton et al., Pharmaceutics The Science of Dosage Form Design, $2^{nd}$ ed., 2002, pp. 222-223.
Kilor et al., "Development and Characterization of Enteric-Coated Immediate-Release Pellets of Aceclofenac by Extrusion/Spheronization Technique Using κ-Carrageenan as a Pelletizing Agent", AAPS PharmSciTech, 11(1):336-343 (2010).
Raj et al., "Azacytidine in the treatment of myelodysplastic syndromes", Therapeutics and Clinical Risk Management 2006:2(4) 377-388.
Press Release: Pharmion's Oral Azacitidine Granted Fast Track Status for Myelodysplastic Syndromes, Aug. 29, 2007, retrieved from the Internet: https://www.fiercebiotech.com/biotech/press-release-pharmion-s-oral-azacitidine-granted-fast-track-status-for-myelodysplastic [downloaded Nov. 16, 2021].
Opposition against European Patent No. EP2299984B1, filed Aug. 27, 2019, 7 pages.
Opposition against European Patent No. EP2299984B1, filed Aug. 28, 2019, 14 pages.

(56) References Cited

OTHER PUBLICATIONS

Patentee's response to oppositions against European Patent No. EP2299984B1, filed Jan. 17, 2020, including auxiliary requests 1-5, 30 pages.
Summons to attend oral proceedings regarding oppositions against European Patent No. EP2299984B1, issued Jul. 21, 2020, 15 pages.
Written submission by patentee before oral proceedings against European Patent No. EP2299984B1, filed Aug. 6, 2021, including auxiliary requests 1-3, 47 pages.
Grounds for decision revoking European Patent No. EP2299984B1, issued Dec. 3, 2021, 27 pages.
Opposition against European Patent No. EP2695609B1, filed Aug. 30, 2020, 24 pages.
Opposition against European Patent No. EP2695609B1, filed Sep. 4, 2020, 8 pages.
Opposition against European Patent No. EP2695609B1, filed Sep. 10, 2020, 22 pages.
Opposition against European Patent No. EP2695609B1, filed Sep. 11, 2020, 29 pages.
Patentee's response to oppositions against European Patent No. EP2695609B1, filed Apr. 8, 2021, including auxiliary requests 1-5, 57 pages.
Invalidation Request against Chinese Patent No. ZL 200980127929. 8, filed Mar. 29, 2021, 35 pages (English translation included).
Invalidation Request against Chinese Patent No. ZL 201310363158. 0, filed Mar. 30, 2021, 39 pages (English translation included).
Patentee's response to Invalidation Request against Chinese Patent No. ZL 200980127929.8, filed Jun. 7, 2021, 8 pages (English translation included).
Patentee's response to Invalidation Request against Chinese Patent No. ZL 201310363158.0, filed May 31, 21 pages (English translation included).
Patentee's post-hearing brief to Invalidation Request against Chinese Patent No. ZL 200980127929.8, filed Aug. 13, 2021, 17 pages (English translation included).
Patentee's post-hearing brief to Invalidation Request against Chinese Patent No. ZL 201310363158.0, filed Aug. 13, 2021, 29 pages (English translation included).
Invalidation Decision against Chinese Patent No. ZL 200980127929. 8, issued Nov. 29, 2021 (English translation included).
Invalidation Decision against Chinese Patent No. ZL 201310363158. 0, issued Nov. 29, 2021 (English translation included).
Patentee's administrative complaint against Invalidation Decision against Chinese Patent No. ZL 200980127929.8, filed Feb. 28, 2022 (English translation included).
Patentee's administrative complaint against Invalidation Decision against Chinese Patent No. ZL 201310363158.0, filed Feb. 28, 2022 (English translation included).
EPO Form 2906 dated Jun. 18, 2018 detailing the rejection of the MR and ARI at oral proceedings of European Patent Application No. 09746975.3.
Cogle et al., "Oral Azacitidine (CC-486) for the Treatment of Myelodysplastic Syndromes and Acute Myeloid Leukemia", The Oncologist 2015, 20:1-9.
BMS Press Release, "Bristol-Myers Squibb Presents Overall Survival and Safety Data from Pivotal CC-486 Study QUAZAR AML-001", Dec. 10, 2019.
Shargel et al., "Applied Biopharmaceutics & Pharmacokinetics", Fifth Edition, 2005, pp. 515.
ICH Topic Q 6 A: Specification: Test Procedures and Acceptance Criteria for New Drug Substances and New Drug Products: Chemical Substances—Glossary.
Aulton, "Aulton's Pharmaceutics: The Design and Manufacture of Medicines", 3rd Edition, 2007, pp. 454-455.
Applicant's written submission dated Apr. 10, 2018 in preparation for oral proceedings before the Examining Division in European Patent Application No. 09746975.3.
Rowe et al., "Handbook of Pharmaceutical Excipients", 5th Edition, 2006, pp. 554-555.
Lachman et al., "The Theory and Practice of Industrial Pharmacy", 3rd Edition, 1986, pp. 331-332.
Highlights of Prescribing Information for Vidaza™ (azacitidine for injection), dated Aug. 2008.
National Cancer Institute, "Bioassay of 5-Azacytidine for Possible Carcinogenicity", Carcinogenesis Technical Report Series No. 42, 1978, pp. 3-4.
"IARC monographs on the evaluation of carcinogenic risks to humans", Pharmaceutical Drugs vol. 50, 1990, pp. 47-48.
Chemical Stability of Pharmaceuticals: A Handbook for Pharmacists, 2nd Edition, Nov. 1986, pp. 239.
Stresemann, C. and Lyko F., "Modes of action of the DNA methyltransferase inhibitors azacytidine and decitabine", Int. J. Cancer, 2008, 123, 8-13.
Kissinger, L.D. and Stemm, N.L., "Determination of the Antileukemia Agents Cytarabine and Azacitidine and Their Respective Degradation Products by High-Performance Liquid Chromatography", J. Chromatogr. A, 1986, 353, 309-318.
Chiak, A. and Sorm, F., "Biochemical Effects and Metabolic Transformations of 5-Azacytidine in *Escherichia coli*", Collect. Czech. Chem. Commun., 965, 30, 2091-2102.
Cheung et al., "Stability of azacitidine in infusion fluids", Am. J. Hosp. Pharm., 1984, 41, 1156-1159.
Pithova et al., "Nucleic Acids Components and Their Analogues. LXVL. Hydrolysis of 5-Azacytidine and Its Connection with Biological Activity", Collect. Czech. Chem. Commun. 1965, 30, 2801-2811.
Chabner et al., "Deamination of 5-azacytidine by a human leukemia cell cytidine deaminase", Biochem. Pharmacol., 1973, 22, 2763-2765.
Kaminskas et al., "FDA Drug Approval Summary: Azacitidine (5-azacytidine, Vidaza™) for Injectable Suspension", Oncologist, 2005, 10, 176-182.
Mund et al., "Reactivation of Epigenetically Silenced Genes by DNA Methyltransferase Inhibitors: Basic Concepts and Clinical Applications", Epigenetics, 2006, 1(1), 7-13.
Wei et al., "Oral Azacitidine Maintenance Therapy for Acute Myeloid Leukemia in First Remission", N. Engl. J. Med., 2020, 383, 2526-2537.
Summary of Product Characteristics for Vidaza® (2008).
Notice of Opposition filed by Teva Pharmaceutical Industries Ltd on Apr. 5, 2017 against European Patent No. EP1610784B1.
Aulton, "Aulton's Pharmaceutics: The Design and Manufacture of Medicines", 3rd Edition, 2007, Chapter 1, pp. 5-6 and 9.
Gibson, "Pharmaceutical Preformulation and Formulation", 2005, p. 332.
European Commission Decision granting marketing authorisation in EU for Onureg, dated Jun. 17, 2021.
BMS Press Release, "Bristol Myers Squibb Receives European Commission Approval for Onureg (azacitidine tablets) as Frontline Oral Maintenance Therapy for Adults with Acute Myeloid Leukemia", dated Jun. 18, 2021.
Weiss et al., "Phase I Study of 5-Azacytidine (NSC-102816)", Cancer Chemotherapy Reports, 1972, 56(3), 413-419.
Weiss et al., "Phase II Study of 5-Azacytidine in Solid Tumors", Cancer Treatment Reports, 1977, 61(1), 55-58.
Declaration of Charles L. Beach, submitted on Feb. 27, 2014 in U.S. Appl. No. 12/466,213, 45 pages.
Re-examination Decision of Chinese Patent Application No. 200980127929.8, dated Oct. 16, 2014, 6 pages (English translation included).
Wang et al., Medicine Knowledge (Medicine Volume), $1^{st}$ ed., 2007, pp. 179-186 (English translation included).
Cancellation Brief against Taiwanese Patent No. 1522103, filed May 2, 2022, in Chinese with English translation (93 pages).
Remarks for response submitted to the Taiwanese Intellectual Property Office on Jan. 24, 2014 in Taiwanese Patent Application No. 098116326 (now Taiwanese Patent No. TW 1522103 B), in Chinese with English translation (7 pages).
Remarks for response submitted to the Taiwanese Intellectual Property Office on Oct. 7, 2015 in Taiwanese Patent Application No. 098116326 (now Taiwanese Patent No. TW 1522103 B), in Chinese with English translation (18 pages).

(56) References Cited

OTHER PUBLICATIONS

EPO Appeal No. T0145/22-3.3.07, Appellant/Proprietor's Statement of Grounds of Appeal against Decision to Revoke European Patent No. EP2299984B1, filed Apr. 13, 2022, including Auxiliary Requests 1-7 (clean and marked-up versions) and Annexes 1-2 (75 pages).
Rowland et al., 1995, "Clinical Pharmacokinetics Concepts and Applications," 3rd Ed., pp. 11-12, 128-129 and 131-132 (11 pages).
Becker et al., 2006, "Aspirin," in Fibrinolytic and Antithrombotic Therapy: Theory, Practice, and Management, Oxford University Press (2 pages).
Thomson et al., 1997, "Influence of food on the bioavailability of an enteric-coated tablet formulation of omeprazole 20 mg under repeated dose conditions," Can. J. Gastroenterol., 11(8):663-667.
Vanderhoff et al., 2002, "Proton pump inhibitors: an update," Am. Fam. Physician, 66(2):273-280.
Summons to attend oral proceedings pursuant to Rule 115(1) EPC regarding oppositions against European Patent No. EP2695609B1 dated Feb. 4, 2022 (26 pages).
Notice of Opposition filed by Lotus Pharmaceutical Co., Ltd. (O1) on Apr. 29, 2022 against European Patent No. EP3692983B1 (14 pages).
Notice of Opposition filed by Sandoz AG (O2) on May 9, 2022 against European Patent No. EP3692983B1 (20 pages).
Notice of Opposition filed by Teva Pharmaceutical Industries Limited (O3) on May 10, 2022 against European Patent No. EP3692983B1 (7 pages).
Notice of Opposition filed by Hoffmann Eitie (O4) on May 10, 2022 against European Patent No. EP3692983B1 (15 pages).
Notice of Opposition filed by STADA Arzneimittel AG (O5) on May 11, 2022 against European Patent No. EP3692983B1, in German with English translation (42 pages).
Notice of Opposition filed by Generics [UK] Limited (O6) on May 11, 2022 against European Patent No. EP3692983B1 (14 pages).
Ziemba et al., 2011, "Development of an oral form of azacytidine: 2'3'5'triacetyl-5-azacytidine," Chemother, Res. Pract., 965826 (9 pages).
Ritschel et al., 2002, "The Tablet—Manual of development, manufacture and quality assurance," 2nd completely revised and updated edition, ECV—Editio Cantor Verlag Aulendorf, p. 30, in German with English translation of cover page and p. 30 (7 pages).
Perrie et al., 2010, "Chapter 1—Controlling drug delivery of FASTtrack: Pharmaceutics—Drug Delivery and Targeting," Pharmaceutical Press (35 pages).

Leone et al., 2008, "Epigenetic treatment of myelodysplastic syndromes and acute myeloid leukemias," Curr. Med. Chem., 15(13):1274-1287.
Evidence that Leone et al., 2008, "Epigenetic treatment of myelodysplastic syndromes and acute myeloid leukemias," Curr. Med. Chem., 15(13): 1274-1287 was published in Jun. 2008 (28 pages).
Kurkjian et al., 2008, "DNA methylation: its role in cancer development and therapy," Curr. Probl. Cancer, 32(5):187-235.
Evidence that Kurkjian et al., 2008, "DNA methylation: its role in cancer development and therapy," Curr. Probl. Cancer, 32(5):187-235 was published in Oct. 2008 (1 page).
Hirayama et al., 1999, "Cyclodextrin-based controlled drug release system," Adv. Drug Deliv. Rev., 36(1):125-141.
ClinicalTrials.gov archive, "History of Changes for Study: NCT00528983: Safety, Pharmacokinetics of Oral Azacitidine in Subjects With MDS and AML," submitted Sep. 12, 2007 (v1), available from internet: https://clinicaltrials.gov/ct2/history/NCT00528983?A=1&B=1&C=merged#StudyPageTop (8 pages).
ClinicalTrials.gov archive, "History of Changes for Study: NCT00528983: Safety, Pharmacokinetics of Oral Azacitidine in Subjects With Myelodysplastic Syndromes and Acute Myelogenous Leukemia," submitted Apr. 2, 2008 (v5), available from internet: https://clinicaltrials.gov/ct2/history/NCT00528983?A=5&B=5&C=merged#StudyPageTop (10 pages).
ClinicalTrials.gov archive, "History of Changes for Study: NCT00528983: Safety, Pharmacokinetics of Oral Azacitidine in Subjects With Myelodysplastic Syndromes and Acute Myelogenous Leukemia," submitted Sep. 22, 2008 (v9), available from internet: https://clinicaltrials.gov/ct2/history/NCT00528983?A=9&B=9&C=merged#StudyPageTop (10 pages).
Clinicaltrials.gov, "NCT00528983: Safety, Pharmacokinetics, and Pharmacodynamics of Oral Azacitidine in Subjects With Myelodysplastic Syndromes, Chronic Myelomonocytic Leukemia and Acute Myelogenous Leukemia," first posted Sep. 14, 2007, last updated posted Nov. 8, 2019, available from internet: https://clinicaltrials.gov/ct2/show/NCT00528983 (7 pages).
Supplemental Cancellation Brief against Taiwanese Patent No. I522103, filed Jul. 26, 2022, in Chinese with English translation (43 pages).
Gore et al., 2006, "Combined DNA Methyltransferase and Histone Deacetylase Inhibition in the Treatment of Myeloid Neoplasms," Cancer Res., 66(12):6361-9.
Morrison et al., 1977, "Plasma Prednisolone Levels from Enteric and Non-Enteric Coated Tablets Estimated by an Original Technique," Br. J. Pharmac., 4, 597-603.

* cited by examiner

ORAL FORMULATIONS OF CYTIDINE ANALOGS AND METHODS OF USE THEREOF

I. CROSS-REFERENCE TO RELATED APPLICATIONS

This application is a continuation of U.S. patent application Ser. No. 16/833,410, filed Mar. 27, 2020, which is a continuation of U.S. patent application Ser. No. 16/582,779, filed Sep. 25, 2019, now issued as U.S. Pat. No. 10,646,503, which is a continuation of U.S. patent application Ser. No. 16/244,014, filed Jan. 9, 2019, now issued as U.S. Pat. No. 10,463,683, which is a continuation of U.S. patent application Ser. No. 15/835,088, filed Dec. 7, 2017, now issued as U.S. Pat. No. 10,220,050, which is a divisional of U.S. patent application Ser. No. 14/788,606, filed Jun. 30, 2015, now abandoned, which is a continuation of U.S. patent application Ser. No. 14/463,424, filed Aug. 19, 2014, now abandoned, which is a continuation of U.S. patent application Ser. No. 12/466,213, filed May 14, 2009, now issued as U.S. Pat. No. 8,846,628, which claims priority to U.S. Provisional Patent Application Nos. 61/053,609, filed May 15, 2008; 61/201,145, filed Dec. 5, 2008; and 61/157,875, filed Mar. 5, 2009, the contents of each of which are incorporated by reference herein in their entireties.

II. FIELD

Provided herein are pharmaceutical formulations comprising cytidine analogs, or their salts, solvates, hydrates, precursors, and/or derivatives thereof, for oral administration in subjects. Also provided are methods for making the formulations and methods for using the formulations to treat diseases and disorders including cancer, disorders related to abnormal cell proliferation, hematologic disorders, and immune disorders, among others.

III. BACKGROUND

Cancer is a major worldwide public health problem; in the United States alone, approximately 570,000 cancer-related deaths were expected in 2005. See, e.g., Jemal et al., *CA Cancer J. Clin.* 55(1):10-30 (2005). Many types of cancer have been described in the medical literature. Examples include cancer of the blood, bone, lung (e.g., non-small-cell lung cancer and small-cell lung cancer), colon, breast, prostate, ovary, brain, and intestine. The incidence of cancer continues to climb as the general population ages and as new forms of cancer develop. A continuing need exists for effective therapies to treat subjects with cancer.

Myelodysplastic syndromes (MDS) refers to a diverse group of hematopoietic stem cell disorders. MDS affects approximately 40,000-50,000 people in the U.S. and 75,000-85,000 subjects in Europe. MDS may be characterized by a cellular marrow with impaired morphology and maturation (dysmyelopoiesis), peripheral blood cytopenias, and a variable risk of progression to acute leukemia, resulting from ineffective blood cell production. See, e.g., *The Merck Manual* 953 (17th ed. 1999); List et al., *J. Clin. Oncol.* 8:1424 (1990).

MDS are grouped together because of the presence of dysplastic changes in one or more of the hematopoietic lineages including dysplastic changes in the myeloid, erythroid, and megakaryocytic series. These changes result in cytopenias in one or more of the three lineages. Patients afflicted with MDS may develop complications related to anemia, neutropenia (infections), and/or thrombocytopenia (bleeding). From about 10% to about 70% of patients with MDS may develop acute leukemia. In the early stages of MDS, the main cause of cytopenias is increased programmed cell death (apoptosis). As the disease progresses and converts into leukemia, a proliferation of leukemic cells overwhelms the healthy marrow. The disease course differs, with some cases behaving as an indolent disease and others behaving aggressively with a very short clinical course that converts into an acute form of leukemia. The majority of people with higher risk MDS eventually experience bone marrow failure. Up to 50% of MDS patients succumb to complications, such as infection or bleeding, before progressing to AML.

Primary and secondary MDS are defined by taking into account patients' prior history: previous treatments with chemotherapy, radiotherapy or professional exposure to toxic substances are factors delineating secondary MDS (sMDS) from primary MDS. Cytogenetically, one difference between the two groups is the complexity of abnormal karyotypes; single chromosome aberrations are typical for primary MDS, while multiple changes are more frequently seen in secondary disorders. Some drugs may have specific targets such as hydroxurea for 17p and topoisomerases inhibitors for 11q23 and 21q22. The genetic changes in the malignant cells of MDS result mainly in the loss of genetic material, including probable tumor suppressor genes.

An international group of hematologists, the French-American-British (FAB) Cooperative Group, classified MDS into five subgroups, differentiating them from acute myeloid leukemia. See, e.g., *The Merck Manual* 954 (17th ed. 1999); Bennett J. M., et al., *Ann. Intern. Med.,* 103(4): 620-5 (1985); and Besa E. C., *Med. Clin. North Am.* 76(3): 599-617 (1992). An underlying trilineage dysplastic change in the bone marrow cells of the patients is found in all subtypes. Information is available regarding the pathobiology of MDS, certain MDS classification systems, and particular methods of treating and managing MDS. See, e.g., U.S. Pat. No. 7,189,740 (issued Mar. 13, 2007), which is incorporated by reference herein in its entirety.

Nucleoside analogs have been used clinically for the treatment of viral infections and cancer. Most nucleoside analogs are classified as anti-metabolites. After they enter the cell, nucleoside analogs are successively phosphorylated to nucleoside 5'-mono-phosphates, di-phosphates, and tri-phosphates.

5-Azacytidine (National Service Center designation NSC-102816; CAS Registry Number 320-67-2), also known as azacitidine, AZA, or 4-amino-1-β-D-ribofuranosyl-1,3,5-triazin-2(1H)-one, is currently marketed as the drug product VIDAZA®. 5-Azacytidine is a nucleoside analog, more specifically a cytidine analog. 5-Azacytidine is an antagonist of its related natural nucleoside, cytidine. 5-Azacytidine and 5-aza-2'-deoxycytidine (also known as decitabine, an analog of deoxycytidine) are also antagonists of deoxycytidine. A structural difference between these cytidine analogs and their related natural nucleoside is the presence of a nitrogen at position 5 of the cytosine ring in place of a carbon. 5-Azacytidine may be defined as having the molecular formula $C_8H_{12}N_4O_5$, a molecular weight of 244.21 grams per mole, and the following structure:

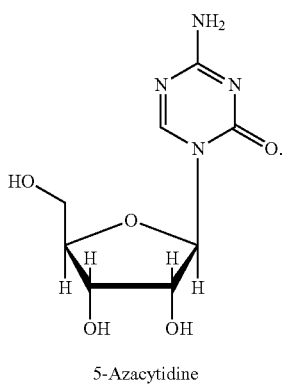

5-Azacytidine

Other members of the class of cytidine analogs include, for example: 1-β-D-arabinofuranosylcytosine (Cytarabine or ara-C); 5-aza-2'-deoxycytidine (Decitabine or 5-aza-CdR); pseudoisocytidine (psi ICR); 5-fluoro-2'-deoxycytidine (FCdR); 2'-deoxy-2',2'-difluorocytidine (Gemcitabine); 5-aza-2'-deoxy-2',2'-difluorocytidine; 5-aza-2'-deoxy-2'-fluorocytidine; 1-β-D-ribofuranosyl-2(1H)-pyrimidinone (Zebularine); 2',3'-dideoxy-5-fluoro-3'-thiacytidine (Emtriva); 2'-cyclocytidine (Ancitabine); 1-β-D-arabinofuranosyl-5-azacytosine (Fazarabine or ara-AC); 6-azacytidine (6-aza-CR); 5,6-dihydro-5-azacytidine (dH-aza-CR); $N^4$-pentyloxycarbonyl-5'-deoxy-5-fluorocytidine (Capecitabine); $N^4$-octadecyl-cytarabine; and elaidic acid cytarabine.

After its incorporation into replicating DNA, 5-azacytidine or 5-aza-2'-deoxycytidine forms a covalent complex with DNA methyltransferases. DNA methyltransferases are responsible for de novo DNA methylation and for reproducing established methylation patterns in daughter DNA strands of replicating DNA. Inhibition of DNA methyltransferases by 5-azacytidine or 5-aza-2'-deoxycytidine leads to DNA hypomethylation, thereby restoring normal functions to morphologically dysplastic, immature hematopoietic cells and cancer cells by re-expression of genes involved in normal cell cycle regulation, differentiation and death. The cytotoxic effects of these cytidine analogs cause the death of rapidly dividing cells, including cancer cells, that are no longer responsive to normal cell growth control mechanisms. 5-azacytidine, unlike 5-aza-2'-deoxycytidine, also incorporates into RNA. The cytotoxic effects of azacitidine may result from multiple mechanisms, including inhibition of DNA, RNA and protein synthesis, incorporation into RNA and DNA, and activation of DNA damage pathways.

5-Azacytidine and 5-aza-2'-deoxycytidine have been tested in clinical trials and showed significant anti-tumor activity, such as, for example, in the treatment of myelodysplastic syndromes (MDS), acute myelogenous leukemia (AML), chronic myelogenous leukemia (CML), acute lymphocytic leukemia (ALL), and non Hodgkin's lymphoma (NHL). See, e.g., Aparicio et al., Curr. Opin. Invest. Drugs 3(4): 627-33 (2002). 5-Azacytidine has undergone NCI-sponsored trials for the treatment of MDS and has been approved for treating all FAB subtypes of MDS. See, e.g., Kornblith et al., J. Clin. Oncol. 20(10): 2441-2452 (2002); Silverman et al., J. Clin. Oncol. 20(10): 2429-2440 (2002). 5-Azacytidine may alter the natural course of MDS by diminishing the transformation to AML through its cytotoxic activity and its inhibition of DNA methyltransferase. In a Phase III study, 5-azacytidine administered subcutaneously significantly prolonged survival and time to AML transformation or death in subjects with higher-risk MDS. See, e.g., P. Fenaux et al., Lancet Oncol., 2009, 10(3):223-32; Silverman et al., Blood 106(11): Abstract 2526 (2005).

5-Azacytidine and other cytidine analogs are approved for subcutaneous (SC) or intravenous (IV) administration to treat various proliferative disorders. Oral dosing of cytidine analogs would be more desirable and convenient for patients and doctors, e.g., by eliminating injection-site reactions that may occur with SC administration and/or by permitting improved patient compliance. However, oral delivery of cytidine analogs has proven difficult due to combinations of chemical instability, enzymatic instability, and/or poor permeability. For example, cytidine analogs have been considered acid labile and unstable in the acidic gastric environment. Previous attempts to develop oral dosage forms of cytidine analogs have required enteric coating of the drug core to protect the active pharmaceutical ingredient (API) from what was understood and accepted to be therapeutically unacceptable hydrolysis in the stomach, such that the drug is preferably absorbed in specific regions of the lower gastrointestinal tract, such as the jejunum in the small intestine. See, e.g., Sands, et al., U.S. Patent Publication No. 2004/0162263 (application Ser. No. 10/698,983). In addition, a generally accepted belief in the art has been that water leads to detrimental hydrolytic degradation of cytidine analogs during formulation, subsequently affecting the stability of the API in the dosage form. As a result, coatings applied to the drug core for prospective oral delivery of cytidine analogs have previously been limited to organic solvent-based systems to minimize exposure of the API to water.

A great need remains for oral formulations and dosage forms of cytidine analogs, such as, e.g., 5-azacytidine, to potentially permit, inter alia, more advantageous dosing amounts or dosing periods; improved pharmacokinetic profiles, pharmacodynamic profiles, or safety profiles; evaluation of the benefits of long-term or maintenance therapies; development of improved treatment regimens that maximize biologic activity; use of cytidine analogs for treating new diseases or disorders; and/or other potential advantageous benefits.

IV. SUMMARY

Provided herein are pharmaceutical compositions comprising cytidine analogs, wherein the compositions release the API substantially in the stomach upon oral administration. Also provided are methods for making the compositions, and methods for using the compositions to treat diseases and disorders including cancer, disorders related to abnormal cell proliferation, and hematologic disorders, among others.

In certain embodiments, the cytidine analog is 5-azacytidine. In other embodiments, the cytidine analog is 5-aza-2'-deoxycytidine (decitabine or 5-aza-CdR). In yet other embodiments, the cytidine analog is, for example: 1-β-D-arabinofuranosylcytosine (Cytarabine or ara-C); pseudoisocytidine (psi ICR); 5-fluoro-2'-deoxycytidine (FCdR); 2'-deoxy-2',2'-difluorocytidine (Gemcitabine); 5-aza-2'-deoxy-2',2'-difluorocytidine; 5-aza-2'-deoxy-2'-fluorocytidine; 1-β-D-ribofuranosyl-2(1H)-pyrimidinone (Zebularine); 2',3'-dideoxy-5-fluoro-3'-thiacytidine (Emtriva); 2'-cyclocytidine (Ancitabine); 1-β-D-arabinofuranosyl-5-azacytosine (Fazarabine or ara-AC); 6-azacytidine (6-aza-CR); 5,6-dihydro-5-azacytidine (dH-aza-CR); $N^4$-pentyloxycarbonyl-5'-deoxy-5-fluorocytidine (Capecitabine); $N^4$-octadecyl-cytarabine; elaidic acid cytarabine; or their derivatives or related analogs.

Certain embodiments herein provide compositions that are single unit dosage forms comprising a cytidine analog. Certain embodiments herein provide compositions that are non-enteric-coated. Certain embodiments herein provide compositions that are tablets comprising a cytidine analog. Certain embodiments herein provide compositions that are capsules comprising a cytidine analog. The capsules may be, e.g., a hard gelatin capsule or a soft gelatin capsule; particular embodiments provide hydroxypropyl methylcellulose (HPMC) capsules. In certain embodiments, the single unit dosage forms optionally further contain one or more excipients. In certain embodiments, the tablets optionally further contain one or more excipients. In other embodiments, the capsules optionally further contain one or more excipients. In certain embodiments, the composition is a tablet that effects an immediate release of the API upon oral administration. In other embodiments, the composition is a tablet that effects a controlled release of the API substantially in the stomach. In certain embodiments, the composition is a capsule that effects an immediate release of the API upon oral administration. In other embodiments, the composition is a capsule that effects a controlled release of the API substantially in the stomach. In particular embodiments, the tablet contains a drug core that comprises a cytidine analog, and optionally further contains a coating of the drug core, wherein the coating is applied to the drug core using an aqueous solvent, such as, for example, water, or non-aqueous solvent, such as, for example ethanol.

Certain embodiments herein provide methods of making formulations of cytidine analogs intended for oral delivery. Further provided are articles of manufacture containing packaging material, an oral formulation of a cytidine analog, and a label that indicates that the formulation is for the treatment of certain diseases or disorders including, e.g., a cancer, a disorder related to abnormal cell proliferation, a hematologic disorder, or an immune disorder.

Certain embodiments herein provide methods of using the formulations provided herein to treat diseases or disorders including, e.g., cancer, disorders related to abnormal cell proliferation, hematologic disorders, or immune disorders, among others. In certain embodiments, the formulations of cytidine analogs are orally administered to subjects in need thereof to treat a cancer or a hematological disorder, such as, for example, MDS, AML, ALL, CML, NHL, leukemia, or lymphoma; or a solid tumor, such as, for example, sarcoma, melanoma, carcinoma, or cancer of the colon, breast, ovary, gastrointestinal system, kidney, lung (e.g., non-small-cell lung cancer and small-cell lung cancer), testicle, prostate, pancreas or bone. In certain embodiments, the formulations of cytidine analogs are orally administered to subjects in need thereof to treat an immune disorder. In certain embodiments, the oral formulations provided herein are co-administered with one or more therapeutic agents to provide a synergistic therapeutic effect in subjects in need thereof. In certain embodiments, the oral formulations provided herein are co-administered with one or more therapeutic agents to provide a resensitization effect in subjects in need thereof. The co-administered agents may be a cancer therapeutic agent, as described herein. In certain embodiments, the co-administered agent(s) may be dosed, e.g., orally or by injection.

In particular embodiments, provided herein are tablets containing 5-azacytidine and methods for making and using the tablets to treat cancer, disorders related to abnormal cell proliferation, or hematologic disorders. In certain embodiments, the tablets optionally further contain one or more excipients such as, for example, glidants, diluents, lubricants, colorants, disintegrants, granulating agents, binding agents, polymers, and/or coating agents. Examples of ingredients useful in preparing certain formulations provided herein are described in, e.g., Etter et al., U.S. Patent Application Publication No. 2008/0057086 (application Ser. No. 11/849,958), which is incorporated herein by reference in its entirety.

Specific embodiments herein provide, inter alia, pharmaceutical compositions comprising a therapeutically effective amount of 5-azacytidine, wherein the composition releases the 5-azacytidine substantially in the stomach following oral administration to a subject. Further embodiments provide the aforementioned compositions, which: are immediate release compositions; do not have an enteric coating (i.e., are non-enteric-coated); are tablets; are capsules; further comprise an excipient selected from any excipient disclosed herein; further comprise a permeation enhancer; further comprise d-alpha-tocopheryl polyethylene glycol 1000 succinate; further comprise a permeation enhancer in the formulation at about 2% by weight relative to the total weight of the formulation; are essentially free of a cytidine deaminase inhibitor; are essentially free of tetrahydrouridine; have an amount of 5-azacytidine of at least about 40 mg; have an amount of 5-azacytidine of at least about 400 mg; have an amount of 5-azacytidine of at least about 1000 mg; achieve an area-under-the-curve value of at least about 200 ng-hr/mL following oral administration to a subject; achieve an area-under-the-curve value of at least about 400 ng-hr/mL following oral administration to a subject; achieve a maximum plasma concentration of at least about 100 ng/mL following oral administration to a subject; achieve a maximum plasma concentration of at least about 200 ng/mL following oral administration to a subject; achieve a time to maximum plasma concentration of less than about 90 minutes following oral administration to a subject; and/or achieve a time to maximum plasma concentration of less than about 60 minutes following oral administration to a subject.

Specific embodiments herein provide a pharmaceutical composition for oral administration comprising a therapeutically effective amount of 5-azacytidine, which releases the 5-azacytidine substantially in the stomach and achieves an area-under-the-curve value of at least about 200 ng-hr/mL following oral administration.

Specific embodiments herein provide a pharmaceutical composition for oral administration comprising a therapeutically effective amount of 5-azacytidine, which releases the 5-azacytidine substantially in the stomach and achieves an area-under-the-curve value of at least about 400 ng-hr/mL following oral administration.

Specific embodiments herein provide a pharmaceutical composition for oral administration comprising a therapeutically effective amount of 5-azacytidine, which releases the 5-azacytidine substantially in the stomach and achieves a maximum plasma concentration of at least about 100 ng/mL following oral administration.

Specific embodiments herein provide a pharmaceutical composition for oral administration comprising a therapeutically effective amount of 5-azacytidine, which releases the 5-azacytidine substantially in the stomach and achieves a maximum plasma concentration of at least about 200 ng/mL following oral administration.

Specific embodiments herein provide a pharmaceutical composition for oral administration comprising a therapeutically effective amount of 5-azacytidine, which releases the 5-azacytidine substantially in the stomach and achieves a time to maximum plasma concentration of, e.g., less than about 6 hr, less than about 5 hr, less than about 4 hr, less than about 3 hr, less than about 2.5 hr, less than about 2 hr, less than about 1.5 hr, less than about 1 hr, less than about 45 min, or less than about 30 min following oral administration. In specific embodiments, the presence of food may affect (e.g., extend) the total exposure and/or time to maximum plasma concentration.

Specific embodiments herein provide a pharmaceutical composition for oral administration comprising a therapeutically effective amount of 5-azacytidine, which releases the 5-azacytidine substantially in the stomach and achieves a time to maximum plasma concentration of less than about 60 minutes following oral administration.

Specific embodiments herein provide any of the aforementioned compositions, as single unit dosage forms, tablets, or capsules.

Specific embodiments herein provide, inter alia, methods for treating a subject having a disease associated with abnormal cell proliferation, comprising orally administering to the subject a pharmaceutical composition comprising a therapeutically effective amount of 5-azacytidine, wherein the composition releases the 5-azacytidine substantially in the stomach following oral administration to the subject. Further embodiments herein provide the aforementioned methods, in which: the disease is myelodysplastic syndrome; the disease is acute myelogenous leukemia; the method further comprises co-administering to the subject in need thereof an additional therapeutic agent selected from any additional therapeutic agent disclosed herein; the composition is an immediate release composition; the composition does not have an enteric coating; the composition further comprises a permeation enhancer; the composition further comprises the permeation enhancer d-alpha-tocopheryl polyethylene glycol 1000 succinate; the composition further comprises d-alpha-tocopheryl polyethylene glycol 1000 succinate in the formulation at about 2% by weight relative to the total weight of the formulation; the method further comprises not co-administering a cytidine deaminase inhibitor with the cytidine analog; the composition is a single unit dosage form; the composition is a tablet; the composition is a capsule; the composition further comprises an excipient selected from any excipient disclosed herein; the amount of 5-azacytidine is at least about 40 mg; the amount of 5-azacytidine is at least about 400 mg; the amount of 5-azacytidine is at least about 1000 mg; the method achieves an area-under-the-curve value of at least about 200 ng-hr/mL following oral administration to the subject; the method achieves an area-under-the-curve value of at least about 400 ng-hr/mL following oral administration to the subject; the method achieves a maximum plasma concentration of at least about 100 ng/mL following oral administration to the subject; the method achieves a maximum plasma concentration of at least about 200 ng/mL following oral administration to the subject; the method achieves a time to maximum plasma concentration of less than about 90 minutes following oral administration to the subject; and/or the method achieves a time to maximum plasma concentration of less than about 60 minutes following oral administration to the subject.

Specific embodiments herein provide, inter alia, pharmaceutical compositions comprising a therapeutically effective amount of 5-azacytidine, wherein the compositions are for treating a disease or disorder associated with abnormal cell proliferation, wherein the compositions are prepared for oral administration, and wherein the compositions are prepared for release of the 5-azacytidine substantially in the stomach. Further embodiments herein provide the aforementioned compositions, which: have an amount of 5-azacytidine of about 40 mg, about 400 mg, or about 1000 mg; are prepared to achieve an area-under-the-curve value of at least about 200 ng-hr/mL or 400 ng-hr/mL following oral administration; are prepared to achieve a maximum plasma concentration of at least about 100 ng/mL or 200 ng/mL following oral administration; are prepared to achieve a time to maximum plasma concentration of less than about 60 minutes or 90 minutes after being administered; are prepared in the form of an immediate release composition; are prepared for oral administration in combination with an additional therapeutic agent selected from any additional therapeutic agent disclosed herein; are for treating myelodysplastic syndrome or acute myelogenous leukemia; further comprise a permeation enhancer; which further comprise the permeation enhancer d-alpha-tocopheryl polyethylene glycol 1000 succinate; are single unit dosage forms; are tablets or capsules; and/or further comprise an excipient selected from any excipient disclosed herein.

Specific embodiments herein provide, inter alia, uses of 5-azacytidine for the preparation of a pharmaceutical composition for treating a disease associated with abnormal cell proliferation, wherein the composition is prepared for oral administration, and wherein the composition is prepared for release of the 5-azacytidine substantially in the stomach. Further embodiments herein provide the aforementioned uses, in which: the disease is myelodysplastic syndrome or acute myelogenous leukemia; the amount of 5-azacytidine is selected from any amount disclosed herein; and/or the composition is prepared for immediate release. Further embodiments provide, inter alia, methods for treating a subject having a disease or disorder provided herein by administering a pharmaceutical compositions provided herein, wherein the treatment results in improved survival of the subject.

V. BRIEF DESCRIPTION OF THE DRAWINGS

Figure 3:
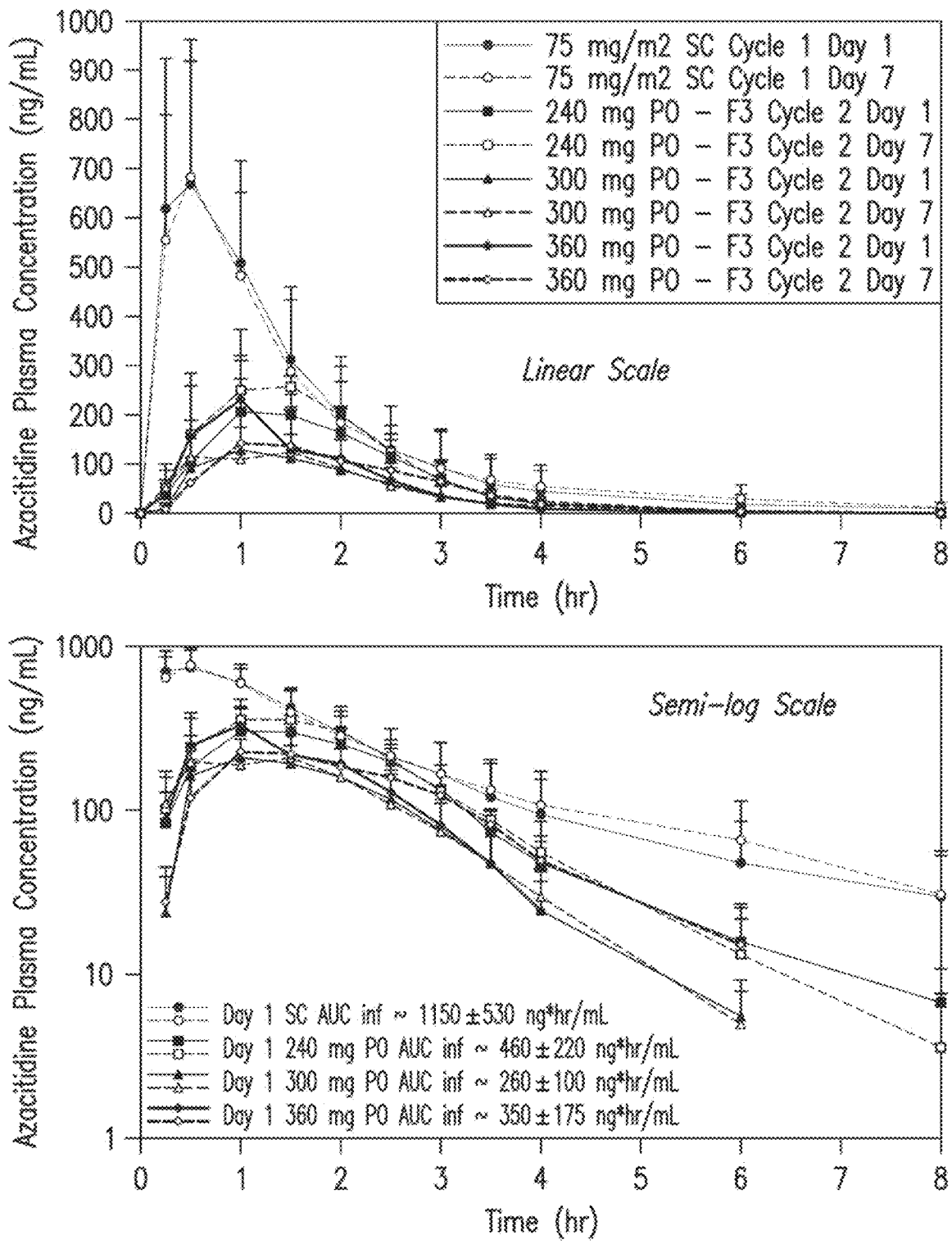
Figure 4A:
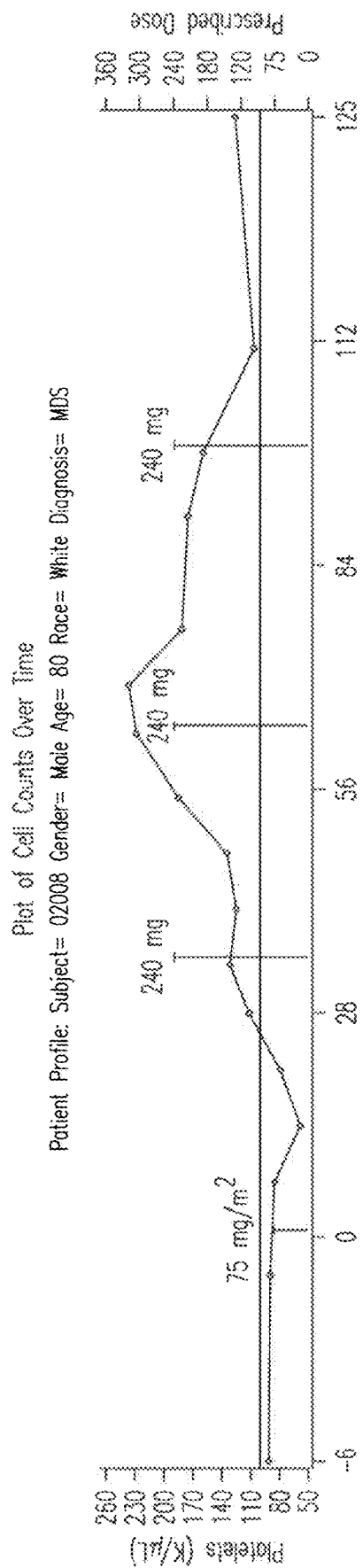
Figure 4B:
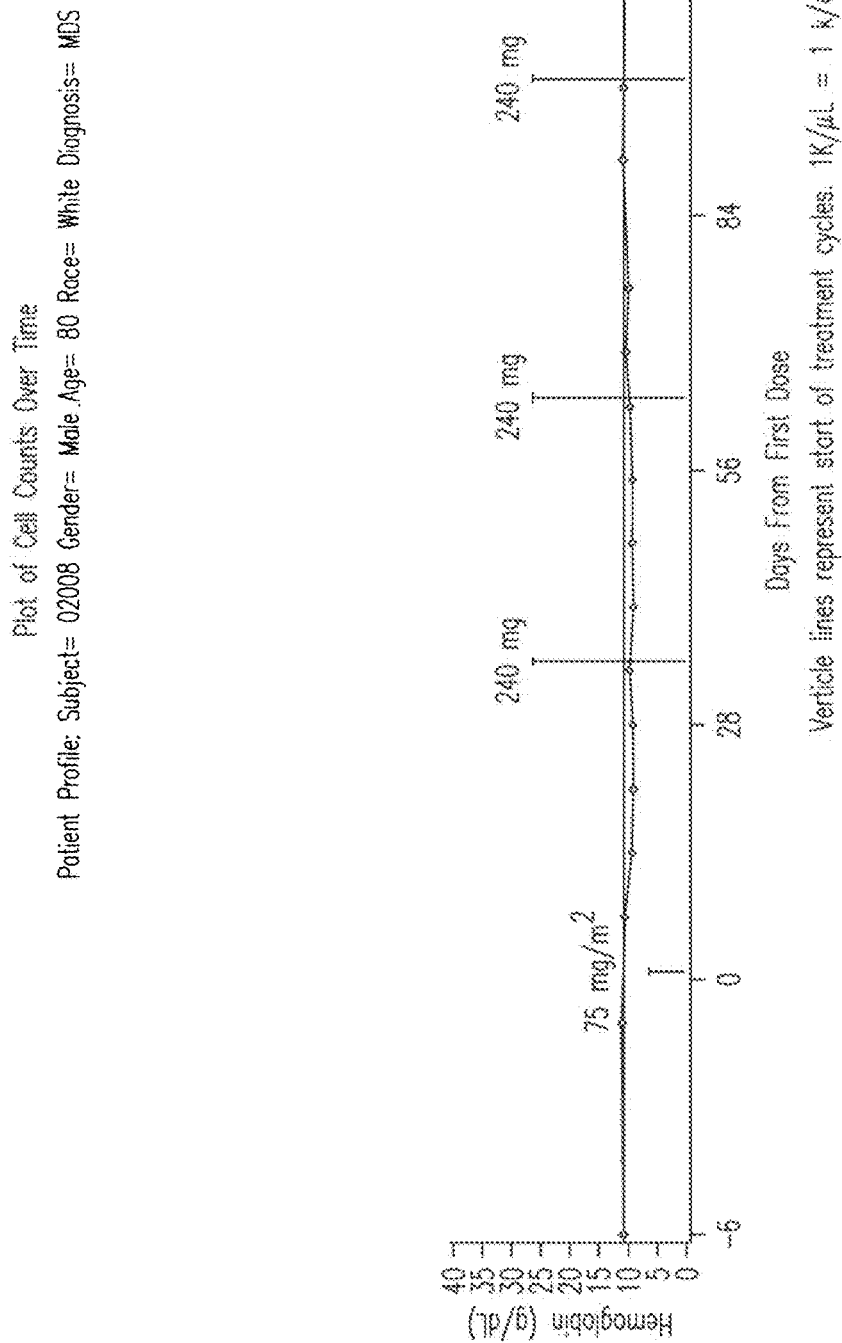
Figure 4C:
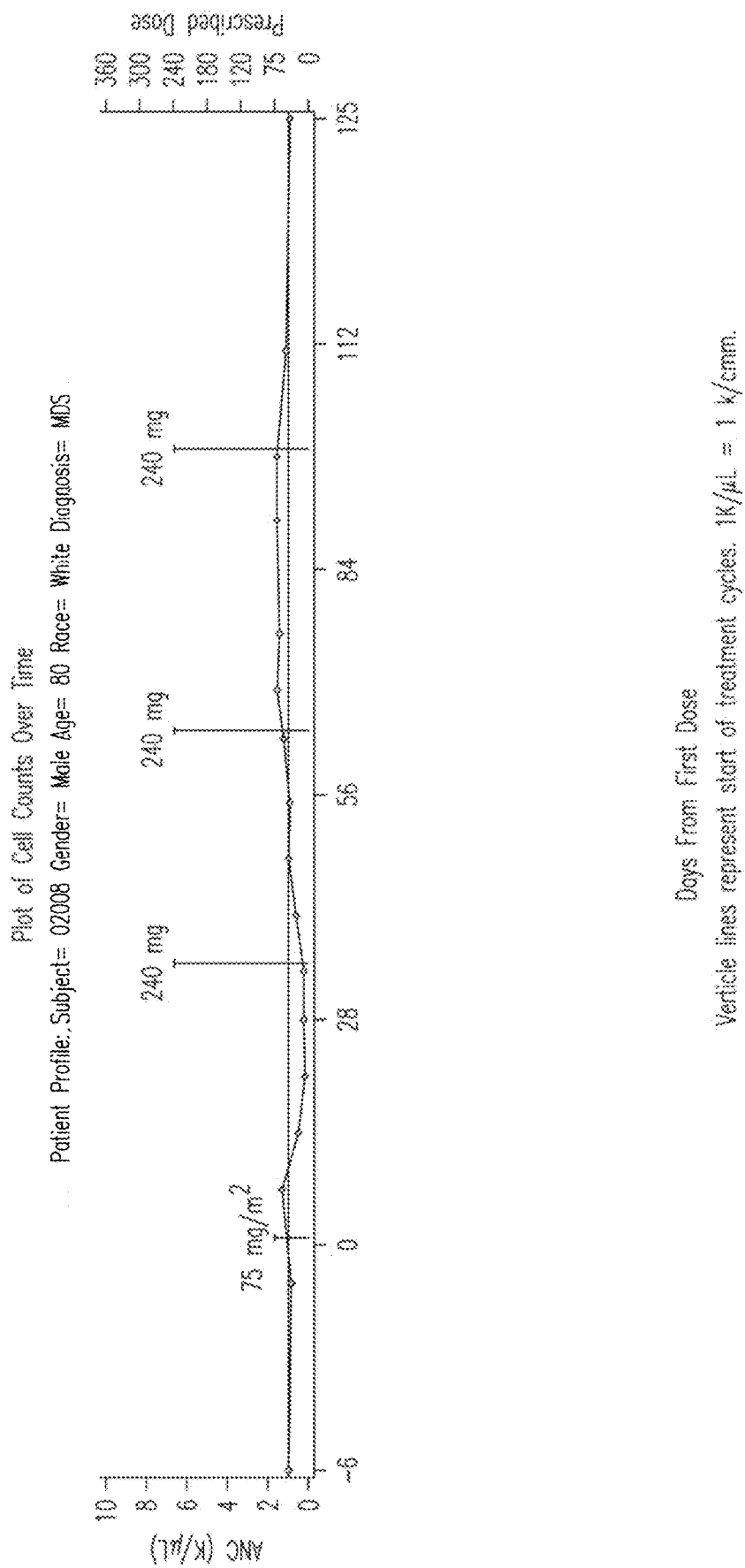
Figure 4D:
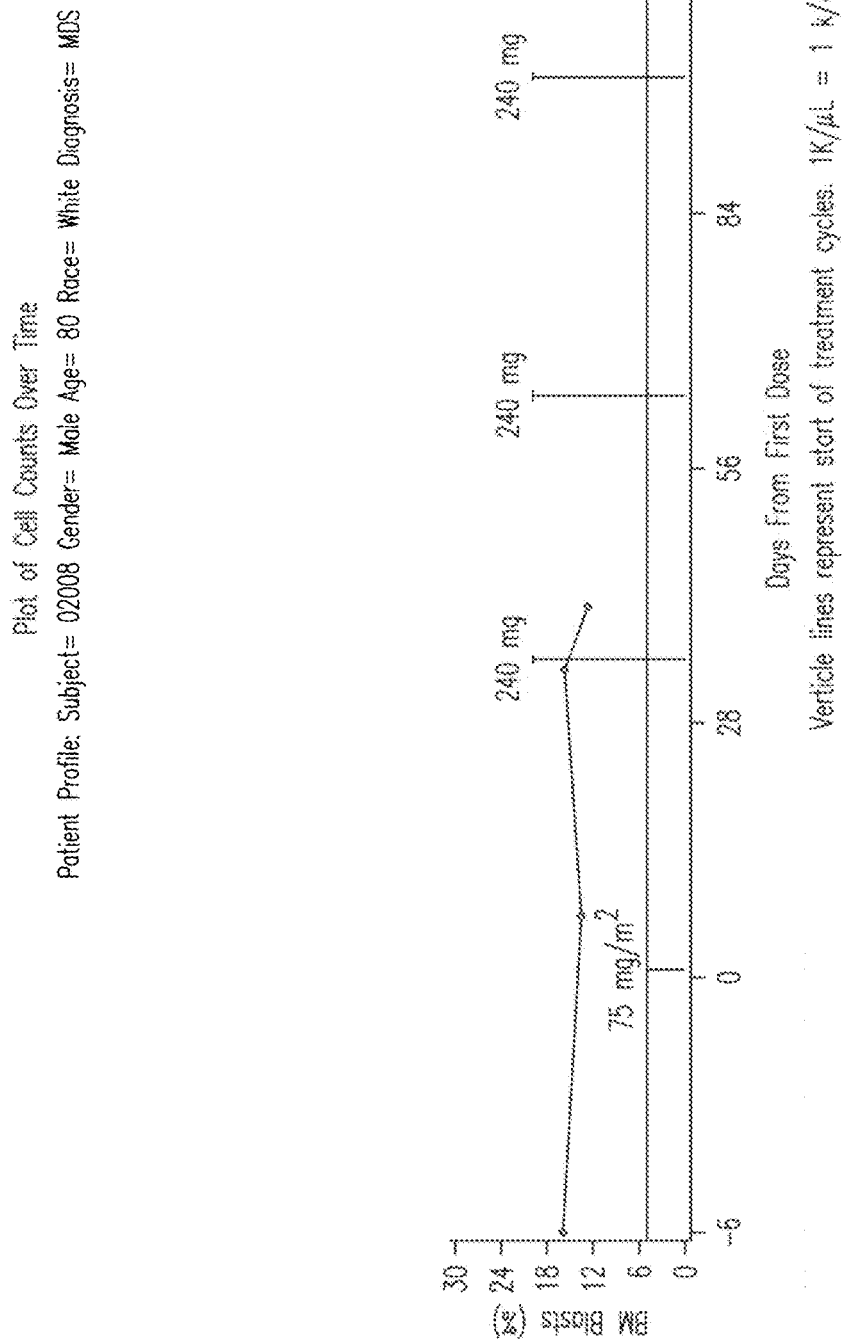

FIG. 3 represents human PK profiles following SC (75 mg/m$^2$) and PO (240 mg, 300 mg, and 360 mg) dosing of azacitidine in a multiple dose escalation study. The azacitidine plasma PK profiles are compared among various doses. The X-axis represents time; the Y-axis represents azacitidine plasma concentrations (mean±SD).

FIGS. 4A-4D represent PD data from an individual patient (Subject 02008, 80 year old male, RAEB-1) collected during a multiple dose escalation study. The patient was dosed with azacitidine Formulation #3, 240 mg. Platelets (K/μL), Hgb (g/dL), ANC (K/μL), and Relative BM Blast (%) are plotted versus sampling dates over the course of the study.

FIGS. 5A-5D represent PD data from an individual patient (Subject 02007, 76 year old male, CMML) collected during a multiple dose escalation study. The patient was dosed with azacitidine Formulation #3, 240 mg. Platelets (K/μL), Hgb (g/dL), ANC (K/μL), and Relative BM Blast (%) are plotted versus sampling dates over the course of the study.

FIGS. 6A-6D represent PD data from an individual patient (Subject 02004, 61 year old male, MDS, MDACC) collected during a multiple dose escalation study. The patient was dosed with azacitidine Formulation 1, 120 mg. Platelets (K/µL), Hgb (g/dL), ANC (K/µL), and Relative BM Blast (%) are plotted versus sampling dates over the course of the study.

Figure 7:
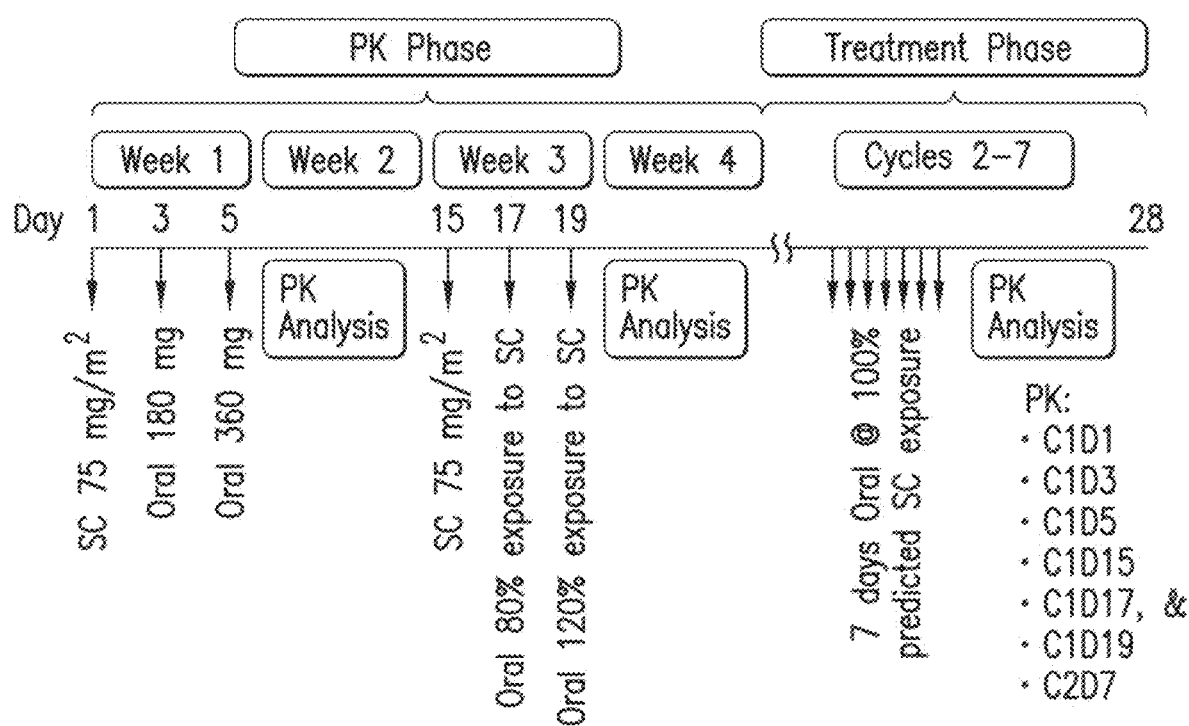

FIG. 7 represents a study design of a Rapid Aza Clinical Evaluation (RACE) study CL008. Doses given on various days within a treatment cycle are depicted. Dose may be administered ±1 day, as long as there is at least 48 hours between doses.

Figure 8:
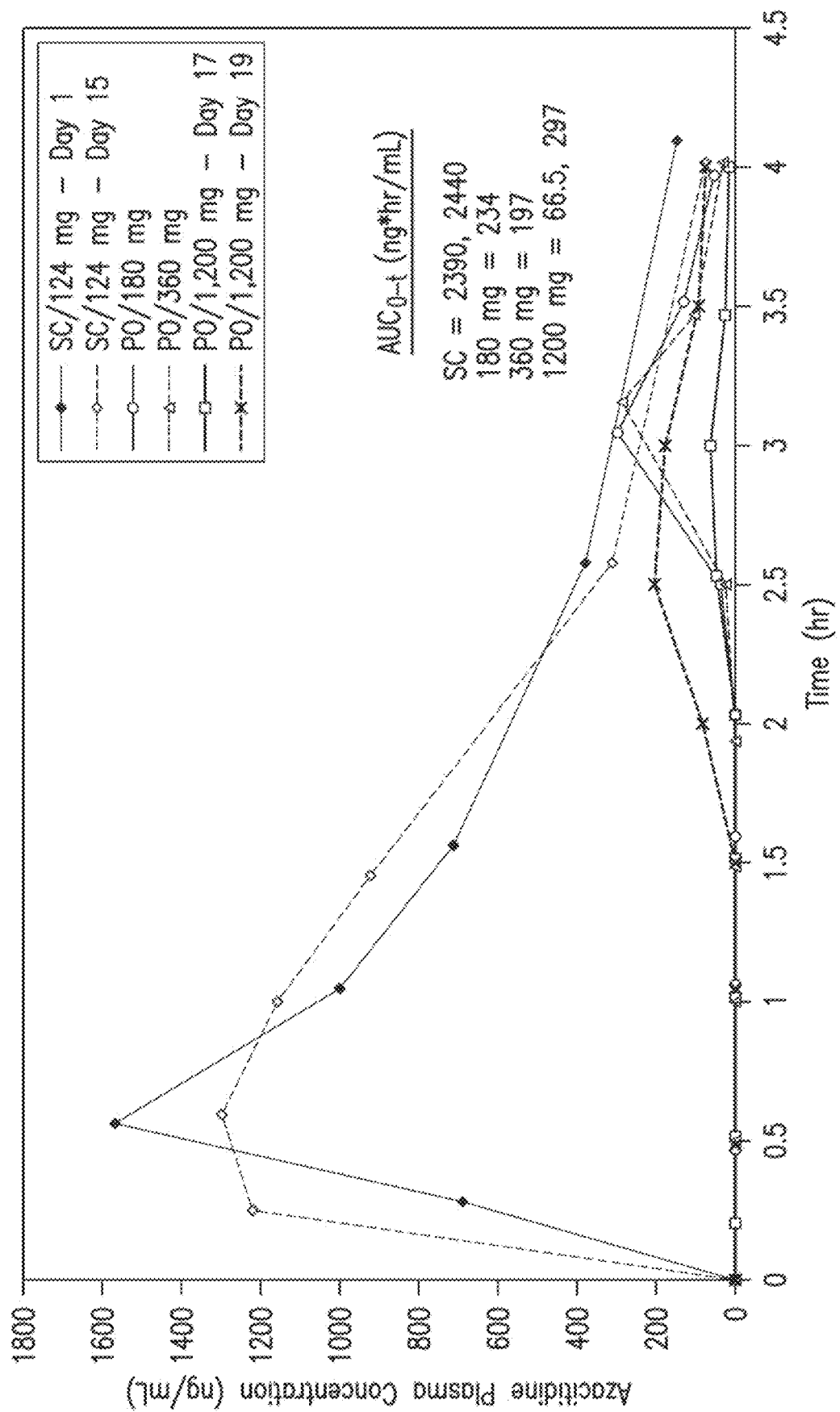

FIG. 8 represents azacitidine human PK profiles from an individual patient (Subject 106003, N=1) following SC (124 mg, 75 mg/m$^2$) and PO (180 mg, 360 mg, 1,200 mg, Formulation 4) dosing of azacitidine from a RACE clinical study. AUC(0-t) values for the SC and PO doses are depicted.

Figure 9:
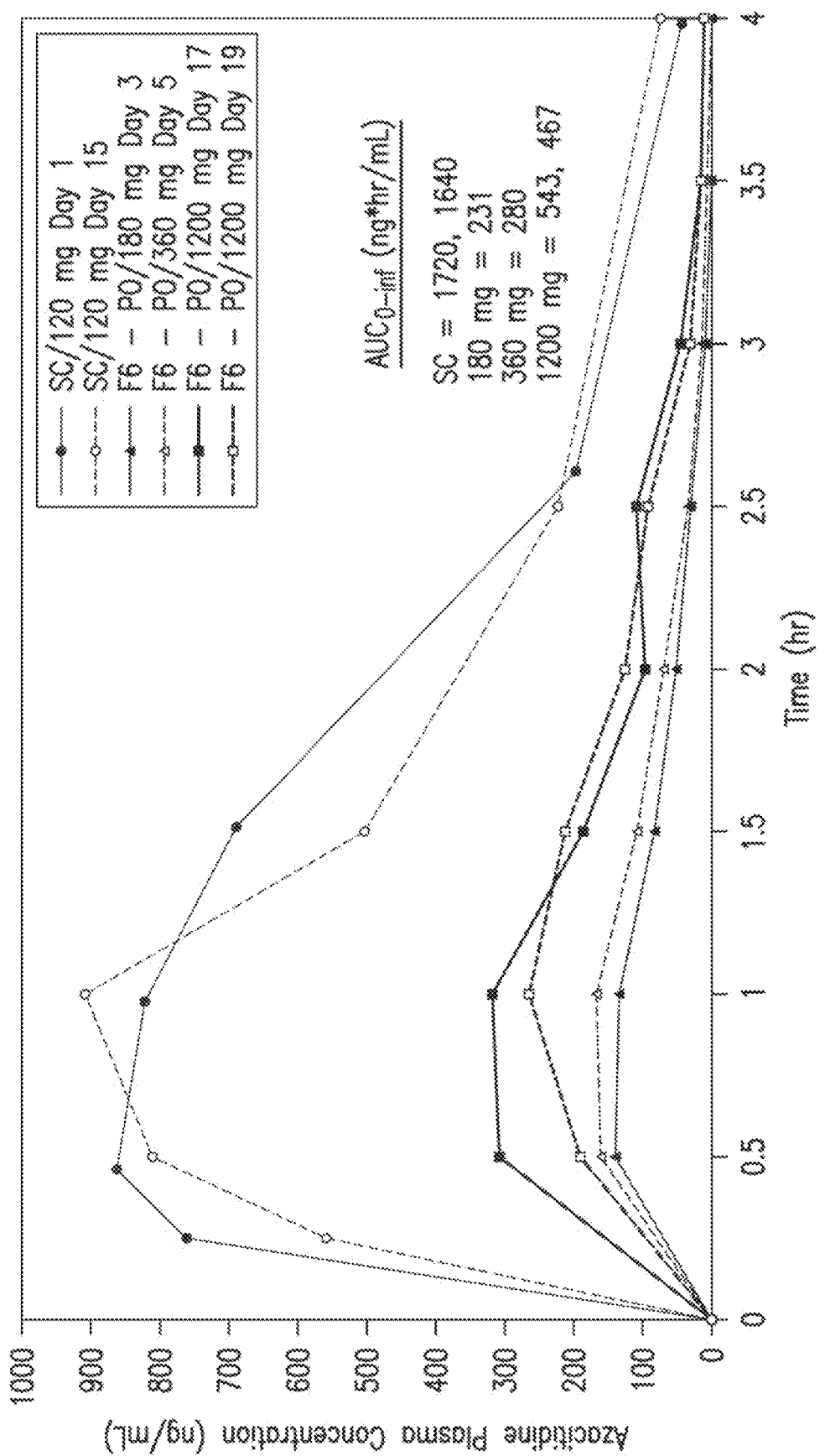

FIG. 9 represents azacitidine human PK profiles from an individual patient (Subject 106004, N=1) following SC (120 mg, 75 mg/m$^2$) and PO (180 mg, 360 mg, 1,200 mg, Formulation 6) dosing of azacitidine from a RACE clinical study. AUC(0-∞) values for the SC and PO doses are depicted.

Figure 10:
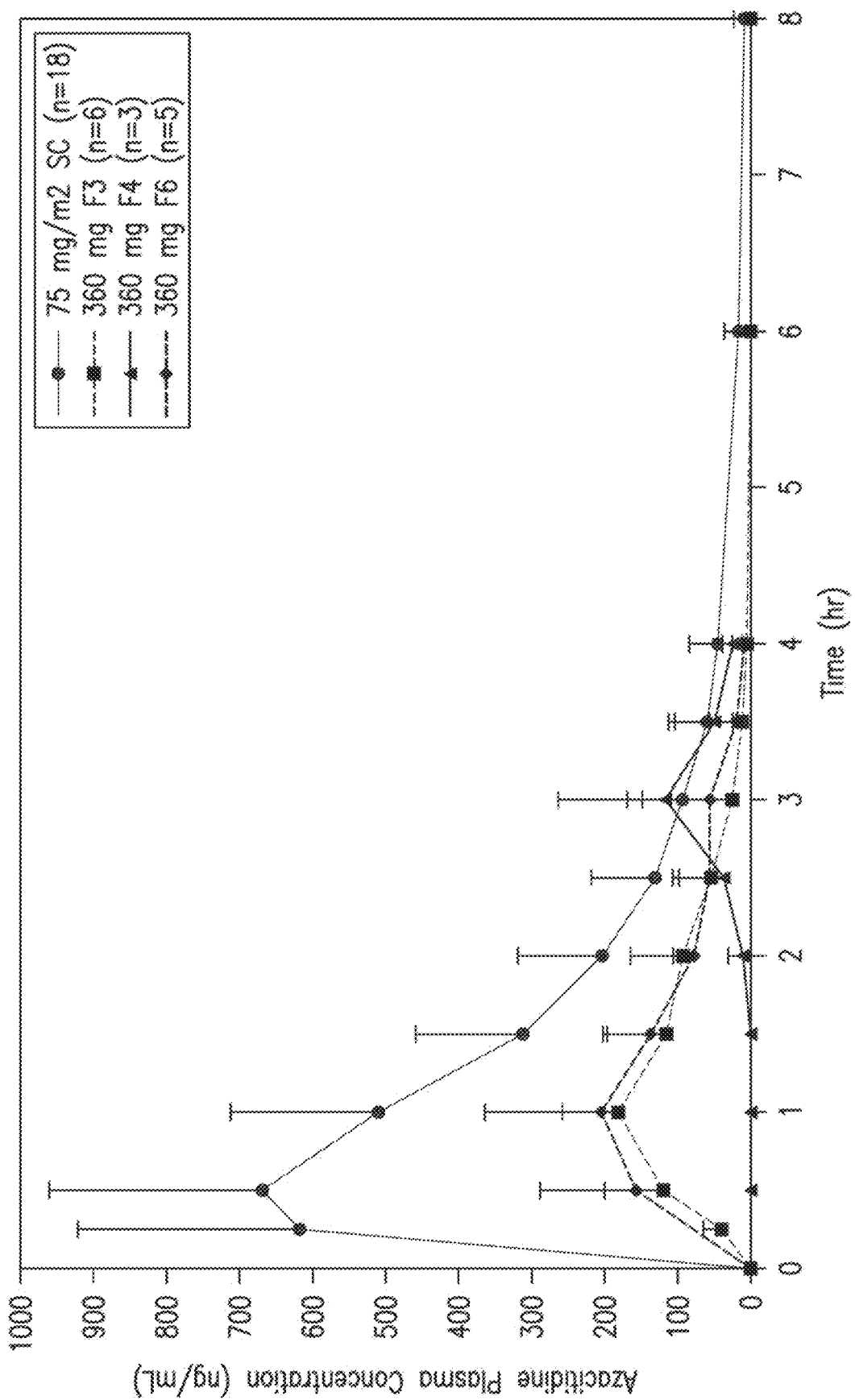

FIG. 10 represents human PK profiles (linear scale) following SC and oral administration of azacitidine in clinical studies.

Figure 11:
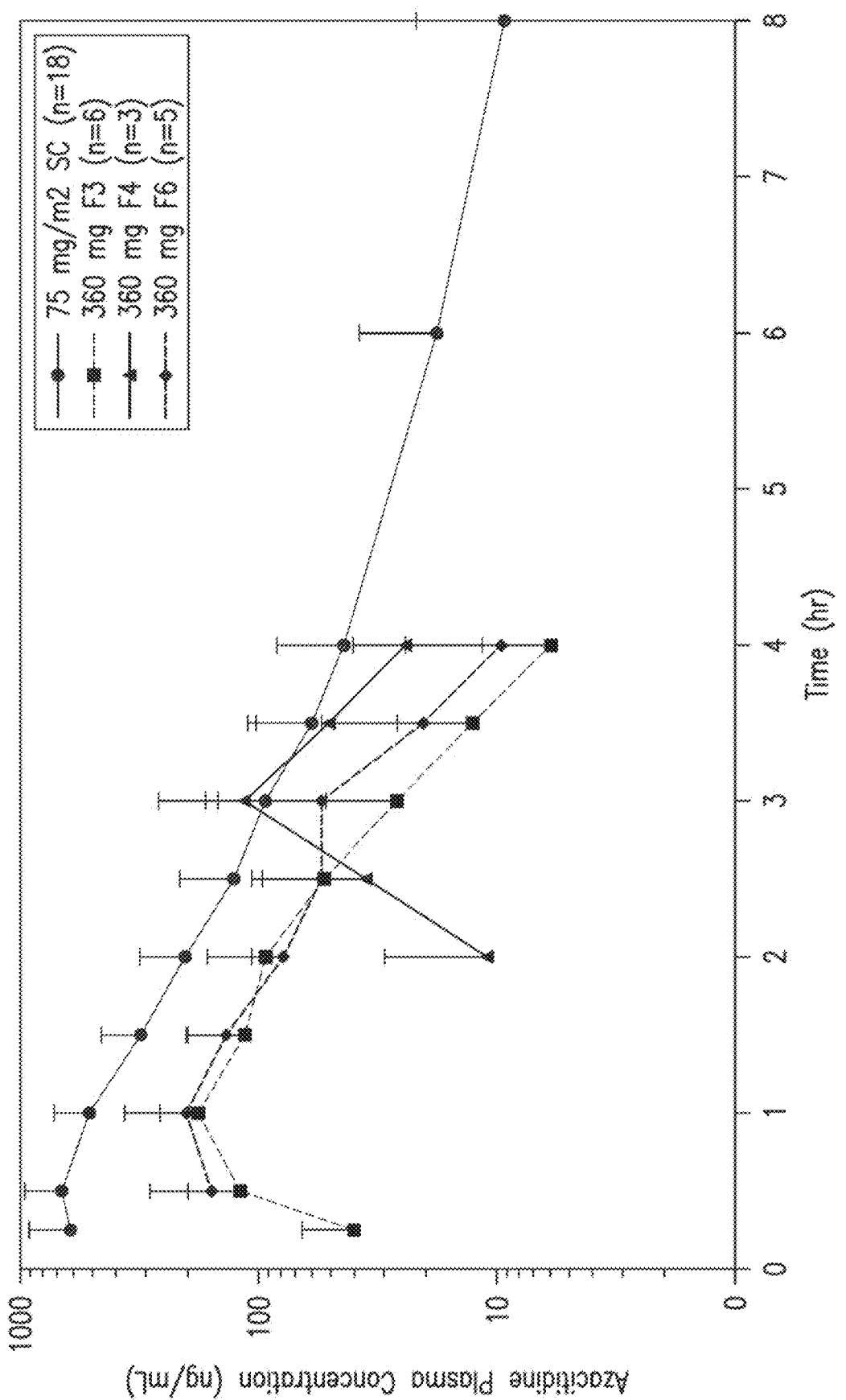

FIG. 11 represents human PK profiles (semi-log scale) following SC and oral administration of azacitidine in clinical studies.

Figure 12:
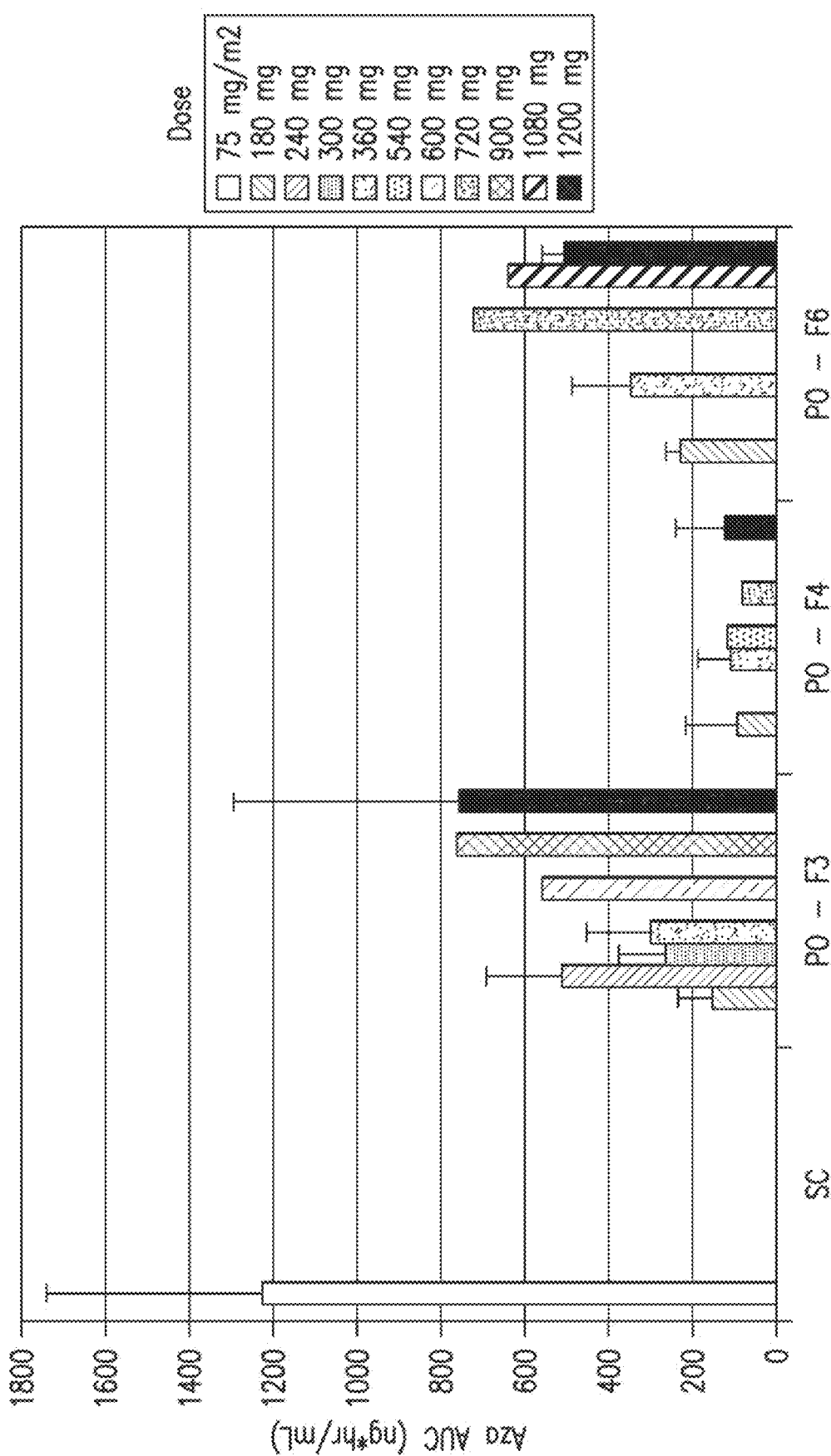

FIG. 12 represents human AUC values following SC dosing of azacitidine and oral dosing of azacitidine with Formulations #3, #4, and #6 at various dosage levels in clinical studies (CL005 and CL008).

Figure 13:
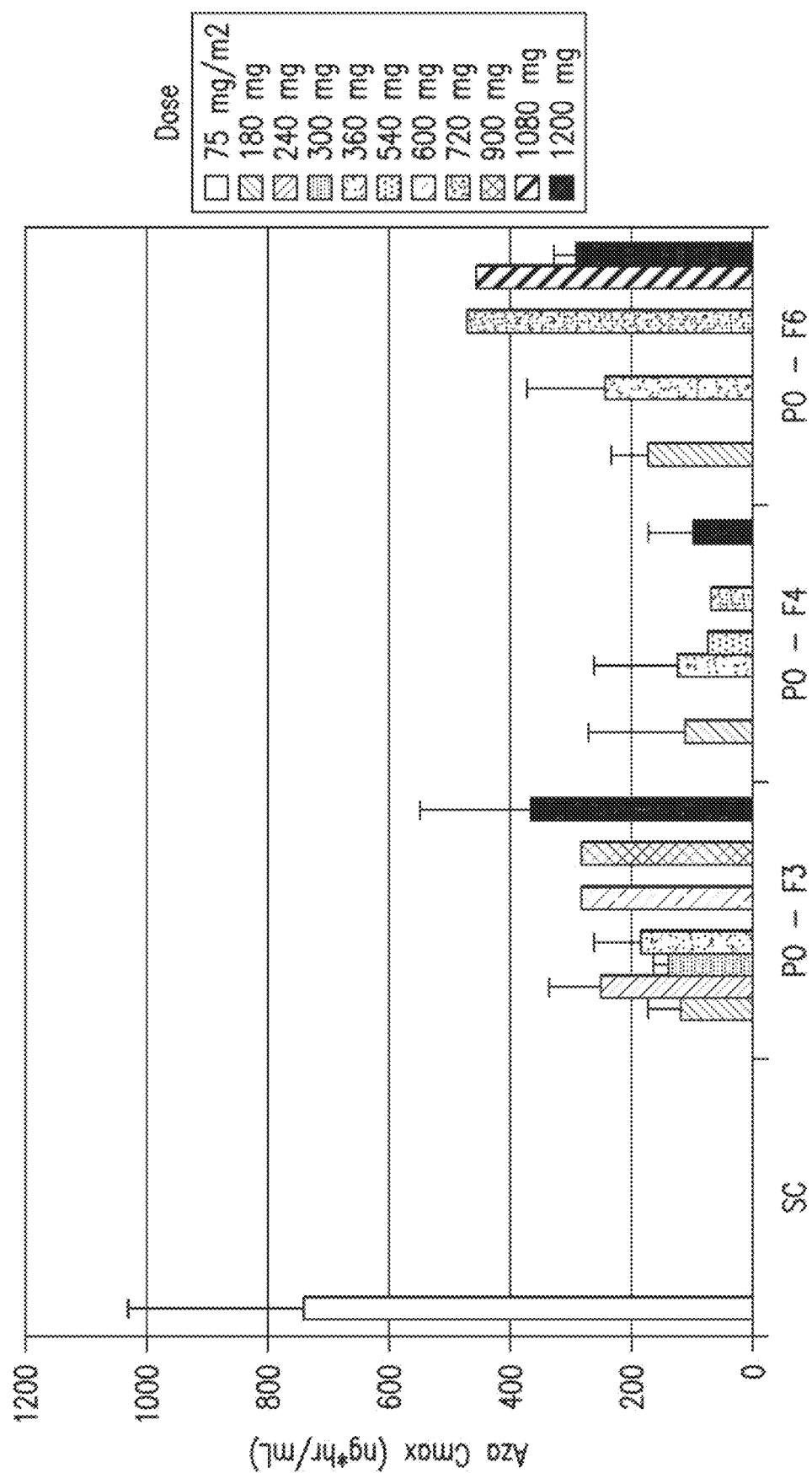

FIG. 13 represents human Cmax values in patients following SC dosing of azacitidine and oral dosing of azacitidine with Formulations #3, #4, and #6 at various dosage levels in clinical studies.

Figure 14:
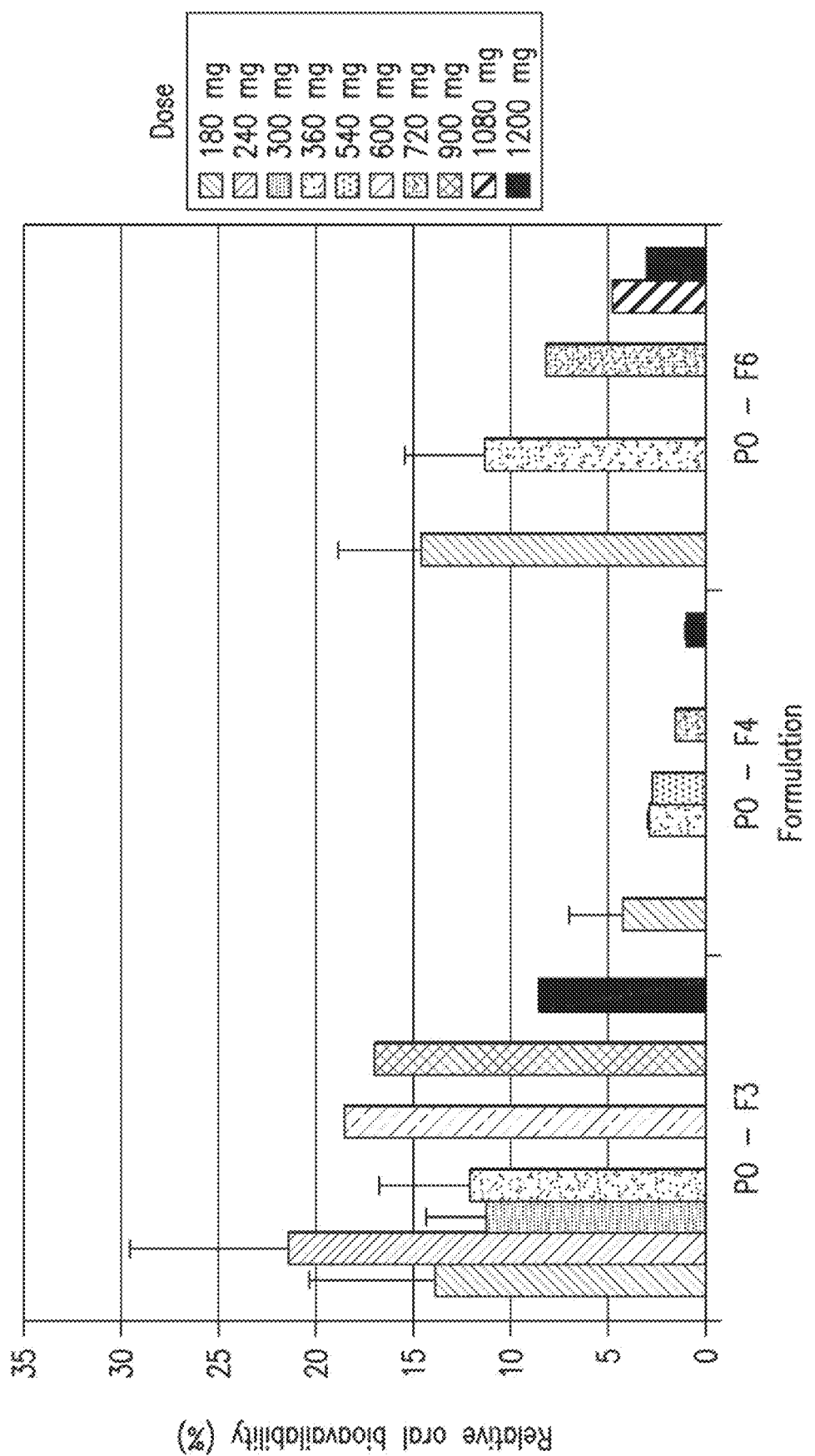

FIG. 14 represents relative oral bioavailability in humans following oral dosing of azacitidine with Formulations #3, #4, and #6 at various dosage levels.

Figure 15:
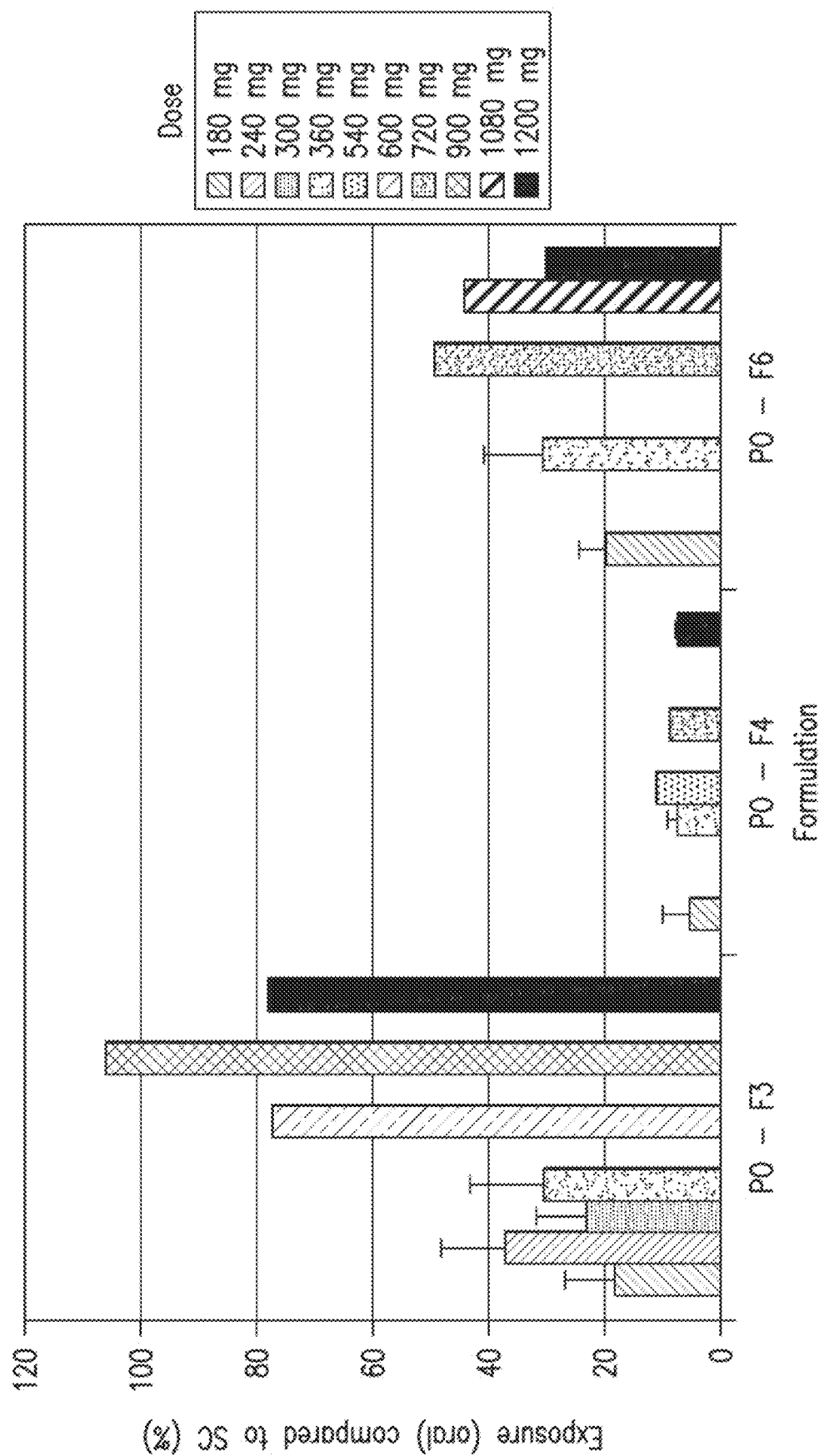

FIG. 15 represents percent exposure in humans relative to SC administration following oral dosing of azacitidine with Formulations #3, #4, and #6 at various dosage levels.

Figure 16:
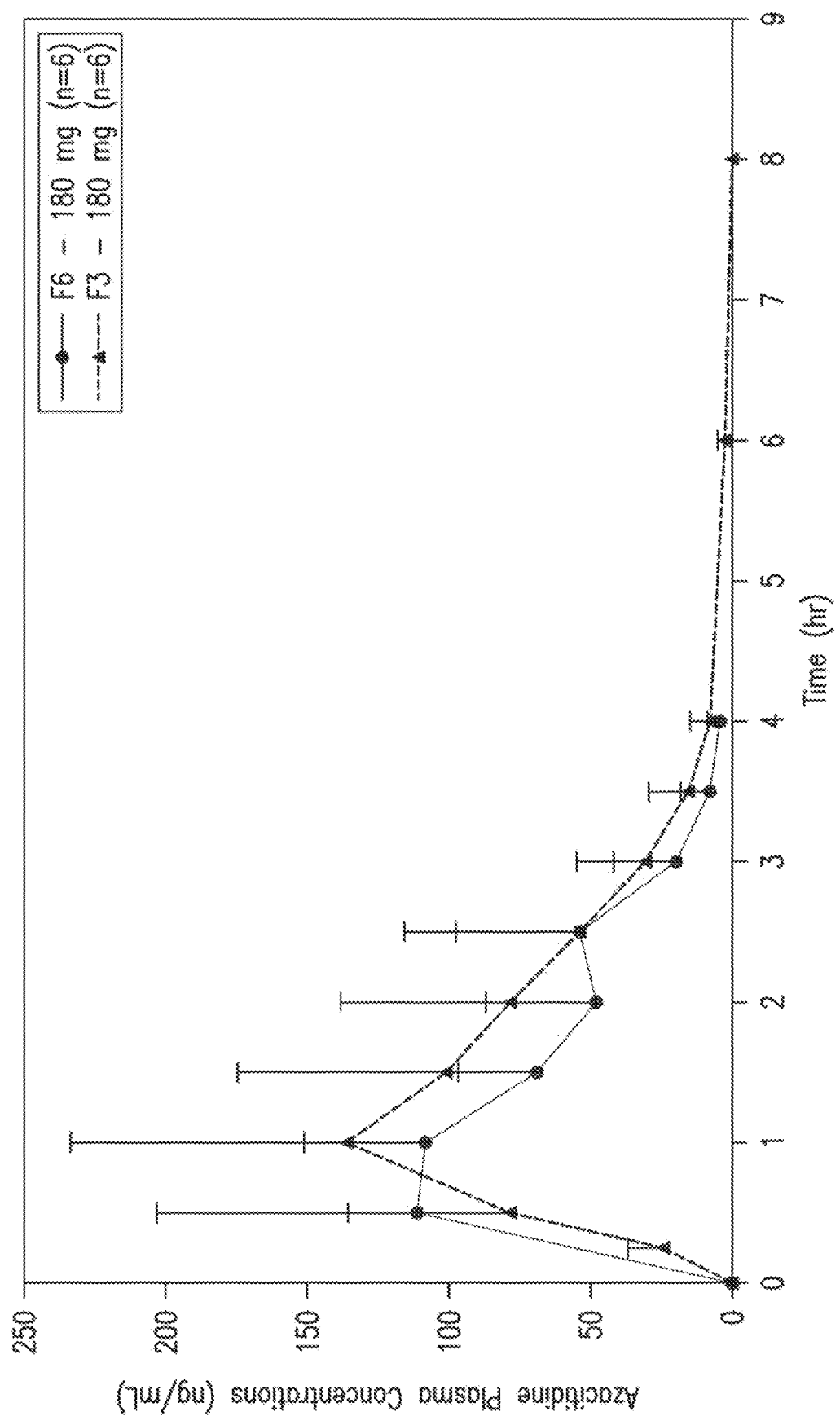

FIG. 16 represents profiles of human plasma concentration versus time (linear scale) following oral dosing of azacitidine with Formulations #3 and #6 and 180 mg (n=6).

Figure 17:
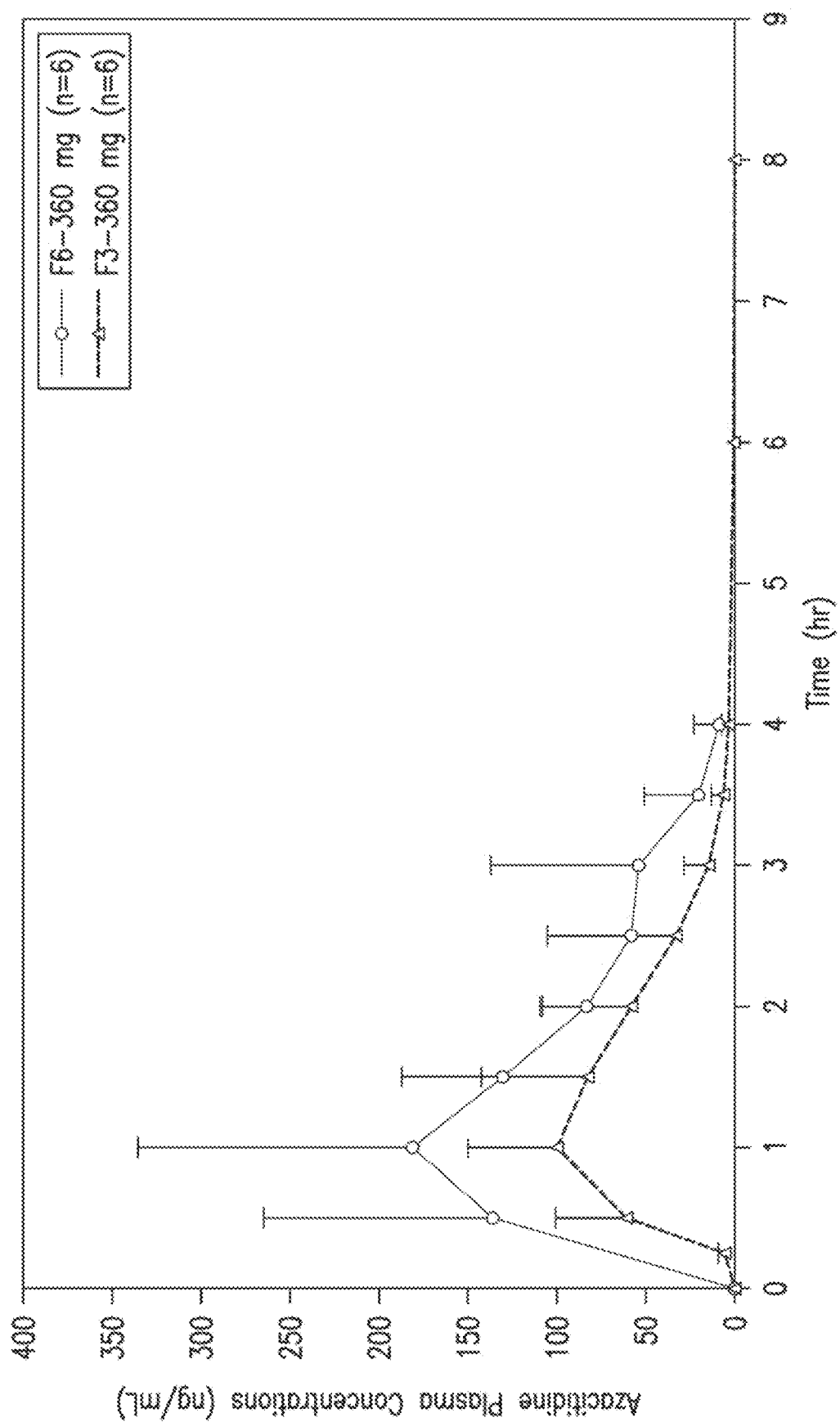

FIG. 17 represents linear scale profiles of human plasma concentration (ng/ml) versus time (hr) following oral dosing of azacitidine with Formulations #3 and #6 and 360 mg (n=6).

Figure 18:
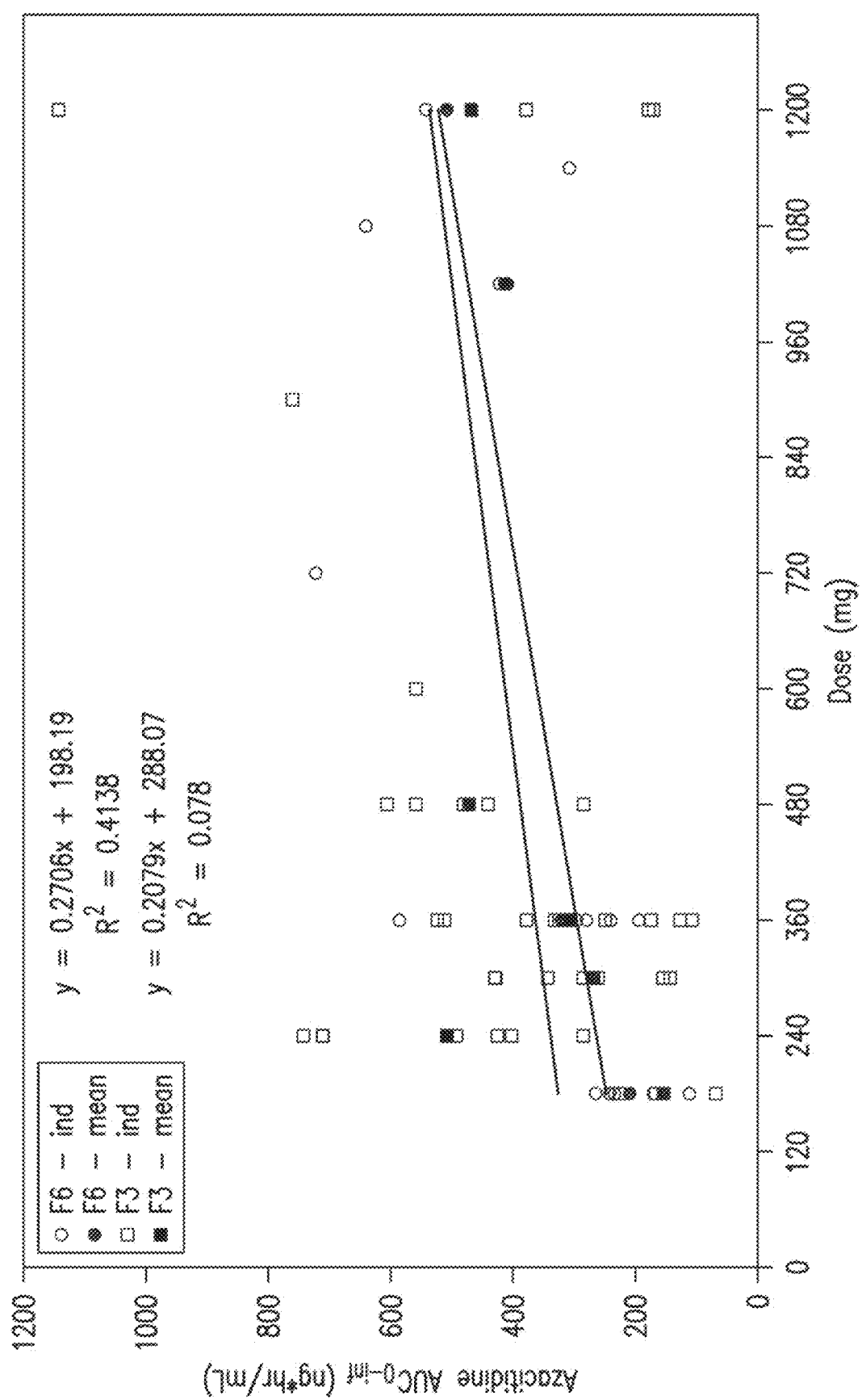

FIG. 18 represents a plot of values for individual ("ind") and mean azacitidine ACU(0-inf) (ng*hr/ml) versus azacitidine dose (mg), with calculated linear regression lines for Formulations #3 and #6.

Figure 19:
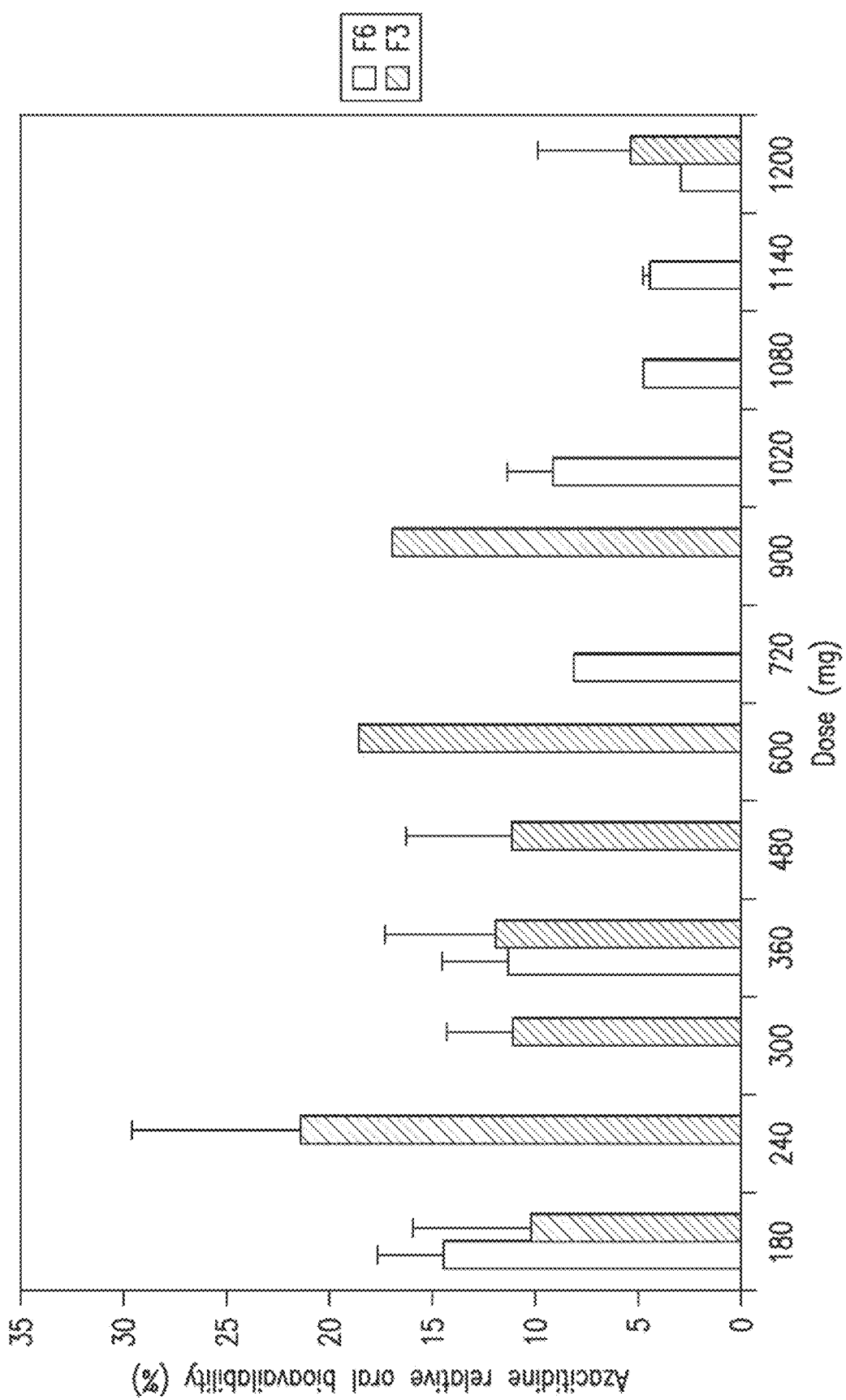

FIG. 19 represents a comparison of azacitidine relative oral bioavailability (%) (mean±SD) versus azacitidine dose (mg) following dosing with Formulation #3 or #6.

Figure 20:
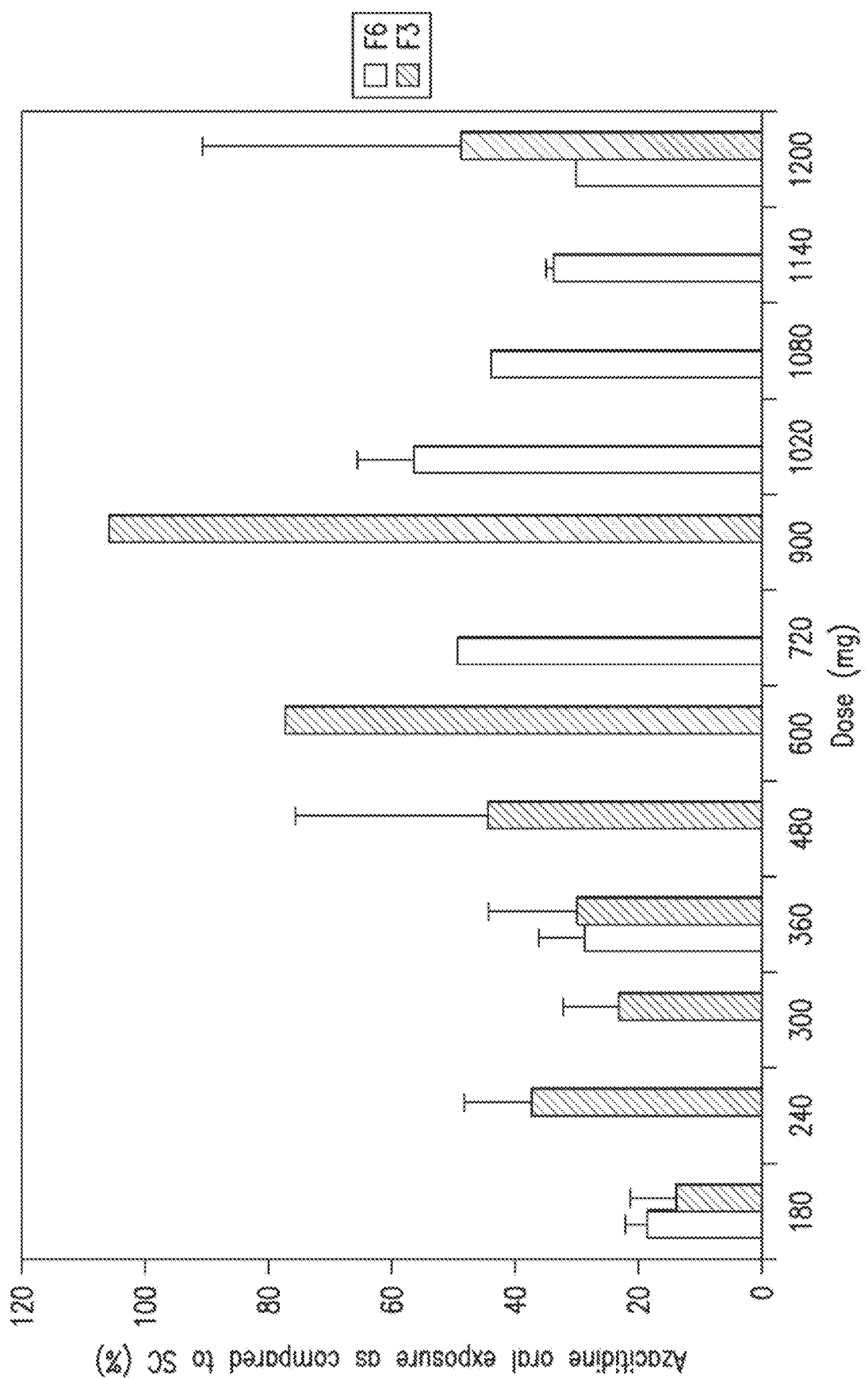

FIG. 20 represents a comparison of azacitidine exposure as compared to SC dose (mean±SD) versus azacitidine dose (mg) following oral administration of Formulation #3 or #6.

VI. DETAILED DESCRIPTION

Unless defined otherwise, all technical and scientific terms used herein have the same meaning as commonly understood by one of ordinary skill in the art. All publications and patents referred to herein are incorporated by reference herein in their entireties.

A. Definitions

As used in the specification and the accompanying claims, the indefinite articles "a" and "an" and the definite article "the" include plural as well as singular referents, unless the context clearly dictates otherwise.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound or dosage form provided herein, with or without one or more additional active agent(s), after the onset of symptoms of the particular disease.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound or dosage form provided herein, with or without one or more other additional active agent(s), prior to the onset of symptoms, particularly to subjects at risk of disease or disorders provided herein. The terms encompass the inhibition or reduction of a symptom of the particular disease. Subjects with familial history of a disease in particular are candidates for preventive regimens in certain embodiments. In addition, subjects who have a history of recurring symptoms are also potential candidates for prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a subject who had suffered from the particular disease in an attempt to prevent or minimize the recurrence of the disease.

As used herein, amelioration of the symptoms of a particular disorder by administration of a particular pharmaceutical composition refers to any lessening, whether permanent or temporary, lasting or transient, that can be attributed to or associated with administration of the composition.

As used herein, and unless otherwise specified, the terms "therapeutically effective amount" and "effective amount" of a compound mean an amount sufficient to provide a therapeutic benefit in the treatment or management of a disease or disorder, or to delay or minimize one or more symptoms associated with the disease or disorder. A "therapeutically effective amount" and "effective amount" of a compound mean an amount of therapeutic agent, alone or in combination with one or more other agent(s), which provides a therapeutic benefit in the treatment or management of the disease or disorder. The terms "therapeutically effective amount" and "effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with one or more other agent(s), which provides a prophylactic benefit in the prevention of the disease. The term "prophylactically effective amount" can encompass an amount that improves overall prophylaxis or enhances the prophylactic efficacy of another prophylactic agent.

"Tumor," as used herein, refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

The terms "cancer" and "cancerous" refer to or describe the physiological condition in mammals that is typically characterized by unregulated cell growth. Examples of cancer include, but are not limited to blood borne (e.g., lymphoma, leukemia) and solid tumors.

The terms "composition," "formulation," and "dosage form," as used herein are intended to encompass compositions comprising the specified ingredient(s) (in the specified amounts, if indicated), as well as any product(s) which result, directly or indirectly, from combination of the specified ingredient(s) in the specified amount(s). By "pharmaceutical" or "pharmaceutically acceptable" it is meant that any diluent(s), excipient(s) or carrier(s) in the composition, formulation, or dosage form are compatible with the other ingredient(s) and not deleterious to the recipient thereof. Unless indicated otherwise, the terms "composition," "formulation," and "dosage form" are used herein interchangeably.

The term "immediate release," when used herein in reference to a composition, formulation, or dosage form provided herein, means that the composition, formulation, or dosage form does not comprise a component (e.g., a coating) that serves to delay the spatial and/or temporal release of some or all of the API from the composition, formulation, or dosage form beyond the stomach following oral administration. In certain embodiments, an immediate release composition, formulation, or dosage form is one that releases the API substantially in the stomach following oral administration. In specific embodiments, an immediate release composition, formulation, or dosage form is one that is not delayed-release. In specific embodiments, an immediate release composition, formulation, or dosage form is one that does not comprise an enteric coating.

The term "non-enteric-coated," when used herein, refers to a pharmaceutical composition, formulation, or dosage form that does not comprise a coating intended to release the active ingredient(s) beyond the stomach (e.g., in the intestine). In certain embodiments, a non-enteric-coated composition, formulation, or dosage form is designed to release the active ingredient(s) substantially in the stomach.

The term "substantially in the stomach," when used herein in reference to a composition, formulation, or dosage form provided herein, means that at least about 99%, at least about 95%, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20%, at least about 15%, or at least about 10% of the cytidine analog is released in the stomach. The term "released in the stomach" and related terms as used herein refer to the process whereby the cytidine analog is made available for uptake by or transport across cells lining the stomach and then made available to the body.

The term "subject" is defined herein to include animals such as mammals, including, but not limited to, primates (e.g., humans), cows, sheep, goats, horses, dogs, cats, rabbits, rats, mice and the like. In specific embodiments, the subject is a human.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

The term "isotopic composition" refers to the amount of each isotope present in a given atomic position, and "natural isotopic composition" refers to the naturally occurring isotopic composition or abundance for a given atomic position. Atomic positions containing their natural isotopic composition may also be referred to herein as "non-enriched." Unless otherwise designated, the atomic positions of the compounds recited herein are meant to represent any stable isotope of that atom. For example, unless otherwise stated, when a position is designated specifically as "H" or "hydrogen," the position is understood to have hydrogen at its natural isotopic composition.

The term "isotopically enriched" refers to an atomic position having an isotopic composition other than the natural isotopic composition of that atom. "Isotopically enriched" may also refer to a compound containing at least one atomic position having an isotopic composition other than the natural isotopic composition of that atom. As used herein, an "isotopologue" is an isotopically enriched compound.

The term "isotopic enrichment" refers to the percentage of incorporation of an amount of a specific isotope at a given atomic position in a molecule in the place of that atom's natural isotopic composition. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%.

The term "isotopic enrichment factor" refers to the ratio between the isotopic composition and the natural isotopic composition of a specified isotope.

With regard to the compounds provided herein, when a particular atomic position is designated as having deuterium or "D," it is understood that the abundance of deuterium at that position is substantially greater than the natural abundance of deuterium, which is about 0.015%. A position designated as having deuterium typically has a minimum isotopic enrichment factor of, in particular embodiments, at least 1000 (15% deuterium incorporation), at least 2000 (30% deuterium incorporation), at least 3000 (45% deuterium incorporation), at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation) at each designated deuterium position.

The isotopic enrichment and isotopic enrichment factor of the compounds provided herein can be determined using conventional analytical methods known to one of ordinary skill in the art, including, e.g., mass spectrometry, nuclear magnetic resonance spectroscopy, and crystallography.

B. Cytidine Analogs

1. Overview

Provided herein are dosage forms, pharmaceutical formulations and compositions comprising cytidine analogs that release the API substantially in the stomach upon oral administration. In certain embodiments, the cytidine analog is 5-azacytidine. In certain embodiments, the cytidine analog is 5-aza-2'-deoxycytidine (decitabine or 5-aza-CdR). In certain embodiments, the cytidine analog is, for example: 1-β-D-arabinofuranosylcytosine (Cytarabine or ara-C); pseudoiso-cytidine (psi ICR); 5-fluoro-2'-deoxycytidine (FCdR); 2'-deoxy-2',2'-difluorocytidine (Gemcitabine); 5-aza-2'-deoxy-2',2'-difluorocytidine; 5-aza-2'-deoxy-2'-fluorocytidine; 1-β-D-ribofuranosyl-2(1H)-pyrimidinone (Zebularine); 2',3'-dideoxy-5-fluoro-3'-thiacytidine (Emtriva); 2'-cyclocytidine (Ancitabine); 1-β-D-arabino-furanosyl-5-azacytosine (Fazarabine or ara-AC); 6-azacytidine (6-aza-CR); 5,6-dihydro-5-azacytidine (dH-aza-CR); $N^4$-pentyloxy-carbonyl-5'-deoxy-5-fluorocytidine (Capecitabine); $N^4$-octadecyl-cytarabine; elaidic acid cytarabine; or a conjugated compound comprising a cytidine analog and a fatty acid (e.g., an azacitidine-fatty acid conjugate, including, but not limited to, CP-4200 (Clavis Pharma ASA) or a compound disclosed in WO 2009/042767, such as aza-C-5'-petroselinic acid ester or aza-C-5'-petroselaidic acid ester).

In certain embodiments, cytidine analogs provided herein include esterified derivatives of cytidine analogs, such as, e.g., esterified derivatives of 5-azacytidine. In particular embodiments, esterified derivatives are cytidine analogs that contain an ester moiety (e.g., an acetyl group) at one or more positions on the cytidine analog molecule. Esterified derivatives may be prepared by any method known in the art. In certain embodiments, esterified derivatives of a cytidine analog serve as prodrugs of the cytidine analog, such that, e.g., following administration of an esterified derivative, the derivative is deacetylated in vivo to yield the cytidine analog. A particular embodiment herein provides 2',3',5'-triacetyl-5-azacytidine (TAC), which possesses favorable physical-chemical and therapeutic properties. See, e.g., International Publication No. WO 2008/092127 (International Application No. PCT/US2008/052124); Ziemba, A. J., et al., "Development of Oral Demethylating Agents for the Treatment of Myelodysplastic Syndrome" (Abstract No. 3369), In: *Proceedings of the 100th Annual Meeting of the American Association for Cancer Research;* 2009 Apr. 18-22; Denver, Co. Philadelphia (Pa.): AACR; 2009 (both of which are incorporated by reference herein in their entireties).

In certain embodiments, the cytidine analogs provided herein include any compound which is structurally related to cytidine or deoxycytidine and functionally mimics and/or antagonizes the action of cytidine or deoxycytidine. Certain embodiments herein provide salts, cocrystals, solvates (e.g., hydrates), complexes, prodrugs, precursors, metabolites, and/or other derivatives of the cytidine analogs provided herein. For example, particular embodiments provide salts, cocrystals, solvates (e.g., hydrates), complexes, precursors, metabolites, and/or other derivatives of 5-azacytidine. Certain embodiments provide cytidine analogs that are not salts, cocrystals, solvates (e.g., hydrates), or complexes of the cytidine analogs provided herein. For example, particular embodiments provide 5-azacytidine in a non-ionized, non-solvated (e.g., anhydrous), non-complexed form. Certain embodiments herein provide mixtures of two or more cytidine analogs provided herein.

Cytidine analogs provided herein may be prepared using synthetic methods and procedures referenced herein or otherwise available in the literature. For example, particular methods for synthesizing 5-azacytidine are taught in, e.g., U.S. Pat. No. 7,038,038 and references discussed therein, each of which is incorporated herein by reference. 5-Azacytidine is also available from Celgene Corporation, Warren, N.J. Other cytidine analogs provided herein may be prepared using previously disclosed synthetic procedures available to a person of ordinary skill in the art.

In certain embodiments, exemplary cytidine analogs have the structures provided below:

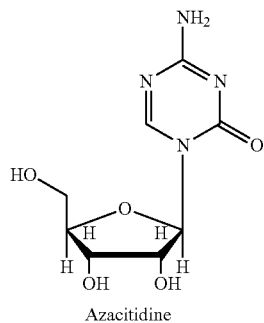

Azacitidine

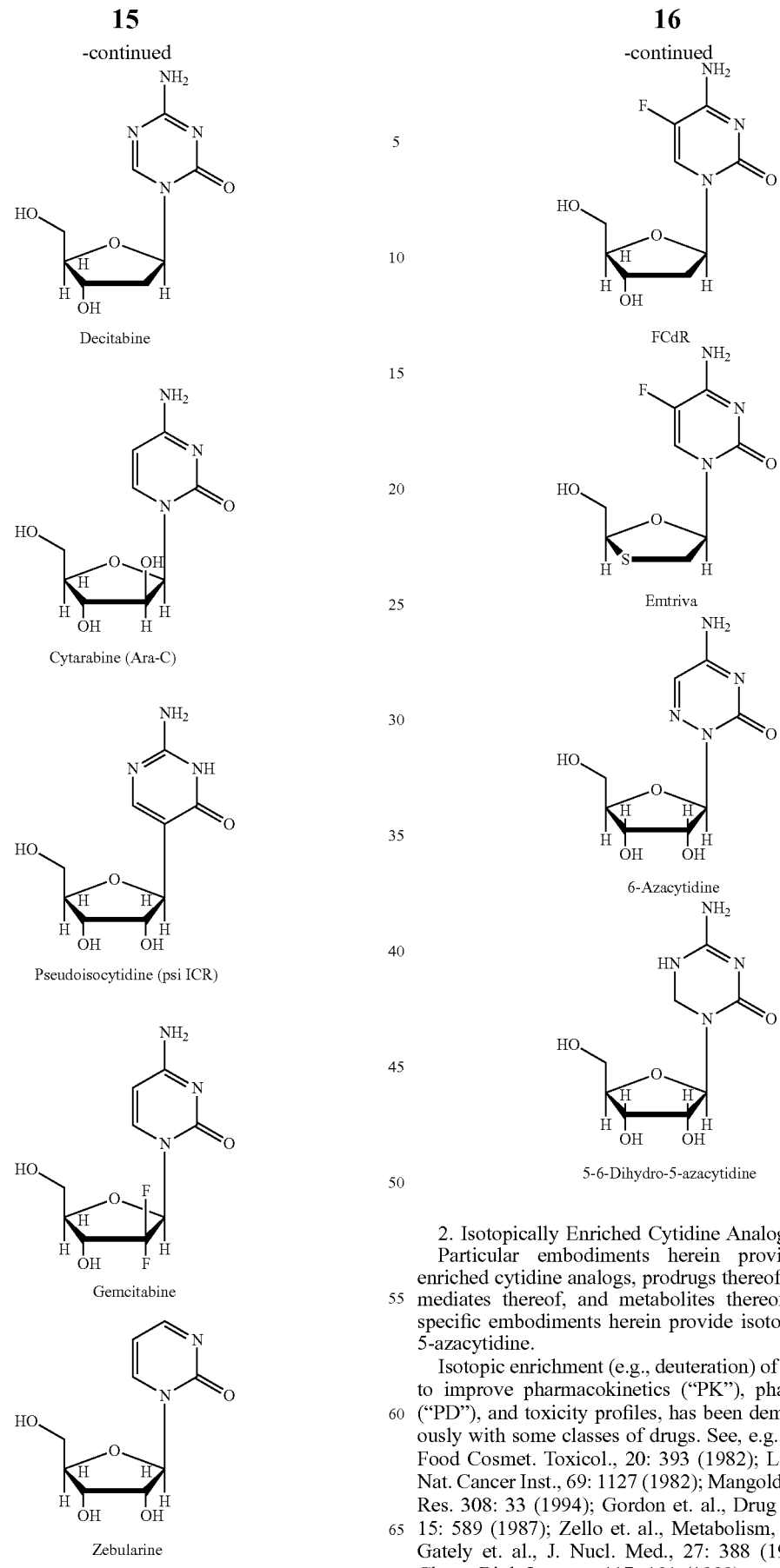

2. Isotopically Enriched Cytidine Analogs

Particular embodiments herein provide isotopically enriched cytidine analogs, prodrugs thereof, synthetic intermediates thereof, and metabolites thereof. For example, specific embodiments herein provide isotopically enriched 5-azacytidine.

Isotopic enrichment (e.g., deuteration) of pharmaceuticals to improve pharmacokinetics ("PK"), pharmacodynamics ("PD"), and toxicity profiles, has been demonstrated previously with some classes of drugs. See, e.g., Lijinsky et. al., Food Cosmet. Toxicol., 20: 393 (1982); Lijinsky et. al., J. Nat. Cancer Inst., 69: 1127 (1982); Mangold et. al., Mutation Res. 308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade, D., Chem. Biol. Interact. 117: 191 (1999).

Without being limited by any particular theory, isotopic enrichment of a drug can be used, for example, to: (1) reduce or eliminate unwanted metabolites; (2) increase the half-life of the parent drug; (3) decrease the number of doses needed to achieve a desired effect; (4) decrease the amount of a dose necessary to achieve a desired effect; (5) increase the formation of active metabolites, if any are formed; and/or (6) decrease the production of deleterious metabolites in specific tissues and/or create a more effective drug and/or a safer drug for combination therapy, whether the combination therapy is intentional or not.

Replacement of an atom for one of its isotopes may often result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). See, e.g, Foster et al., Adv. Drug Res., vol. 14, pp. 1-36 (1985); Kushner et al., Can. J. Physiol. Pharmacol., vol. 77, pp. 79-88 (1999).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. Without being limited by a particular theory, high DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects.

Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, may lead to an analogous kinetic isotope effect.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. As a result, these drugs often require the administration of multiple or high daily doses.

Isotopic enrichment at certain positions of a compound provided herein may produce a detectable KIE that affects the pharmacokinetic, pharmacologic, and/or toxicological profiles of a compound provided herein in comparison with a similar compound having a natural isotopic composition. In one embodiment, the deuterium enrichment is performed on the site of C—H bond cleavage during metabolism.

Certain embodiments herein provide deuterium enriched 5-azacytidine analogs, wherein one or more hydrogen(s) in the 5-azacytidine molecule is/are isotopically enriched with deuterium. In certain embodiments, provided herein are compounds of formula (I):

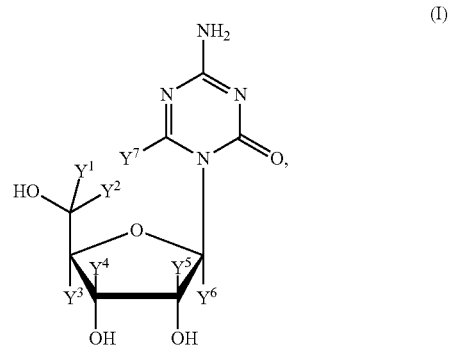

wherein one or more Y atom(s) (i.e., $Y^1$, $Y^2$, $Y^3$, $Y^4$, $Y^5$, $Y^6$ and $Y^7$) is/are hydrogen(s) isotopically enriched with deuterium, and any remaining Y atom(s) is/are non-enriched hydrogen atom(s). In particular embodiments, one, two, three, four, five, six, or seven of the indicated Y atom(s) is/are isotopically enriched with deuterium, and any remaining Y atom(s) is/are non-enriched hydrogen(s).

In certain embodiments, one or more Y atoms on the ribose moiety of Compound (I) are deuterium-enriched. Particular examples include, but are not limited to, the following compounds, in which the label "D" indicates a deuterium-enriched atomic position, i.e., a sample comprising the given compound has a deuterium enrichment at the indicated position(s) above the natural abundance of deuterium:

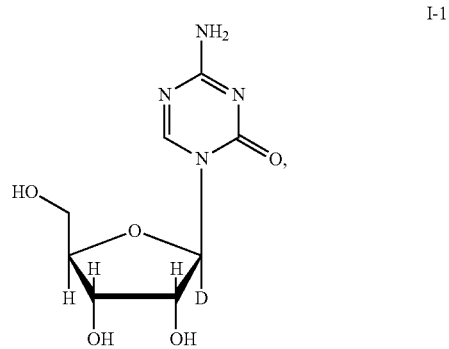

I-2
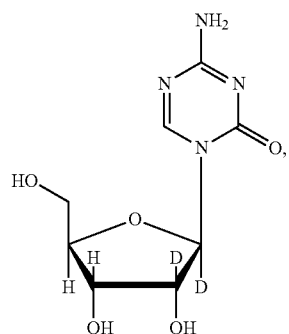

I-3
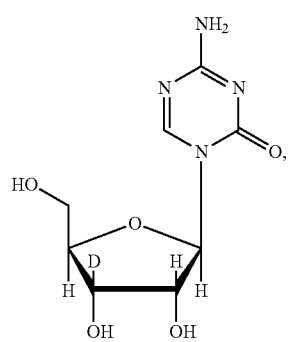

I-4
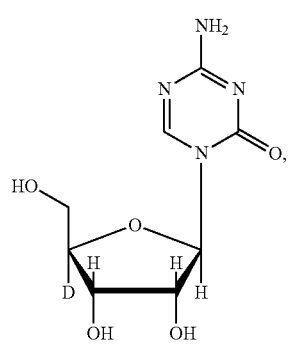

I-5
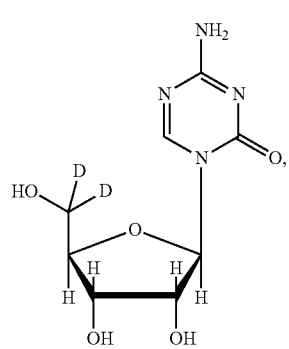

I-6
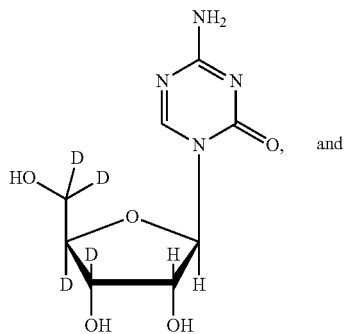
and

I-7
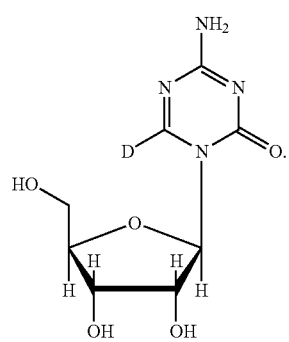

In certain embodiments, the Y atom on the 5-azacytosine moiety of Compound (I) is deuterium-enriched. Particular example includes the following compound, in which the label "D" indicates a deuterium-enriched atomic position, i.e., a sample comprising the given compound has a deuterium enrichment at the indicated position(s) above the natural abundance of deuterium:

I-8
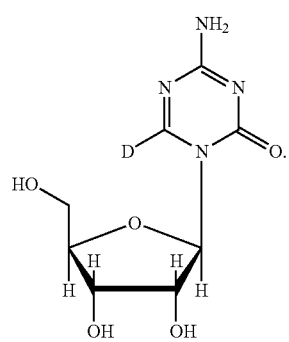

In certain embodiments, one or more Y atoms on the ribose moiety and the Y atom on the 5-azacytosine moiety of Compound (I) are deuterium-enriched. Particular examples include, but are not limited to, the following compounds, in which the label "D" indicates a deuterium-enriched atomic position, i.e., a sample comprising the given compound has a deuterium enrichment at the indicated position(s) above the natural abundance of deuterium:

I-9 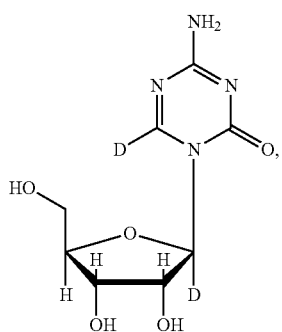

I-10 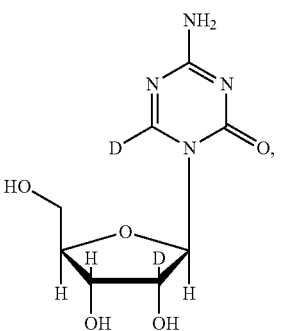

I-11 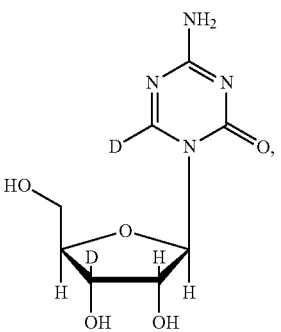

I-12 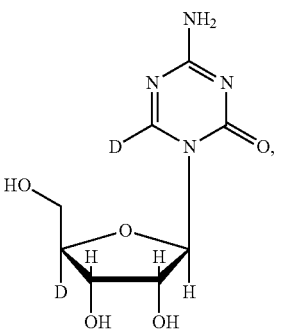

I-13 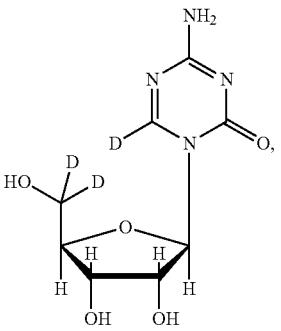

I-14 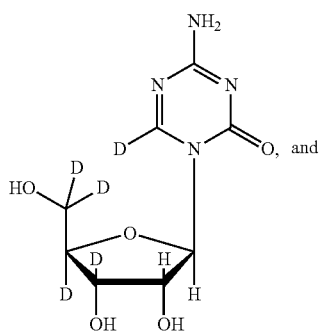

I-15 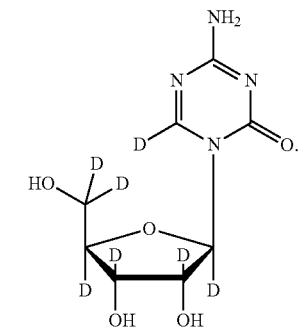

It is understood that one or more deuterium(s) may exchange with hydrogen under physiological conditions.

Certain embodiments herein provide carbon-13 enriched analogs of 5-azacytidine, wherein one or more carbon(s) in the 5-azacytidine molecule is/are isotopically enriched with carbon-13. In certain embodiments, provided herein are compounds of formula (II):

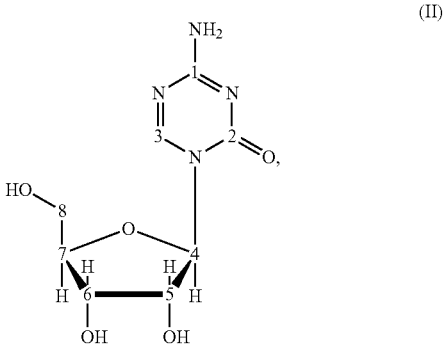

(II)

wherein one or more of 1, 2, 3, 4, 5, 6, 7, or 8 is/are carbon atom(s) isotopically enriched with carbon-13, and any remaining atom(s) of 1, 2, 3, 4, 5, 6, 7, or 8 is/are non-enriched carbon atom(s). In particular embodiments, one, two, three, four, five, six, seven, or eight carbon atom(s) (i.e., atoms 1, 2, 3, 4, 5, 6, 7, and 8) is/are isotopically enriched with carbon-13, and any remaining carbon atom(s) is/are non-enriched.

In certain embodiments, one or more carbon atom(s) of the ribose moiety of Compound (II) are enriched with carbon-13. Particular examples include, but are not limited to, the following compounds, in which the asterisk ("*") indicates a carbon-13 enriched atomic position, i.e., a sample comprising the given compound has a carbon-13 enrichment at the indicated position(s) above the natural abundance of carbon-13:

II-1 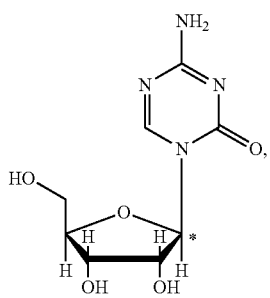
II-2 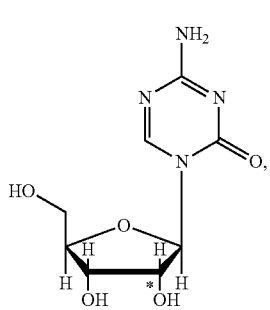
II-3 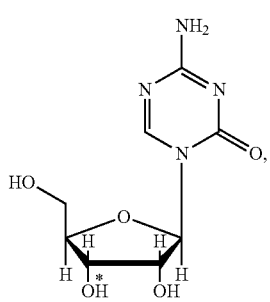
II-4 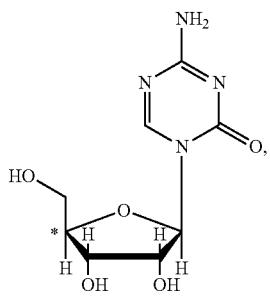
II-5 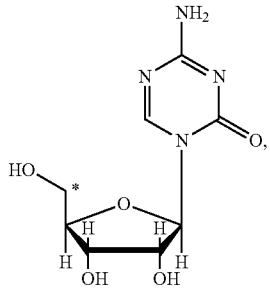
-continued
II-6 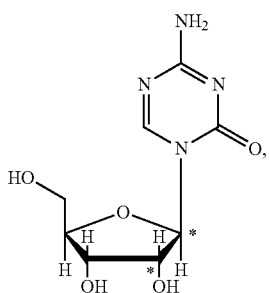
II-7 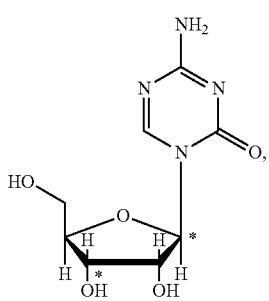
II-8 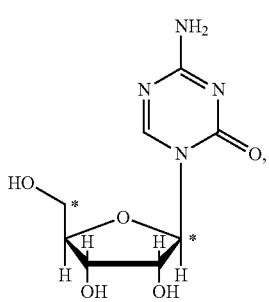
II-9 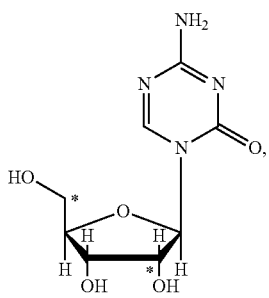
II-10 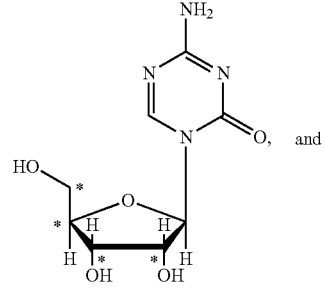, and

II-11

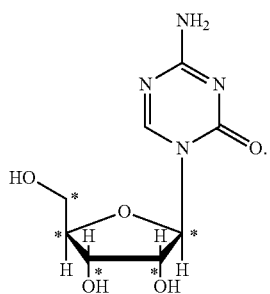

In certain embodiments, one or more carbon atom(s) of the 5-azacytosine moiety of Compound (II) are enriched with carbon-13. Particular examples include, but are not limited to, the following compounds, in which the asterisk "*" indicates a carbon-13 enriched atomic position, i.e., a sample comprising the given compound has a carbon-13 enrichment at the indicated position(s) above the natural abundance of carbon-13:

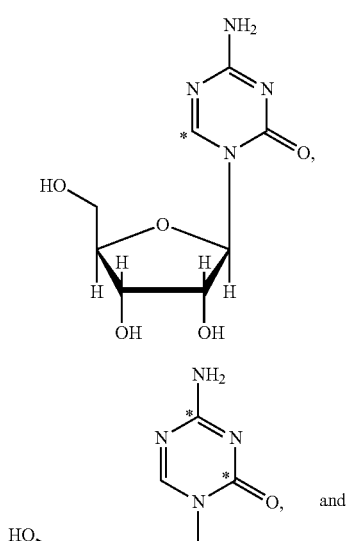

and

In certain embodiments, one or more carbon atoms on the ribose moiety and one or more carbon atoms on the 5-azacytosine moiety of Compound (II) are enriched with carbon-13, i.e., any combination of carbon-13 enrichment for the ribose moiety and carbon-13 enrichment for the azacitosine moiety is encompassed herein.

In certain embodiments, one or more hydrogen(s) is/are enriched with deuterium(s) and one or more carbon(s) is/are enriched with carbon-13, i.e., any combination of deuterium enrichment and carbon-13 enrichment of 5-azacytidine is encompassed herein.

3. Synthesis of Isotopically Enriched Cytidine Analogs

The compounds described herein may be synthesized using any method known to one of ordinary skill in the art. For example, particular compounds described herein are synthesized using standard synthetic organic chemistry techniques known to those of ordinary skill in the art. In some embodiments, known procedures for the synthesis of 5-azacytidine are employed, wherein one or more of the reagents, starting materials, precursors, or intermediates are replaced by one or more isotopically-enriched reagents, starting materials, precursors, or intermediates, including but not limited to one or more deuterium-enriched reagents, starting materials, precursors, or intermediates, and/or one or more carbon-13-enriched reagents, starting materials, precursors, or intermediates. Isotopically enriched reagents, starting materials, precursors, or intermediates are commercially available or may be prepared by routine chemical reactions known to one of skill in the art. In some embodiments, the routes are based on those disclosed in U.S. Pat. No. 7,038,038, which is incorporated herein by reference in its entirety.

In certain embodiments, a suitable isotopically enriched starting material, such as a deuterium-enriched ribose, a deuterium-enriched 5-azacytosine, a carbon-13-enriched ribose, and/or a carbon-13-enriched 5-azacytosine, may be employed as the starting material in the following general scheme to prepare the corresponding deuterium and/or carbon-13 enriched 5-azacytidine (See Scheme 1). Following the procedures in U.S. Pat. No. 7,038,038, 5-azacytosine is treated with hexamethyldisilazane (HMDS) to render a silylated 5-azacytosine. Tetraacetyl-D-ribose is prepared by reacting D-ribose with sodium acetate in acetic anhydride, following the procedures in Brown et al., Biochemical Preparations, 1955, 4, 70-76. The silylated 5-azacytosine is coupled to tetraacetyl-D-ribose in the presence of TMS-triflate, and the resulting protected 5-azacytidine is treated with sodium methoxide in methanol to yield 5-azacytidine. See U.S. Pat. No. 7,038,038.

Scheme 1

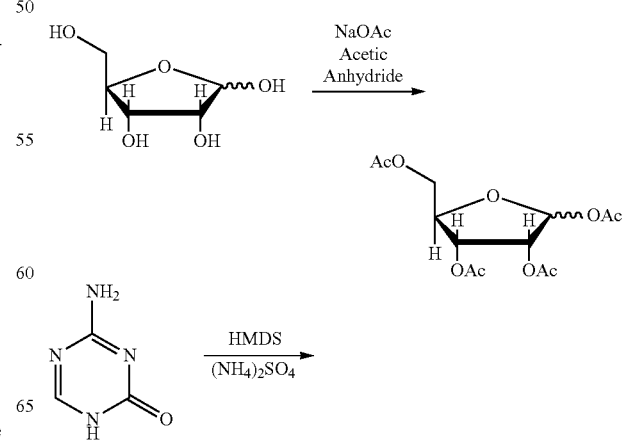

-continued

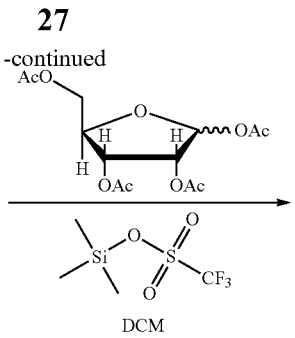

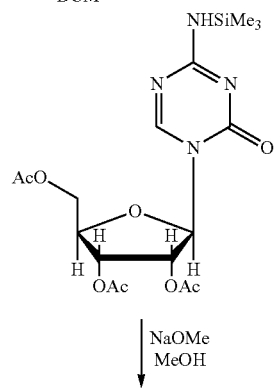

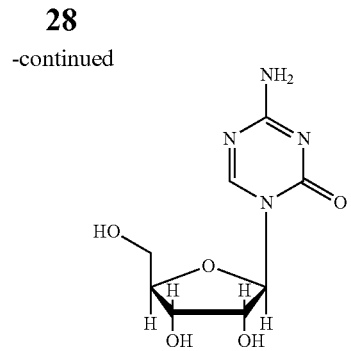

In some embodiments, one or more hydrogen positions in the ribose portion of 5-azacytidine are enriched with deuterium. Such 5-azacytidine analogs may be prepared following Scheme 1 from a suitable deuterium-enriched ribose, purchased from a commercial source or prepared following literature procedures. Specific examples of deuterium-enriched ribose starting material include, but are not limited to, the following compounds listed in Table 1, which may be converted to the corresponding deuterium-enriched 5-azacytidine analogs.

TABLE 1

| Starting Material | Structure | Source/Reference | 5-Azacytidine Product |
|---|---|---|---|
| D-Ribose-1-D | (structure) | Cambridge Isotope Lab. | I-1 |
| D-Ribose-2-D | (structure) | Cambridge Isotope Lab. | I-2 |
| D-Ribose-3-D | (structure) | Omicron Biochemicals, Inc. | I-3 |
| D-Ribose-4-D | (structure) | Omicron Biochemicals, Inc. | I-4 |
| D-Ribose-5,5'-$D_2$ | (structure) | Omicron Biochemicals, Inc. | I-5 |

TABLE 1-continued

| Starting Material | Structure | Source/Reference | 5-Azacytidine Product |
|---|---|---|---|
| D-Ribose-3,4,5,5'-D$_4$ | (structure shown) | Prepared following the procedures in J. Am. Chem. Soc. 1996, 118, 7929-7940. | I-6 |

In other embodiments, the hydrogen position on the 5-azacytosine ring of 5-azacytidine is enriched with deuterium. Such 5-azacytidine analog may be prepared, e.g., from deuterated 5-azacytosine following Scheme 1. The deuterated 5-azacytosine may be prepared, e.g., from suitable deuterated reagents as shown in Scheme 2. See e.g., Grundmann et al., Chem. Ber. 1954, 87, 19-24; Piskala et al., in Zorbach and Tipson (eds.) Synthetic Procedures in Nucleic Acid Chemistry, Vol. 1, Wiley Interscience, New York, 1968, 107-108; Piskala, Collect. Czech. Chem. Comm. 1967, 32, 3966-3976.

Scheme 2

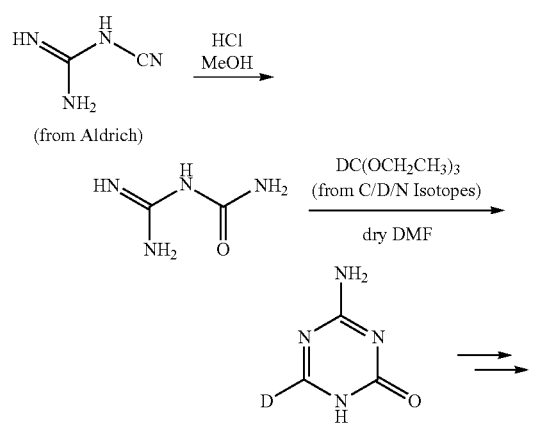

Alternative Conditions for Preparing 5-Azacytosine

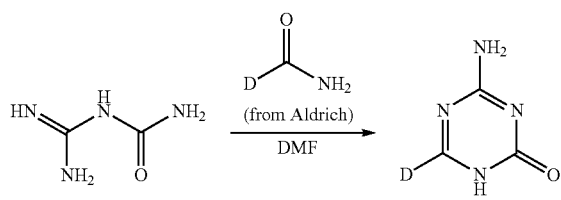

In other embodiments, both the hydrogen position on the 5-azacytosine ring and one or more hydrogen positions in the ribose portion of 5-azacytidine are enriched with deuterium. Such 5-azacytidine analogs may be prepared, e.g., following Scheme 1, coupling a suitable deuterated ribose starting materials with deuterated 5-azacytosine. For example, compounds I-9, I-10, I-11, I-12, I-13, and I-14 may be prepared from the corresponding deuterated ribose starting material listed in Table 1, and deuterated 5-azacytosine prepared according to Scheme 2.

In some embodiments, one or more carbon atoms in the ribose portion of 5-azacytidine are enriched with carbon-13. Such 5-azacytidine analogs may be prepared following Scheme 1 from a suitable carbon-13-enriched ribose, purchased from a commercial source or prepared following literature procedures. Specific examples of carbon-13-enriched ribose starting material include, but are not limited to, the following compounds listed in Table 2, which may be converted to the corresponding carbon-13-enriched 5-azacytidine analogs. (The asterisk "*" indicates a carbon-13 enriched atomic position)

TABLE 2

| Starting Material | Structure | Source/Reference | 5-Azacytidine Product |
|---|---|---|---|
| D-Ribose-1-$^{13}$C | (structure shown) | Sigma Aldrich | II-1 |

TABLE 2-continued

| Starting Material | Structure | Source/Reference | 5-Azacytidine Product |
|---|---|---|---|
| D-Ribose-2-$^{13}$C | 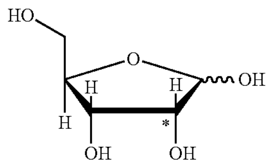 | Sigma Aldrich | II-2 |
| D-Ribose-3-$^{13}$C | 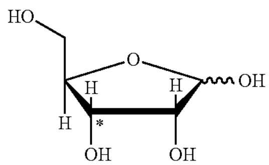 | Omicron Biochemicals, Inc. | II-3 |
| D-Ribose-4-$^{13}$C | 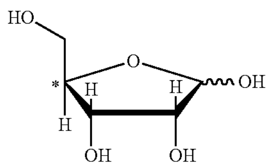 | Omicron Biochemicals, Inc. | II-4 |
| D-Ribose-5-$^{13}$C | 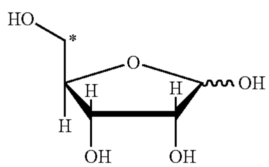 | Cambridge Isotope Lab. | II-5 |
| D-Ribose-1,2-$^{13}$C$_2$ | 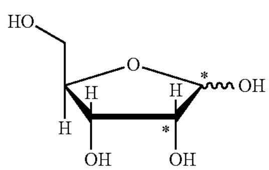 | Sigma Aldrich | II-6 |
| D-Ribose-1,3-$^{13}$C$_2$ | 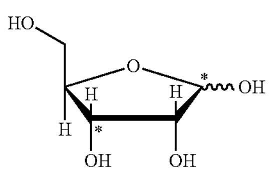 | Omicron Biochemicals, Inc. | II-7 |
| D-Ribose-1,5-$^{13}$C$_2$ | 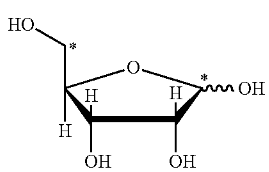 | Omicron Biochemicals, Inc. | II-8 |
| D-Ribose-2,5-$^{13}$C$_2$ | 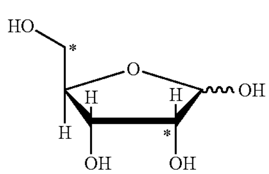 | Omicron Biochemicals, Inc. | II-9 |
| D-Ribose-2,3,4,5-$^{13}$C$_4$ | 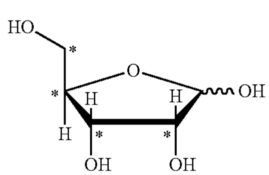 | Sigma Aldrich | II-10 |

TABLE 2-continued

| Starting Material | Structure | Source/Reference | 5-Azacytidine Product |
|---|---|---|---|
| D-Ribose-1,2,3,4,5-$^{13}C_5$ | (structure shown) | Cambridge Isotope Lab. | II-11 |

In other embodiments, one or more carbon atoms in the 5-azacytosine ring are enriched with carbon-13. Such 5-azacytidine analogs may be prepared from a carbon-13-enriched 5-azacytosine following Scheme 1. The carbon-13 enriched 5-azacytosine intermediates may be prepared from suitable carbon-13 enriched reagents as shown in Scheme 3. See e.g., Grundmann et al., Chem. Ber. 1954, 87, 19-24; Piskala et al., in Zorbach and Tipson (eds.) Synthetic Procedures in Nucleic Acid Chemistry, Vol. 1, Wiley Interscience, New York, 1968, 107-108; Piskala, Collect. Czech. Chem. Comm. 1967, 32, 3966-3976.

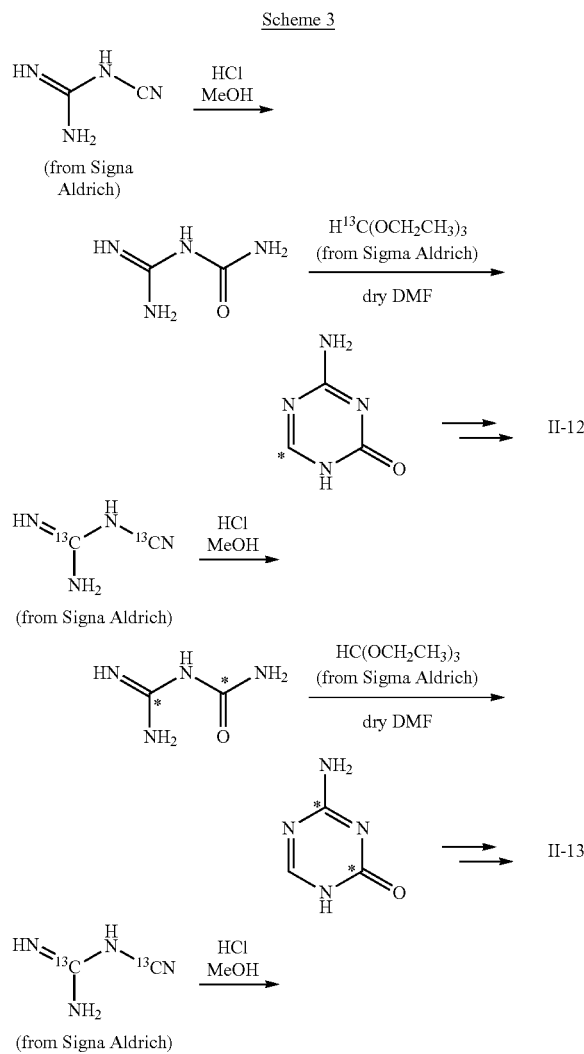

Scheme 3

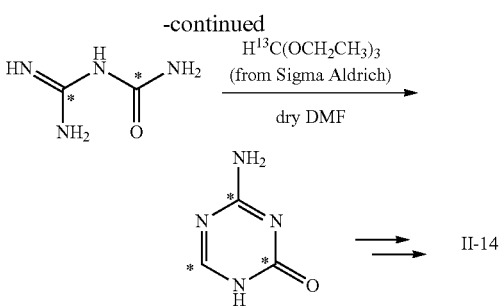

In other embodiments, one or more carbon positions on the 5-azacytosine ring and one or more carbon positions in the ribose portion of 5-azacytidine are enriched with carbon-13. Such 5-azacytidine analogs may be prepared following Scheme 1, coupling a suitable carbon-13-enriched ribose starting materials with a suitable carbon-13-enriched 5-azacytosine. For example, compounds may be prepared from a carbon-13-enriched ribose starting material listed in Table 2, and carbon-13-enriched 5-azacytosine prepared according to Scheme 3.

The routes and methods described above may be modified to provide an isotopolougue of 5-azacytidine having both deuterium enrichment and carbon-13 enrichment.

C. Pharmaceutical Formulations

1. Overview

Embodiments herein encompass pharmaceutical formulations and compositions comprising one or more cytidine analogs, e.g., 5-azacytidine, and optionally a permeation enhancer, wherein the formulations and compositions are prepared for oral administration. In a particular embodiment, the formulations and compositions are prepared for release of the cytidine analog substantially in the stomach. In specific embodiments, the cytidine analogs, e.g., 5-azacytidine, and the pharmaceutical formulations and compositions are used for treating diseases and disorders associated with abnormal cell proliferation, wherein the cytidine analogs, the formulations and compositions are prepared for oral administration, preferably for release of the cytidine analogs substantially in the stomach. Particular embodiments relate to the use of one or more cytidine analogs, e.g., 5-azacytidine, for the preparation of pharmaceutical formulations and compositions for treating particular medical indications, as provided herein. The pharmaceutical formulations and compositions comprising cytidine analogs provided herein are intended for oral delivery of the cytidine analog in subjects in need thereof. Oral delivery formats include, but are not limited to, tablets, capsules, caplets, solutions, suspensions, and syrups, and may also comprise a plurality of granules, beads, powders or pellets that may or may not be encapsulated. Such formats may also be referred to herein as the "drug core" which contains the cytidine analog.

Particular embodiments herein provide solid oral dosage forms that are tablets or capsules. In certain embodiments, the formulation is a tablet comprising a cytidine analog. In certain embodiments, the formulation is a capsule comprising a cytidine analog. In certain embodiments, the tablets or capsules provided herein optionally comprise one or more excipients, such as, for example, glidants, diluents, lubricants, colorants, disintegrants, granulating agents, binding agents, polymers, and coating agents. In certain embodiments, the formulation is an immediate release tablet. In certain embodiments, the formulation is a controlled release tablet releasing the API, e.g., substantially in the stomach. In certain embodiments, the formulation is a hard gelatin capsule. In certain embodiments, the formulation is a soft gelatin capsule. In certain embodiments, the capsule is a hydroxypropyl methylcellulose (HPMC) capsule. In certain embodiments, the formulation is an immediate release capsule. In certain embodiments, the formulation is an immediate or controlled release capsule releasing the API, e.g., substantially in the stomach. In certain embodiments, the formulation is a rapidly disintegrating tablet that dissolves substantially in the mouth following administration. In certain embodiments, embodiments herein encompass the use of cytidine analogs, e.g., 5-azacytidine, for the preparation of a pharmaceutical composition for treating a disease associated with abnormal cell proliferation, wherein the composition is prepared for oral administration.

2. Performance of Certain Dosage Forms Provided Herein

In certain embodiments, the formulations comprising the cytidine analogs, such as, for example, 5-azacytidine, effect an immediate release of the API upon oral administration. In particular embodiments, the formulations comprising the cytidine analogs, such as, for example, 5-azacytidine, comprise a therapeutically or prophylactically effective amount of the cytidine analog (and, optionally, one or more excipients) and effect an immediate release of the API upon oral administration.

In certain embodiments, the formulations comprising the cytidine analogs, such as, for example, 5-azacytidine, effect a controlled release of the API substantially in the stomach upon oral administration. In certain embodiments, the formulations comprising the cytidine analogs, such as, for example, 5-azacytidine, comprise a therapeutically or prophylactically effective amount of the cytidine analog and a drug release controlling component which is capable of releasing the cytidine analog substantially in the stomach. In certain embodiments, matrices (e.g., polymer matrices) may be employed in the formulation to control the release of the cytidine analog. In certain embodiments, coatings and/or shells may be employed in the formulation to control the release of the cytidine analog in the substantially in the stomach.

In certain embodiments, the formulations comprising the cytidine analogs, such as, for example, 5-azacytidine, release the API substantially in the stomach upon oral administration. In certain embodiments, the formulations effect an immediate release of the cytidine analog upon oral administration. In certain embodiments, the formulations optionally further comprises a drug release controlling component, wherein the drug release controlling component is adjusted such that the release of the cytidine analog occurs substantially in the stomach. In particular embodiments, the drug release controlling component is adjusted such that the release of the cytidine analog is immediate and occurs substantially in the stomach. In particular embodiments, the drug release controlling component is adjusted such that the release of the cytidine analog is sustained and occurs substantially in the stomach. In certain embodiments, the formulation of the cytidine analog, such as, for example, 5-azacytidine, releases the API substantially in the stomach, and, subsequently, releases the remainder of the API in the intestine upon oral administration.

Methods by which skilled practitioners can assess where a drug is released in the gastrointestinal tract of a subject are known in the art, and include, for example, scintigraphic studies, testing in a bio-relevant medium which simulates the fluid in relevant portions of the gastrointestinal tract, among other methods.

Particular embodiments herein provide pharmaceutical formulations (e.g., immediate release oral formulations and/or formulations that release the API substantially in the stomach) comprising a cytidine analog (e.g., 5-azacytidine) that achieve a particular exposure in the subject to which the formulation is orally administered, as compared to a SC dose of the same cytidine analog. Particular embodiments provide oral formulations that achieve an exposure of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%, as compared to a SC dose.

In certain embodiments, the formulation (e.g., immediate release oral formulation and/or formulation that release the API substantially in the stomach) comprising the cytidine analog, such as, for example, 5-azacytidine, renders a certain percentage of the cytidine analog in the formulation systemically bioavailable upon oral administration. In certain embodiments, after the subject is orally administered the formulation, the cytidine analog in the formulation is absorbed substantially in the stomach, and becomes available to the body through systemic exposure. In particular embodiments, the oral bioavailability of a formulation comprising a cytidine analog provided herein is, e.g., greater than about 1%, greater than about 5%, greater than about 10%, greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75%, greater than about 80%, greater than about 85%, greater than about 90%, greater than about 95%, or about 100%, of the total amount of the cytidine analog in the formulation.

Methods by which skilled practitioners can assess the oral bioavailability of a drug formulation in a subject are known in the art. Such methods, include, for example, comparing certain dosing-related parameters, such as, but not limited to, maximum plasma concentration ("Cmax"), time to maximum plasma concentration ("Tmax"), or area-under-the-curve ("AUC") determinations.

Particular embodiments herein provide pharmaceutical formulations (e.g., immediate release oral formulations and/or formulations that release the API substantially in the stomach) comprising a cytidine analog (e.g., 5-azacytidine) that achieve a particular AUC value (e.g., AUC(0-t) or AUC(0-∞)) in the subject (e.g., human) to which the formulation is orally administered. Particular embodiments provide oral formulations that achieve an AUC value of at least about 25 ng-hr/mL, at least about 50 ng-hr/mL, at least about 75 ng-hr/mL, at least about 100 ng-hr/mL, at least about 150 ng-hr/mL, at least about 200 ng-hr/mL, at least about 250 ng-hr/mL, at least about 300 ng-hr/mL, at least about 350 ng-hr/mL, at least about 400 ng-hr/mL, at least about 450 ng-hr/mL, at least about 500 ng-hr/mL, at least about 550 ng-hr/mL, at least about 600 ng-hr/mL, at least about 650 ng-hr/mL, at least about 700 ng-hr/mL, at least about 750 ng-hr/mL, at least about 800 ng-hr/mL, at least about 850 ng-hr/mL, at least about 900 ng-hr/mL, at least about 950 ng-hr/mL, at least about 1000 ng-hr/mL, at least about 1100 ng-hr/mL, at least about 1200 ng-hr/mL, at least about 1300 ng-hr/mL, at least about 1400 ng-hr/mL, at least about 1500 ng-hr/mL, at least about 1600 ng-hr/mL, at least about 1700 ng-hr/mL, at least about 1800 ng-hr/mL, at least about 1900 ng-hr/mL, at least about 2000 ng-hr/mL, at least about 2250 ng-hr/mL, or at least about 2500 ng-hr/mL. In particular embodiments, the AUC determination is obtained from a time-concentration pharmacokinetic profile obtained from the blood samples of animals or human volunteers following dosing.

Particular embodiments herein provide pharmaceutical formulations (e.g., immediate release oral formulations and/or formulations that release the API substantially in the stomach) comprising a cytidine analog (e.g., 5-azacytidine) that achieve a particular maximum plasma concentration ("Cmax") in the subject to which the formulation is orally administered. Particular embodiments provide oral formulations that achieve a Cmax of the cytidine analog of at least about 25 ng/mL, at least about 50 ng/mL, at least about 75 ng/mL, at least about 100 ng/mL, at least about 150 ng/mL, at least about 200 ng/mL, at least about 250 ng/mL, at least about 300 ng/mL, at least about 350 ng/mL, at least about 400 ng/mL, at least about 450 ng/mL, at least about 500 ng/mL, at least about 550 ng/mL, at least about 600 ng/mL, at least about 650 ng/mL, at least about 700 ng/mL, at least about 750 ng/mL, at least about 800 ng/mL, at least about 850 ng/mL, at least about 900 ng/mL, at least about 950 ng/mL, at least about 1000 ng/mL, at least about 1100 ng/mL, at least about 1200 ng/mL, at least about 1300 ng/mL, at least about 1400 ng/mL, at least about 1500 ng/mL, at least about 1600 ng/mL, at least about 1700 ng/mL, at least about 1800 ng/mL, at least about 1900 ng/mL, at least about 2000 ng/mL, at least about 2250 ng/mL, or at least about 2500 ng/mL.

Particular embodiments herein provide pharmaceutical formulations (e.g., immediate release oral formulations and/or formulations that release the API substantially in the stomach) comprising a cytidine analog (e.g., 5-azacytidine) that achieve a particular time to maximum plasma concentration ("Tmax") in the subject to which the formulation is orally administered. Particular embodiments provide oral formulations that achieve a Tmax of the cytidine analog of less than about 10 min., less than about 15 min., less than about 20 min., less than about 25 min., less than about 30 min., less than about 35 min., less than about 40 min., less than about 45 min., less than about 50 min., less than about 55 min., less than about 60 min., less than about 65 min., less than about 70 min., less than about 75 min., less than about 80 min., less than about 85 min., less than about 90 min., less than about 95 min., less than about 100 min., less than about 105 min., less than about 110 min., less than about 115 min., less than about 120 min., less than about 130 min., less than about 140 min., less than about 150 min., less than about 160 min., less than about 170 min., less than about 180 min., less than about 190 min., less than about 200 min., less than about 210 min., less than about 220 min., less than about 230 min., or less than about 240 min. In particular embodiments, the Tmax value is measured from the time at which the formulation is orally administered.

Particular embodiments herein provide oral dosage forms comprising a cytidine analog, wherein the oral dosage forms have an enteric coating. Particular embodiments provide a permeable or partly permeable (e.g., "leaky") enteric coating with pores. In particular embodiments, the permeable or partly permeable enteric-coated tablet releases the 5-azacytidine in an immediate release manner substantially in the stomach.

3. Design of Certain Dosage Forms Provided Herein

Provided herein are dosage forms designed to maximize the absorption and/or efficacious delivery of certain cytidine analogs, e.g., 5-azacytidine, upon oral administration, e.g., for release substantially in the stomach. Accordingly, certain embodiments herein provide a solid oral dosage form of a cytidine analog, such as, for example, 5-azacytidine, using pharmaceutical excipients designed for immediate release of the API upon oral administration, e.g., substantially in the stomach. Particular immediate release formulations comprise a specific amount of a cytidine analog and optionally one or more excipients. In certain embodiments, the formulation may be an immediate release tablet or an immediate release capsule (such as, e.g., an HPMC capsule).

Provided herein are methods of making the formulations provided herein comprising the cytidine analogs provided herein (e.g., immediate release oral formulations and/or formulations that release the API substantially in the stomach). In particular embodiments, the formulations provided herein may be prepared using conventional methods known to those skilled in the field of pharmaceutical formulation, as described, e.g., in pertinent textbooks. See, e.g., REMINGTON, THE SCIENCE AND PRACTICE OF PHARMACY, 20th Edition, Lippincott Williams & Wilkins, (2000); ANSEL et al., PHARMACEUTICAL DOSAGE FORMS AND DRUG DELIVERY SYSTEMS, 7th Edition, Lippincott Williams & Wilkins, (1999); GIBSON, PHARMACEUTICAL PREFORMULATION AND FORMULATION, CRC Press (2001).

In particular embodiments, formulations provided herein (e.g., immediate release oral formulations, formulations that release the API substantially in the stomach, or rapidly disintegrating formulations that dissolve substantially in the mouth) comprise a cytidine analog, such as, for example, 5-azacytidine, in a specific amount. In particular embodiments, the specific amount of the cytidine analog in the formulation is, e.g., about 10 mg, about 20 mg, about 40 mg, about 60 mg, about 80 mg, about 100 mg, about 120 mg, about 140 mg, about 160 mg, about 180 mg, about 200 mg, about 220 mg, least about 240 mg, about 260 mg, about 280 mg, about 300 mg, about 320 mg, about 340 mg, about 360 mg, about 380 mg, about 400 mg, about 420 mg, about 440 mg, about 460 mg, about 480 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, about 2500 mg, about 3000 mg, about 4000 mg, or about 5000 mg. In particular embodiments, the specific amount of the cytidine analog in the formulation is, e.g., at least about 10 mg, at least about 20 mg, at least about 40 mg, at least about 60 mg, at least about 80 mg, at least about 100 mg, at least about 120 mg, at least about 140 mg, at least about 160 mg, at least about 180 mg, at least about 200 mg, at least about 220 mg, at least about 240 mg, at least about 260 mg, at least about 280 mg, at least about 300 mg, at least about 320 mg, at least about 340 mg, at least about 360 mg, at least about 380 mg, at least about 400 mg, at least about 420 mg, at least about 440 mg, at least about 460 mg, at least about 480 mg, at least about 500 mg, at least about 600 mg, at least about 700 mg, at least about 800 mg, at least about 900 mg, at least about 1000 mg, at least about 1100 mg, at least about 1200 mg, at least about 1300 mg, at least about 1400 mg, at least about 1500 mg, at least about 1600 mg, at least about 1700 mg, at least about 1800 mg, at least about 1900 mg, at least about 2000 mg, at least about 2100 mg, at least about 2200 mg, at least about 2300 mg, at least about 2400 mg, at least about 2500 mg, at least about 3000 mg, at least about 4000 mg, or at least about 5000 mg.

In certain embodiments, the formulation is a tablet, wherein the tablet is manufactured using standard, art-recognized tablet processing procedures and equipment. In certain embodiments, the method for forming the tablets is direct compression of a powdered, crystalline and/or granular composition comprising the cytidine analog, alone or in combination with one or more excipients, such as, for example, carriers, additives, polymers, or the like. In certain embodiments, as an alternative to direct compression, the tablets may be prepared using wet granulation or dry granulation processes. In certain embodiments, the tablets are molded rather than compressed, starting with a moist or otherwise tractable material. In certain embodiments, compression and granulation techniques are used.

In certain embodiments, the formulation is a capsule, wherein the capsules may be manufactured using standard, art-recognized capsule processing procedures and equipments. In certain embodiments, soft gelatin capsules may be prepared in which the capsules contain a mixture of the cytidine analog and vegetable oil or non-aqueous, water miscible materials such as, for example, polyethylene glycol and the like. In certain embodiments, hard gelatin capsules may be prepared containing granules of the cytidine analog in combination with a solid pulverulent carrier, such as, for example, lactose, saccharose, sorbitol, mannitol, potato starch, corn starch, amylopectin, cellulose derivatives, or gelatin. In certain embodiments, a hard gelatin capsule shell may be prepared from a capsule composition comprising gelatin and a small amount of plasticizer such as glycerol. In certain embodiments, as an alternative to gelatin, the capsule shell may be made of a carbohydrate material. In certain embodiments, the capsule composition may additionally include polymers, colorings, flavorings and opacifiers as required. In certain embodiments, the capsule comprises HPMC.

In certain embodiments, the formulation of the cytidine analog, such as, for example, 5-azacytidine, is prepared using aqueous solvents without causing significant hydrolytic degradation of the cytidine analog. In particular embodiments, the formulation of the cytidine analog, such as, for example, 5-azacytidine, is a tablet which contains a coating applied to the drug core using aqueous solvents without causing significant hydrolytic degradation of the cytidine analog in the formulation. In certain embodiments, water is employed as the solvent for coating the drug core. In certain embodiments, the oral dosage form of the cytidine analog is a tablet containing a film coat applied to the drug core using aqueous solvents. In particular embodiments, water is employed as the solvent for film-coating. In particular embodiments, the tablet containing the cytidine analog is film-coated using aqueous solvents without effecting degradation of the pharmaceutical composition. In particular embodiments, water is used as the film coating solvent without effecting degradation of the pharmaceutical composition. In certain embodiments, an oral dosage form comprising 5-azacytidine and an aqueous film coating effects immediate drug release upon oral delivery. In certain embodiments, the oral dosage form comprising 5-azacytidine and an aqueous film coating effects controlled drug release to the upper gastrointestinal tract, e.g., the stomach, upon oral administration. In particular embodiments, a tablet with an aqueous-based film coating comprises 5-azacytidine as the API.

In certain embodiments, provided herein is a controlled release pharmaceutical formulation for oral administration of a cytidine analog that releases the cytidine analog substantially in the stomach, comprising: a) a specific amount of a cytidine analog; b) a drug release controlling component for controlling the release of the cytidine analog substantially in the upper gastrointestinal tract, e.g., the stomach; and c) optionally one or more excipients. In certain embodiments, the oral dosage form comprising the cytidine analog is prepared as a controlled release tablet or capsule which includes a drug core comprising the pharmaceutical composition and optional excipients. Optionally, a "seal coat" or "shell" is applied. In certain embodiments, a formulation provided herein comprising a cytidine analog provided herein is a controlled release tablet or capsule, which comprises a therapeutically effective amount of the cytidine analog, a drug release controlling component that controls the release of the cytidine analog substantially in the stomach upon oral administration, and optionally, one or more excipients.

Particular embodiments provide a drug release controlling component that is a polymer matrix, which swells upon exposure to gastric fluid to effect the gastric retention of the formulation and the sustained release of the cytidine analog from the polymer matrix substantially in the stomach. In certain embodiments, such formulations may be prepared by incorporating the cytidine analog into a suitable polymeric matrix during formulation. Examples of such formulations are known in the art. See, e.g., Shell et al., U.S. Patent Publication No. 2002/0051820 (application Ser. No. 09/990, 061); Shell et al., U.S. Patent Publication No. 2003/0039688 (application Ser. No. 10/045,823); Gusler et al., U.S. Patent Publication No. 2003/0104053 (application Ser. No. 10/029, 134), each of which is incorporated herein by reference in its entirety.

In certain embodiments, the drug release controlling component may comprise a shell surrounding the drug-containing core, wherein the shell releases the cytidine analog from the core by, e.g., permitting diffusion of the cytidine analog from the core and promoting gastric retention of the formulation by swelling upon exposure to gastric fluids to a size that is retained in the stomach. In certain embodiments, such formulations may be prepared by first compressing a mixture of the cytidine analog and one or more excipients to form a drug core, and compressing another powdered mixture over the drug core to form the shell, or enclosing the drug core with a capsule shell made of suitable materials. Examples of such formulations are known in the art. See, e.g., Berner et al., U.S. Patent Publication No. 2003/0104062 application Ser. No. 10/213,823), incorporated herein by reference in its entirety.

Certain embodiments herein provide oral dosage forms comprising a cytidine analog, wherein the dosage form contains pores in the conventional enteric coating. In particular embodiments, the oral dosage form of the cytidine analog is a tablet that contains a permeable or partly permeable (e.g., "leaky") enteric coating with pores. In particular embodiments, the permeable or partly permeable enteric-coated tablet controls the release of the cytidine analog from the tablet primarily to the upper gastrointestinal tract, e.g., the stomach. In particular embodiments, the permeable or partly permeable enteric-coated tablet comprises 5-azacytidine. In particular embodiments, the remainder of the cytidine analog is subsequently released beyond the stomach (e.g., in the intestine).

In certain embodiments, the pharmaceutical formulation provided herein is a compressed tablet comprising a cytidine analog. In addition to the cytidine analog, the tablet optionally comprises one or more excipients, including (a) diluents or fillers, which may add necessary bulk to a formulation to prepare tablets of the desired size; (b) binders or adhesives, which may promote adhesion of the particles of the formulation, enabling a granulation to be prepared and maintaining the integrity of the final tablet; (c) disintegrants or disintegrating agents, which, after administration, may promote breakup of the tablets to smaller particles for improved drug availability; (d) anti-adherents, glidants, lubricants or lubricating agents, which may enhance flow of the tableting material into the tablet dies, minimize wear of the punches and dies, prevent the sticking of fill material to the punches and dies, and produce tablets having a sheen; and (e) miscellaneous adjuncts such as colorants and flavorants. After compression, tablets provided herein may be coated with various materials as described herein.

In certain embodiments, the pharmaceutical formulation provided herein is a multiple compressed tablet of a cytidine analog. Multiple compressed tablets are prepared by subjecting the fill material to more than a single compression. The result may be a multiple-layered tablet or a tablet-within-a-tablet, the inner tablet being the core comprising a cytidine analog and optionally one or more excipients, and the outer portion being the shell, wherein the shell comprises one or more excipients, and may or may not contain the cytidine analog. Layered tablets may be prepared by the initial compaction of a portion of fill material in a die followed by additional fill material and compression to form two- or three-layered tablets, depending upon the number of separate fills. Each layer may contain a different therapeutic agent, separate from one another for reasons of chemical or physical incompatibility, or the same therapeutic agent for staged drug release, or simply for the unique appearance of the multiple-layered tablet. Each portion of fill may be colored differently to prepare a distinctive looking tablet. In the preparation of tablets having a compressed tablet as the inner core, special machines may be used to place the preformed tablet precisely within the die for the subsequent compression of surrounding fill material.

In certain embodiments, the compressed tablet of a cytidine analog may be coated with a colored or an uncolored sugar layer. The coating may be water-soluble and quickly dissolved after oral ingestion. The sugar coating may serve the purpose of protecting the enclosed drug from the environment and providing a barrier to an objectionable taste or smell. The sugar coating may also enhance the appearance of the compressed tablet and permit the imprinting of identifying manufacturer's information. In certain embodiments, sugar-coated tablets may be 50% larger and heavier than the original uncoated tablets. The sugar-coating of tablets may be divided into the following optional steps: (1) waterproofing and sealing (if needed); (2) sub-coating; (3) smoothing and final rounding; (4) finishing and coloring (if desired); (5) imprinting (if needed); and (6) polishing.

In certain embodiments, the compressed tablet of a cytidine analog may be film-coated. Film-coated tablets may be compressed tablets coated with a thin layer of a polymer capable of forming a skin-like film over the tablet. The film is usually colored and has the advantage to be more durable, less bulky, and less time-consuming to apply. By its composition, the coating may be designed to rupture and expose the core tablet at the desired location within the gastrointestinal tract. The film-coating process, which places a thin skin-tight coating of a plastic-like material over the compressed tablet, may produce coated tablets having essentially the same weight, shape, and size as the originally compressed tablet. The film-coating may be colored to make the tablets attractive and distinctive. Film-coating solutions may be non-aqueous or aqueous. In particular embodiments, the non-aqueous solutions may optionally contain one or more of the following types of materials to provide the desired coating to the tablets: (1) a film former capable of producing smooth, thin films reproducible under conventional coating conditions and applicable to a variety of tablet shapes, such as, for example, cellulose acetate phthalate; (2) an alloying substance providing water solubility or permeability to the film to ensure penetration by body fluids and therapeutic availability of the drug, such as, for example, polyethylene glycol; (3) a plasticizer to produce flexibility and elasticity of the coating and thus provide durability, such as, for example, castor oil; (4) a surfactant to enhance spreadability of the film during application, such as, for example, polyoxyethylene sorbitan derivatives; (5) opaquants and colorants to make the appearance of the coated tablets attractive and distinctive, such as, for example, titanium dioxide as an opaquant, and FD&C or D&C dyes as a colorant; (6) sweeteners, flavors, or aromas to enhance the acceptability of the tablet to the subject, such as, for example, saccharin as sweeteners, and vanillin as flavors and aromas; (7) a glossant to provide a luster to the tablets without a separate polishing operation, such as, for example, beeswax; and (8) a volatile solvent to allow the spread of the other components over the tablets while allowing rapid evaporation to permit an effective yet speedy operation, such as, for example, alcohol-acetone mixture. In certain embodiments, an aqueous film-coating formulation may contain one or more of the following: (1) film-forming polymer, such as, for example, cellulose ether polymers as hydroxypropyl methyl-cellulose, hydroxypropyl cellulose, and methyl-cellulose; (2) plasticizer, such as, for example, glycerin, propylene glycol, polyethylene glycol, diethyl phthalate, and dibutyl subacetate; (3) colorant and opacifier, such as, for example, FD&C or D&C lakes and iron oxide pigments; or (4) vehicle, such as, for example, water.

In certain embodiments, the compressed tablet of a cytidine analog may be compression-coated. The coating material, in the form of a granulation or powder, may be compressed onto a tablet core of drug with a special tablet press.

In certain embodiments, the pharmaceutical formulation is a gelatin-coated tablet of a cytidine analog. A gelatin-coated tablet is a capsule-shaped compressed tablet that allows the coated product to be smaller than a capsule filled with an equivalent amount of powder. The gelatin coating facilitates swallowing and compared to unsealed capsules, gelatin-coated tablets may be more tamper-evident.

In certain embodiments, the pharmaceutical formulation may be a sublingual tablet of a cytidine analog. The sublingual tablet is intended to be dissolved beneath the tongue for absorption through the oral mucosa. The sublingual tablet may dissolve promptly and provide rapid release of the drug.

In certain embodiments, the pharmaceutical formulation is an immediate release tablet of a cytidine analog. In certain embodiments, the immediate release tablet is designed, e.g., to disintegrate and release the API absent of any special rate-controlling features, such as special coatings and other techniques. In certain embodiments, the formulation is a rapidly disintegrating tablet that, e.g., dissolves substantially in the mouth following administration. In certain embodiments, the pharmaceutical formulation is an extended release tablet of a cytidine analog. In certain embodiments, the extended release tablet is designed, e.g., to release the API over an extended period of time and substantially in the stomach.

In certain embodiments, compressed tablets may be prepared by wet granulation. Wet granulation is a widely employed method for the production of compressed tablets, and, in particular embodiments, requires one or more the following steps: (1) weighing and blending the ingredients; (2) preparing a damp mass; (3) screening the damp mass into pellets or granules; (4) drying the granulation; (5) sizing the granulation by dry screening; (6) adding lubricant and blending; and (7) tableting by compression.

In certain embodiments, compressed tablets may be prepared by dry granulation. By the dry granulation method, the powder mixture is compacted in large pieces and subsequently broken down or sized into granules. But this method, either the active ingredient or the diluent has cohesive property. After weighing and mixing the ingredients, the powder mixture may be slugged or compressed into large flat tablets or pellets. The slugs then are broken up by hand or by a mill and passed through a screen of desired mesh for sizing. Lubricant is added in the usual manner, and tablets are prepared by compression. Alternatively, instead of slugging, powder compactors may be used to increase the density of a powder by pressing it between high-pressure rollers. The compressed material then is broken up, sized, and lubricated, and tablets are prepared by compression in the usual manner. The roller compaction method is often preferred over slugging. Binding agents used in roller compaction formulations include methylcellulose or hydroxylmethylcellulose and can produce good tablet hardness and friability.

In certain embodiments, compressed tablets may be prepared by direct compression. Some granular chemicals possess free flowing and cohesive properties that enable them to be compressed directly in a tablet machine without the need of wet or dry granulation. For chemicals that do not possess this quality, special pharmaceutical excipients may be used which impart the necessary qualities for the production of tablets by direct compression. Particular tableting excipients include, e.g.: fillers, such as spray-dried lactose, micro-crystals of alpha-monohydrate lactose, sucrose-invert sugar-corn starch mixtures, micro-crystalline cellulose, crystalline maltose, and di-calcium phosphate; disintegrating agents, such as direct-compression starch, sodium carboxymethyl starch, cross-linked carboxymethylcellulose fibers, and cross-linked polyvinylpyrrolidone; lubricants, such as magnesium stearate and talc; and glidants, such as fumed silicon dioxide.

In certain embodiments, tablets provided herein may be prepared by molding. The base for molded tablets is generally a mixture of finely powdered lactose with or without a portion of powdered sucrose. In preparing the fill, the drug is mixed uniformly with the base by geometric dilution. The powder mixture may be wetted with a mixture of water and alcohol sufficient only to dampen the powder so that it may be compacted. The solvent action of the water on a portion of the lactose/sucrose base effects the biding of the powder mixture upon drying. The alcohol portion hastens the drying process.

In certain embodiments, the pharmaceutical formulations provided herein contain the cytidine analog and, optionally, one or more excipients to form a "drug core." Optional excipients include, e.g., diluents (bulking agents), lubricants, disintegrants, fillers, stabilizers, surfactants, preservatives, coloring agents, flavoring agents, binding agents, excipient supports, glidants, permeation enhancement excipients, plasticizers and the like, e.g., as known in the art. It will be understood by those in the art that some substances serve more than one purpose in a pharmaceutical composition. For instance, some substances are binders that help hold a tablet together after compression, yet are also disintegrants that help break the tablet apart once it reaches the target delivery site. Selection of excipients and amounts to use may be readily determined by the formulation scientist based upon experience and consideration of standard procedures and reference works available in the art.

In certain embodiments, formulations provided herein comprise one or more binders. Binders may be used, e.g., to impart cohesive qualities to a tablet, and thus ensure that the tablet remains intact after compression. Suitable binders include, but are not limited to, starch (including corn starch and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone, cellulosic polymers (including hydroxypropyl cellulose, hydroxypropylmethylcellulose, methyl cellulose, ethyl cellulose, hydroxyethyl cellulose, carboxymethyl cellulose and the like), veegum, carbomer (e.g., CARBOPOL), sodium, dextrin, guar gum, hydrogenated vegetable oil, magnesium aluminum silicate, maltodextrin, polymethacrylates, povidone (e.g., KOLLIDON, PLASDONE), microcrystalline cellulose, among others. Binding agents also include, e.g., acacia, agar, alginic acid, cabomers, carrageenan, cellulose acetate phthalate, *ceratonia*, chitosan, confectioner's sugar, copovidone, dextrates, dextrin, dextrose, ethylcellulose, gelatin, glyceryl behenate, guar gum, hydroxyethyl cellulose, hydroxyethylmethyl cellulose, hydroxypropyl cellulose, hydroxypropyl starch, hypromellose, inulin, lactose, magnesium aluminum silicate, maltodextrin, maltose, methylcellulose, poloxamer, polycarbophil, polydextrose, polyethylene oxide, polymethylacrylates, povidone, sodium alginate, sodium carboxymethylcellulose, starch, pregelatinized starch, stearic acid, sucrose, and zein. The binding agent can be, relative to the drug core, in the amount of about 2% w/w of the drug core; about 4% w/w of the drug core, about 6% w/w of the drug core, about 8% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, about 34% w/w of the drug core, about 36% w/w of the drug core, about 38% w/w of the drug core, about 40% w/w of the drug core, about 42% w/w of the drug core, about 44% w/w of the drug core, about 46% w/w of the drug core, about 48% w/w of the drug core, about 50% w/w of the drug core, about 52% w/w of the drug core, about 54% w/w of the drug core, about 56% w/w of the drug core, about 58% w/w of the drug core, about 60% w/w of the drug core, about 62% w/w of the drug core, about 64% w/w of the drug core, about 66% w/w of the drug core; about 68% w/w of the drug core, about 70% w/w of the drug core, about 72% w/w of the drug core, about 74% w/w of the drug core, about 76% w/w of the drug core, about 78% w/w of the drug core, about 80% w/w of the drug core, about 82% w/w of the drug core, about 84% w/w of the drug core, about 86% w/w of the drug core, about 88% w/w of the drug core, about 90% w/w of the drug core, about 92% w/w of the drug core, about 94% w/w of the drug core, about 96% w/w of the drug core, about 98% w/w of the drug core, or more, if determined to be appropriate. In certain embodiments, a suitable amount of a particular binder is determined by one of ordinary skill in the art.

In certain embodiments, formulations provided herein comprise one or more diluents. Diluents may be used, e.g., to increase bulk so that a practical size tablet is ultimately provided. Suitable diluents include dicalcium phosphate, calcium sulfate, lactose, cellulose, kaolin, mannitol, sodium chloride, dry starch, microcrystalline cellulose (e.g., AVICEL), microfine cellulose, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT), potassium chloride, sodium chloride, sorbitol and talc, among others. Diluents also include, e.g., ammonium alginate, calcium carbonate, calcium phosphate, calcium sulfate, cellulose acetate, compressible sugar, confectioner's sugar, dextrates, dextrin, dextrose, erythritol, ethylcellulose, fructose, fumaric acid, glyceryl palmitostearate, isomalt, kaolin, lacitol, lactose, mannitol, magnesium carbonate, magnesium oxide, maltodextrin, maltose, medium-chain triglycerides, microcrystalline cellulose, microcrystalline silicified cellulose, powered cellulose, polydextrose, polymethylacrylates, simethicone, sodium alginate, sodium chloride, sorbitol, starch, pregelatinized starch, sucrose, sulfobutylether-β-cyclodextrin, talc, tragacanth, trehalose, and xylitol. Diluents may be used in amounts calculated to obtain a desired volume for a tablet or capsule; in certain embodiments, a diluent is used in an amount of about 5% or more, about 10% or more, about 15% or more, about 20% or more, about 22% or more, about 24% or more, about 26% or more, about 28% or more, about 30% or more, about 32% or more, about 34% or more, about 36% or more, about 38% or more, about 40% or more, about 42% or more, about 44% or more, about 46% or more, about 48% or more, about 50% or more, about 52% or more, about 54% or more, about 56% or more, about 58% or more, about 60% or more, about 62% or more, about 64% or more, about 68% or more, about 70% ore more, about 72% or more, about 74% or more, about 76% or more, about 78% or more, about 80% or more, about 85% or more, about 90% or more, or about 95% or more, weight/weight, of a drug core; between about 10% and about 90% w/w of the drug core; between about 20% and about 80% w/w of the drug core; between about 30% and about 70% w/w of the drug core; between about 40% and about 60% w/w of the drug core. In certain embodiments, a suitable amount of a particular diluent is determined by one of ordinary skill in the art.

In certain embodiments, formulations provided herein comprise one or more lubricants. Lubricants may be used, e.g., to facilitate tablet manufacture; examples of suitable lubricants include, for example, vegetable oils such as peanut oil, cottonseed oil, sesame oil, olive oil, corn oil, and oil of theobroma, glycerin, magnesium stearate, calcium stearate, and stearic acid. In certain embodiments, stearates, if present, represent no more than approximately 2 weight % of the drug-containing core. Further examples of lubricants include, e.g., calcium stearate, glycerin monostearate, glyceryl behenate, glyceryl palmitostearate, magnesium lauryl sulfate, magnesium stearate, myristic acid, palmitic acid, poloxamer, polyethylene glycol, potassium benzoate, sodium benzoate, sodium chloride, sodium lauryl sulfate, sodium stearyl fumarate, stearic acid, talc, and zinc stearate. In particular embodiments, the lubricant is magnesium stearate. In certain embodiments, the lubricant is present, relative to the drug core, in an amount of about 0.2% w/w of the drug core, about 0.4% w/w of the drug core, about 0.6% w/w of the drug core, about 0.8% w/w of the drug core, about 1.0% w/w of the drug core, about 1.2% w/w of the drug core, about 1.4% w/w of the drug core, about 1.6% w/w of the drug core, about 1.8% w/w of the drug core, about 2.0% w/w of the drug core, about 2.2% w/w of the drug core, about 2.4% w/w of the drug core, about 2.6% w/w of the drug core, about 2.8% w/w of the drug core, about 3.0% w/w of the drug core, about 3.5% w/w of the drug core, about 4% w/w of the drug core, about 4.5% w/w of the drug core, about 5% w/w of the drug core, about 6% w/w of the drug core, about 7% w/w of the drug core, about 8% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 25% w/w of the drug core, about 30% w/w of the drug core, about 35% w/w of the drug core, about 40% w/w of the drug core, between about 0.2% and about 10% w/w of the drug core, between about 0.5% and about 5% w/w of the drug core, or between about 1% and about 3% w/w of the drug core. In certain embodiments, a suitable amount of a particular lubricant is determined by one of ordinary skill in the art.

In certain embodiments, formulations provided herein comprise one or more disintegrants. Disintegrants may be used, e.g., to facilitate disintegration of the tablet, and may be, e.g., starches, clays, celluloses, algins, gums or cross-linked polymers. Disintegrants also include, e.g., alginic acid, carboxymethylcellulose calcium, carboxymethylcellulose sodium (e.g., AC-DI-SOL, PRIMELLOSE), colloidal silicon dioxide, croscarmellose sodium, crospovidone (e.g., KOLLIDON, POLYPLASDONE), guar gum, magnesium aluminum silicate, methyl cellulose, microcrystalline cellulose, polacrilin potassium, powdered cellulose, pregelitinized starch, sodium alginate, sodium starch glycolate (e.g., EXPLOTAB) and starch. Additional disintegrants include, e.g., calcium alginate, chitosan, sodium docusate, hydroxypropyl cellulose, and povidone. In certain embodiments, the disintegrant is, relative to the drug core, present in the amount of about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, greater than about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular disintegrant is determined by one of ordinary skill in the art.

In certain embodiments, formulations provided herein comprise one or more stabilizers. Stabilizers (also called absorption enhancers) may be used, e.g., to inhibit or retard drug decomposition reactions that include, by way of example, oxidative reactions. Stabilizing agents include, e.g., d-Alpha-tocopheryl polyethylene glycol 1000 succinate (Vitamin E TPGS), acacia, albumin, alginic acid, aluminum stearate, ammonium alginate, ascorbic acid, ascorbyl palmitate, bentonite, butylated hydroxytoluene, calcium alginate, calcium stearate, calcium carboxymethylcellulose, carrageenan, ceratonia, colloidal silicon dioxide, cyclodextrins, diethanolamine, edetates, ethylcellulose, ethyleneglycol palmitostearate, glycerin monostearate, guar gum, hydroxypropyl cellulose, hypromellose, invert sugar, lecithin, magnesium aluminum silicate, monoethanolamine, pectin, poloxamer, polyvinyl alcohol, potassium alginate, potassium polacrilin, povidone, propyl gallate, propylene glycol, propylene glycol alginate, raffinose, sodium acetate, sodium alginate, sodium borate, sodium carboxymethyl cellulose, sodium stearyl fumarate, sorbitol, stearyl alcohol, sulfobutyl-b-cyclodextrin, trehalose, white wax, xanthan gum, xylitol, yellow wax, and zinc acetate. In certain embodiments, the stabilizer is, relative to the drug core, present in the amount of about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular stabilizer is determined by one of ordinary skill in the art.

In certain embodiments, formulations provided herein comprise one or more glidants. Glidants may be used, e.g., to improve the flow properties of a powder composition or granulate or to improve the accuracy of dosing. Excipients that may function as glidants include, e.g., colloidal silicon dioxide, magnesium trisilicate, powdered cellulose, starch, tribasic calcium phosphate, calcium silicate, powdered cellulose, colloidal silicon dioxide, magnesium silicate, magnesium trisilicate, silicon dioxide, starch, tribasic calcium phosphate, and talc. In certain embodiments, the glidant is, relative to the drug core, present in the amount of less than about 1% w/w of the drug core, about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular glidant is determined by one of ordinary skill in the art.

In certain embodiments, formulations provided herein comprise one or more permeation enhancers (also called, e.g., permeability enhancers). In certain embodiments, the permeation enhancer enhances the uptake of a cytidine analog through the gastrointestinal wall (e.g., the stomach). In certain embodiments, the permeation enhancer alters the rate and/or amount of the cytidine analog that enters the bloodstream. In particular embodiments, d-alpha-tocopheryl polyethylene glycol-1000 succinate (Vitamin E TPGS) is used as a permeation enhancer. In particular embodiments, one or more other suitable permeation enhancers are used, including, e.g., any permeation enhancer known in the art. Specific examples of suitable permeation enhancers include, e.g., those listed below:

| Product name | Chemical Name | Example of Supplier |
|---|---|---|
| PLURONIC F 127 | Poloxamer F 127 | Sigma |
| LUTROL F 68 | Poloxamer 188 | BASF |
| CARBOPOL 934-P | Carbomer 934-P | Spectrum Chemical |
| TWEEN 80 | Polysorbate 80 | Sigma |
| Chitosan | Chitosan Low Mol Wt | Aldrich |
| Capric acid/Na salt | Sodium Decanoate | Sigma |
| Lauric acid/Na salt | Sodium Dodecanoate | Sigma |
| Disodium EDTA | Ethylenediamine tetraacetic acid disodium dihydrate | Sigma |
| Propylene glycol | 1,2 Propanediol | Sigma |
| CM Cellulose | Carboxymethyl Cellulose | Sigma |
| LABRASOL | Caprylocaproyl macrogol-8 glycerides | Gattefosse |
| N,N-Dimethylacetamide | (minimum 99%) | Sigma |
| Vitamin E TPGS | d-Alpha-Tocopheryl Polyethylene Glycol-1000 Succinate | Eastman |
| SOLUTOL HS 15 | Polyethylene glycol 660 12-hydroxystearate | BASF |
| LABRAFIL M 1944 CS (2) | Oleyl Macrogolglyerides | Gattefosse |

Other potential permeation enhancers include, e.g., alcohols, dimethyl sulfoxide, glyceryl monooleate, glycofurol, isopropyl myristate, isopropyl palmitate, lanolin, linoleic acid, myristic acid, oleic acid, oleyl alcohol, palmitic acid, polyoxyethylene alkyl ethers, 2-pyrrolidone, sodium lauryl sulfate, and thymol.

In certain embodiments, the permeation enhancer is present in the formulation in an amount by weight, relative to the total weight of the formulation, of about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1% about 4.2%, about 4.3%, about 4.4%, about 4.5%, about 4.6%, about 4.7%, about 4.8%, about 4.9%, about 5%, about 5.1% about 5.2%, about 5.3%, about 5.4%, about 5.5%, about 5.6%, about 5.7%, about 5.8%, about 5.9%, about 6%, about 6.1% about 6.2%, about 6.3%, about 6.4%, about 6.5%, about 6.6%, about 6.7%, about 6.8%, about 6.9%, about 7%, about 7.1% about 7.2%, about 7.3%, about 7.4%, about 7.5%, about 7.6%, about 7.7%, about 7.8%, about 7.9%, about 8%, about 8.1% about 8.2%, about 8.3%, about 8.4%, about 8.5%, about 8.6%, about 8.7%, about 8.8%, about 8.9%, about 9%, about 9.1% about 9.2%, about 9.3%, about 9.4%, about 9.5%, about 9.6%, about 9.7%, about 9.8%, about 9.9%, about 10%, greater than about 10%, greater than about 12%, greater than about 14%, greater than about 16%, greater than about 18%, greater than about 20%, greater than about 25%, greater than about 30%, greater than about 35%, greater than about 40%, greater than about 45%, or greater than about 50%. In certain embodiments, the appropriate amount of a suitable permeation enhancer provided herein is determined by one of skill in the art.

Without intending to be limited to any particular theory, the permeation enhancers provided herein may function by, inter alia, facilitating (e.g., increasing the rate or extent of) the transport of a cytidine analog through the gastrointestinal wall. In general, movement through the gastrointestinal wall may occur by, e.g.: passive diffusion, such as the movement of drug across a membrane in a manner driven solely by the concentration gradient; carrier-mediated diffusion, such as the movement of drug across a cell membrane via a specialized transport system embedded in the cell membrane; paracellular diffusion, such as the movement of a drug across a membrane by going between, rather than through, two cells; and transcellular diffusion, such as the movement of a drug across the cell. Additionally, there are numerous cellular proteins capable of preventing intracellular accumulation of drugs by pumping out drug that enters the cell. These are sometimes called efflux pumps. One such efflux pump is that involving p-glycoprotein, which is present in many different tissues in the body (e.g., intestine, placental membrane, blood-brain barrier). Permeation enhancers can function by, inter alia, facilitating any of the processes mentioned above (such as by increasing fluidity of membranes, opening tight junctions between cells, and/or inhibiting efflux, among others).

In certain embodiments, the compositions provided herein comprising a cytidine analog, e.g., 5-azacytidine, are essentially free of a cytidine deaminase inhibitor (e.g., do not comprise a cytidine deaminase inhibitor). In certain embodiments, the compositions provided herein are essentially free of (e.g., do not comprise) the cytidine deaminase inhibitor tetrahydrouridine (THU). Certain embodiments herein provide pharmaceutical compositions comprising a therapeutically effective amount of a cytidine analog (e.g., 5-azacytidine), wherein the compositions release the cytidine analog substantially in the stomach following oral administration to a subject, and wherein the compositions are essentially free of (e.g., do not comprise) a cytidine deaminase inhibitor (e.g., THU). Certain embodiments herein provide pharmaceutical compositions comprising a therapeutically effective amount of a cytidine analog (e.g., 5-azacytidine), wherein the compositions release the cytidine analog substantially in the stomach following oral administration to a subject, wherein the compositions are essentially free of (e.g., do not comprise) a cytidine deaminase inhibitor (e.g., THU), and wherein the compositions achieve a particular biological parameter provided herein (e.g., a particular Cmax value, Tmax value, and/or AUC value provided herein). In particular embodiments, a composition provided herein that is essentially free of a cytidine deaminase inhibitor (e.g., THU) comprises, e.g., less than 200 mg, less than 150 mg, less than 100 mg, less than 50 mg, less than 25 mg, less than 10 mg, less than 5 mg, less than 1 mg, or less than 0.1 mg of the cytidine deaminase inhibitor.

4. Additional Therapeutic Agents

In particular embodiments, the cytidine analog oral formulations provided herein further comprise one, two, three, or more other pharmacologically active substances (also termed herein "additional therapeutic agents," "second active agents," or the like). In particular embodiments, the oral formulations provided herein comprise the additional therapeutic agent(s) in a therapeutically effective amount. In particular embodiments, the cytidine analog (e.g., azacitidine) and the additional therapeutic agent(s) are co-formulated together in the same dosage form using methods of co-formulating active pharmaceutical ingredients, including methods disclosed herein and methods known in the art. In other embodiments, the cytidine analog and the additional therapeutic agent(s) are co-administered in separate dosage forms. It is believed that certain combinations work synergistically in the treatment of particular diseases or disorders, including, e.g., types of cancer and certain diseases and conditions associated with, or characterized by, undesired angiogenesis or abnormal cell proliferation. Cytidine analog oral dosage forms provided herein can also work to alleviate adverse effects associated with certain second active agents, and some second active agents can be used to alleviate adverse effects associated with cytidine analog oral dosage forms provided herein. In certain embodiments, the oral formulations provided herein are co-administered with one or more therapeutic agents to provide a resensitization effect in subjects in need thereof. Additional therapeutic agents can be, e.g., large molecules (e.g., proteins) or small molecules (e.g., synthetic inorganic, organometallic, or organic molecules).

Examples of particular additional therapeutic agents useful in the compositions and methods disclosed herein include, but are not limited to, e.g., cytotoxic agents, antimetabolites, antifolates, histone deacetylase (HDAC) inhibitors (e.g., entinostat, also known as SNDX-275 or MS-275; or vorinostat, also known as suberoylanilide hydroxamic acid (SAHA) or N-hydroxy-N-phenyl-octanediamide), DNA intercalating agents, DNA cross-linking agents, DNA alkylating agents, DNA cleaving agents, topoisomerase inhibitors, cyclin-dependent kinase (CDK) inhibitors, Janus kinase (JAK) inhibitors, anti-angiogenic agents, breakpoint cluster region-Abelson (Bcr-Abl) inhibitors, human epidermal growth factor receptor 2 (HER2) inhibitors, epidermal growth factor receptor (EGFR) inhibitors, vascular endothelial growth factor receptor (VEGFR) inhibitors, platelet-derived growth factor receptor (PDGFR) inhibitors, hepatocyte growth factor receptor (HGFR) inhibitors, insulin-like growth factor receptor (IGFR) inhibitors, tyrosine-protein kinase Kit (c-Kit) inhibitors, renin-angiotensin system (Ras) pathway inhibitors, phosphoinositide 3-kinase (PI3K) inhibitors, multi-targeted kinase inhibitors, mammalian target of rapamycin (mTOR) inhibitors, anti-estrogens, anti-androgens, aromatase inhibitors, somatostatin analogs, estrogen receptor (ER) modulators, anti-tubulin agents, vinca alkaloids, taxanes, heat shock protein (HSP) inhibitors, Smoothened antagonists, telomerase inhibitors, cyclooxygenase-2 (COX-2) inhibitors, anti-metastatic agents, immunosuppressants, biologics such as antibodies, and hormonal therapies. In particular embodiments, the co-administered therapeutic agent is an immunomodulatory compound, e.g., thalidomide, lenalidomide, or pomalidomide. The co-administered agent may be dosed, e.g., orally or by injection.

Other examples of additional therapeutic agents include, but are not limited to, hematopoietic growth factor, a cytokine, an anti-cancer agent, granulocyte colony-stimulating factor (G-CSF), granulocyte-macrophage colony-stimulating factor (GM-CSF), erythropoietin (EPO), interleukin (IL), interferon (IFN), oblimersen, melphalan, topotecan, pentoxifylline, taxotere, irinotecan, ciprofloxacin, doxorubicin, vincristine, dacarbazine, Ara-C, vinorelbine, prednisone, cyclophosphamide, bortezomib, arsenic trioxide. Such additional therapeutic agents are particularly useful in methods and compositions disclosed herein including, but not limited to, those relating to treatment of multiple myeloma.

Other examples of additional therapeutic agents include, but are not limited to, an antibody (e.g., rituximab, anti-CD33), hematopoietic growth factor, cytokine, anti-cancer agent, antibiotic, cox-2 inhibitor, immunomodulatory agent, immunosuppressive agent, corticosteroid, or a pharmacologically active mutant or derivative thereof. See, e.g., S. Nand et al., Leukemia and Lymphoma, 2008, 49(11):2141-47 (describing a Phase II study involving the administration of a combination of hydroxyurea, azacitidine and low dose gemtuzumab ozogamicin to elderly patients with AML and high-risk MDS, and concluding that this combination appears to be a safe and effective regimen in the treatment of AML and high risk MDS in this group of patients). Such additional therapeutic agents are particularly useful in methods and compositions disclosed herein including, but not limited to, those relating to treatment of the diseases and disorders disclosed herein.

Examples of large molecule active agents include, but are not limited to, hematopoietic growth factors, cytokines, and monoclonal and polyclonal antibodies. Typical large molecule active agents are biological molecules, such as naturally occurring or artificially made proteins. Proteins that are particularly useful include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

Particular proteins that can be used in the methods and compositions provided herein include, but are not limited to: filgrastim, which is sold in the United States under the trade name NEUPOGEN® (Amgen, Thousand Oaks, Calif.); sargramostim, which is sold in the United States under the trade name LEUKINE® (Immunex, Seattle, Wash.); and recombinant EPO, which is sold in the United States under the trade name EPOGEN® (Amgen, Thousand Oaks, Calif.).

Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; all of which are incorporated herein by reference.

Embodiments herein encompass the use of native, naturally occurring, and recombinant proteins. Particular embodiments encompass mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., J. Immunol. Methods 248:91-101 (2001).

Antibodies that can be used in combination with oral formulations disclosed herein include monoclonal and polyclonal antibodies. Examples of antibodies include, but are not limited to, trastuzumab (HERCEPTIN®), rituximab (RITUXAN®), bevacizumab (AVASTIN™), pertuzumab (OMNITARG™), tositumomab (BEXXAR®), edrecolomab (PANOREX®), and G250. Oral formulations disclosed herein can also comprise, be combined with, or used in combination with anti-TNF-α antibodies.

Large molecule active agents may be administered in the form of anti-cancer vaccines. For example, vaccines that secrete, or cause the secretion of, cytokines such as IL-2, G-CSF, and GM-CSF can be used in the methods, pharmaceutical compositions, and kits provided herein. See, e.g., Emens, L. A., et al., Curr. Opinion Mol. Ther. 3(1):77-84 (2001).

In one embodiment, the additional therapeutic agent (e.g., large-molecule compound or small-molecule compound) reduces, eliminates, or prevents an adverse effect associated with the administration (e.g., oral administration) of a cytidine analog provided herein. Depending on the particular cytidine analog and the disease or disorder begin treated, adverse effects can include, but are not limited to, anemia, neutropenia, febrile neutropenia, thrombocytopenia, hepatotoxicity (e.g., including, but not limited to, hepatoxicity in patients with preexisting hepatic impairment), elevated serum creatinine, renal failure, renal tubular acidosis, hypokalemia, hepatic coma, nausea, vomiting, dyspepsia, abdominal pain, pyrexia, leukopenia, diarrhea, constipation, ecchymosis, petechiae, rigors, weakness, pneumonia, anxiety, insomnia, lethargy, and decrease in weight, among others known in the art to be associated with particular cytidine analogs.

Like some large molecules, many small-molecule compounds are believed to be capable of providing a synergistic effect when administered with (e.g., before, after or simultaneously) a cytidine analog oral formulation disclosed herein. Examples of small molecule second active agents include, but are not limited to, anti-cancer agents, antibiotics, immunosuppressive agents, and steroids.

Examples of anti-cancer agents include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; acute lymphoblastic leukemia-tyrosine kinase (ALL-TK) antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; 1-beta-D-arabinofuranosylcytosine 5'-diphosphate-rac-1-S-octadecyl-2-O-palmitoyl-1-thioglycerol (ara-CDP-DL-PTBA); arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; basic fibroblast growth factor (bFGF) inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3™; CARN 700 (Carrington Laboratories compound 700); cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; macrophage migration inhibitory factor (MIF) inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; rapidly accelerated fibrosarcoma (raf) antagonists; raltitrexed; ramosetron; ras farnesyl protein transferase inhibitors; ras inhibitors; renin-angiotensin system-GTPase-activating protein (ras-GAP) inhibitor; retelliptine demethylated; rhenium Re 186 etidronate; rhizoxin; ribozymes; RII retinamide; rohitukine; romurtide; roquinimex; rubiginone B 1; ruboxyl; safingol; saintopin; sarcosinamide chloroethylnitrosourea (SarCNU); sarcophytol A; sargramostim; senescent cell-derived inhibitor (Sdi) 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; ubiquitin C (UBC) inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific additional therapeutic agents include, but are not limited to, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

D. Methods of Use

As described herein, certain embodiments herein provide oral formulations of cytidine analogs useful in methods relating to, e.g., permitting different dosing amounts and/or dosing periods; providing alternative pharmacokinetic profiles, pharmacodynamic profiles, and/or safety profiles; permitting the evaluation of long-term and/or maintenance therapies; providing treatment regimens that maximize demethylation and/or gene re-expression; providing treatment regimens that prolong continuous demethylation; providing new indications for cytidine analogs; and/or providing other potential advantageous benefits.

Provided herein are methods of treating patho-physiological conditions manifested by abnormal cell proliferation, such as, for example, cancer, including hematological disorders and solid tumors, by orally administering a pharmaceutical formulation comprising a cytidine analog, such as, for example, 5-azacytidine, wherein the formulation releases the cytidine analog substantially in the stomach. Other embodiments herein provide methods of treating immune disorders. In particular embodiments, the methods provided herein involve oral administering a formulation that effects an immediate release of the cytidine analog. In certain embodiments, the cytidine analog and one or more therapeutic agents are co-administered to subjects to yield a synergistic therapeutic effect. The co-administered agent may be a cancer therapeutic agent dosed orally or by injection.

In certain embodiments, methods provided herein for treating disorders related to abnormal cell proliferation comprise orally administering a formulation comprising a therapeutically effective amount of a cytidine analog. Particular therapeutic indications relating to the methods provided herein are disclosed herein. In certain embodiments, the therapeutically effective amount of the cytidine analog in the pharmaceutical formulation is an amount as disclosed herein. In certain embodiments, the precise therapeutically effective amount of the cytidine analog in the pharmaceutical formulation will vary depending on, e.g., the age, weight, disease and/or condition of the subject.

In particular embodiments, the disorders related to abnormal cell proliferation include, but are not limited to, MDS, AML, ALL, CML, leukemia, chronic lymphocytic leukemia (CLL), lymphoma (including non-Hodgkin's lymphoma (NHL) and Hodgkin's lymphoma), multiple myeloma (MM), sarcoma, melanoma, carcinoma, adenocarcinoma, chordoma, breast cancer, colorectal cancer, ovarian cancer, lung cancer (e.g., non-small-cell lung cancer and small-cell lung cancer), testicular cancer, renal cancer, pancreatic cancer, bone cancer, gastric cancer, head and neck cancer, and prostate cancer. In particular embodiment, the disorder related to abnormal cell proliferation is MDS. In particular embodiments, the disorder related to abnormal cell proliferation is AML.

In certain embodiments, methods provided herein for treating disorders of abnormal cell proliferation comprise administering a cytidine analog using at least two of IV, SC and oral administration methods. For example, particular embodiments herein provide administering an initial treatment cycle of a cytidine analog, such as, for example, 5-azacytidine, administered either SC or IV, followed by subsequent orally administered treatment cycles of the cytidine analog. In certain embodiments, treatment cycles comprise multiple doses administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, or greater than 14 days). Particular embodiments herein provide a treatment schedule comprising SC and/or IV administration for one, two, three, four, five, or more initial cycles, followed by oral administration for subsequent cycles. For example, particular embodiments herein provide a treatment schedule comprising SC administration for cycle 1, followed by oral administration for subsequent cycles. Suitable dosage ranges and amounts for the methods provided herein are provided throughout the specification. For example, in certain embodiments, the SC dose is about 75 mg/m$^2$. In certain embodiments, the oral dose is about 60 mg, about 80 mg, about 120 mg, about 180 mg, about 240 mg, about 300 mg, about 360 mg, about 480 mg, or greater than about 480 mg. In certain embodiments, oral doses are calculated to achieve 80%, 100%, or 120% of SC AUC.

In certain embodiments, methods of treating disorders of abnormal cell proliferation comprises orally administering a formulation comprising a cytidine analog (e.g., 5-azacytidine) as single or multiple daily doses. In particular embodiments, the formulation(s) comprising the cytidine analog is/are orally administered once per day, twice per day, three times per day, four times per day, or more than four times per day. For example, in certain embodiments, the formulation comprising the cytidine analog is administered using a treatment cycle comprising administration of about 200 mg, about 300 mg, about 400 mg, about 500 mg, about 600 mg, about 700 mg, about 800 mg, about 900 mg, or about 1,000 mg of the cytidine analog once, twice, three, or four times per day for 7, 8, 9, 10, 11, 12, 13, 14, 15, 16, 17, 18, 19, 20, 21, 22, 23, 24, 25, 26, 27, 28, 29, or 30 days. In certain embodiments, the method of treating comprises continuous low-dose administration. In certain embodiments, the formulation comprising the cytidine analog is administered using a treatment cycle comprising administration of about 300 mg of the cytidine analog twice per day for 7 days. In certain embodiments, the formulation comprising the cytidine analog is administered using a treatment cycle comprising administration of about 300 mg of the cytidine analog twice per day for 14 days. In certain embodiments, the formulation comprising the cytidine analog is administered using a treatment cycle comprising administration of about 300 mg of the cytidine analog three times per day for 7 days. In certain embodiments, the formulation comprising the cytidine analog is administered using a treatment cycle comprising administration of about 300 mg of the cytidine analog three times per day for 14 days. In certain embodiments, methods provided herein comprise administering a formulation comprising a cytidine analog using one or more of the cycles provided herein, and repeating one or more of the cycles for a period of, e.g., 1, 2, 3, 4, 5, 6, 7, 8, 9, 10, 11, 12, or greater than 12 months.

In certain embodiments, methods herein comprise administering particular oral formulations provided herein to, e.g., overcome limitations associated with IV or SC administration of cytidine analogs. For example, IV or SC administration may limit the ability to deliver a cytidine analog for longer periods of time on a regular basis, thereby potentially limiting the maximal efficacy of the cytidine analog. Due to the difficulties of complying with the rigors of a prolonged IV or SC dosing schedule, prolonged SC or IV exposure to a cytidine analog may cause subjects (e.g., subjects with multiple cytopenias) to discontinue from the regimen. See, e.g., Lyons, R. M., et al., Hematologic Response to Three Alternative Dosing Schedules of Azacitidine in Patients With Myelodysplastic Syndromes, *J. Clin. Oncol.* (2009) (DOI:10.1200/JCO.2008.17.1058), which is incorporated by reference herein in its entirety. Accordingly, in certain embodiments, methods provided herein comprise administering an oral formulation provided herein to overcome these or other limitations associated with SC or IV cytidine analog administration. For example, in certain embodiments, methods provided herein comprise administering daily to a subject an oral formulation provided herein for 7 or more, 8 or more, 9 or more, 10 or more, 11 or more, 12 or more, 13 or more, 14 or more, 15 or more, 16 or more, 17 or more, 18 or more, 19 or more, 20 or more, or 21 or more days.

Certain embodiments herein provide methods comprising administering oral formulations of cytidine analogs provided herein comprising delivering the cytidine analog (e.g., azacitidine) at a lower dose over a more prolonged period of time, as compared to IV or SC administration. In particular embodiments, such methods comprise managing dose-related cytopenias (including, e.g., dose-related cytopenias associated with azacitidine) by administering an oral formulation provided herein. In embodiments, methods provided herein comprise administering an oral formulation provided herein to achieve an improved safety profile as compared to an IV or SC dose comprising the same cytidine analog.

As described herein, certain embodiments provide methods for improved treatment of particular diseases or disorders (e.g., treatment of solid tumors) by administering an oral formulation provided herein, as compared to IV or SC administration of the cytidine analog. In particular embodiments, certain methods herein provide administering oral formulations provided herein at lower doses for more prolonged periods of time, leading to improved demethylation. For example, certain methods provided herein comprise administering an oral formulation provided herein to treat a solid tumor while avoiding certain dose-limiting-toxicity-related side effects associated with dosing the cytidine analog via SC or IV administration. An example of certain toxicity-related drawbacks associated with administration of a cytidine analog are described, e.g., in K. Appleton et al., *J. Clin. Oncol.*, Vol. 25(29):4603-4609 (2007), which is incorporated by reference herein in its entirety.

Particular embodiments herein provide methods for treating a subject having a disease or disorder provided herein by orally administering a pharmaceutical composition provided herein, wherein the treatment results in improved survival of the subject. In certain embodiments, the improved survival is measured as compared to one or more conventional care regimens. Particular embodiments herein provide methods for treating a subject having a disease or disorder provided herein by orally administering a pharmaceutical composition provided herein, wherein the treatment provides improved effectiveness. In particular embodiments, the improved effectiveness is measured using one or more endpoints for cancer clinical trials, as recommended by the U.S. Food and Drug Administration (FDA). For example, FDA provides Guidance for Industry on Clinical Trial Endpoints for the Approval of Cancer Drugs and Biologics. The FDA endpoints include, but are not limited to, Overall Survival, Endpoints Based on Tumor Assessments such as (i) Disease-Free Survival (ii) Objective Response Rate, (iii) Time to Progression and Progression-Free Survival and (iv) Time-to-Treatment Failure. Endpoints Involving Symptom Endpoints may include Specific Symptom Endpoints such as (i) Time to progression of cancer symptoms and (ii) A composite symptom endpoint. Biomarkers assayed from blood or body fluids may also be useful to determine the management of the disease.

In certain embodiments, the methods of treating disorders of abnormal cell proliferation comprise orally administering a formulation of a cytidine analog with food. In certain embodiments, the methods of treating disorders of abnormal cell proliferation comprise orally administering a formulation of a cytidine analog without food. In certain embodiments, pharmacological parameters (e.g., Cmax, Tmax) depend on the fed state of the subject. In certain embodiments, the formulation of the cytidine analog is administered sublingually.

In certain embodiments, the cytidine analog, e.g., 5-azacytidine, is not co-administered with a cytidine deaminase inhibitor. In certain embodiments, the oral formulation comprising a cytidine analog as provided herein is not co-administered with THU. Certain embodiments herein provide methods of treating a disease or disorder provided herein (e.g., a disease associated with abnormal cell proliferation) comprising orally administering a cytidine analog provided herein (e.g., 5-azacytidine) for release substantially in the stomach, wherein the methods achieve a particular biological parameter provided herein (e.g., a particular Cmax value, Tmax value, and/or AUC value provided herein), and wherein the methods comprise not co-administering a cytidine deaminase inhibitor with the cytidine analog. Certain embodiments herein provide methods of treating a disease or disorder provided herein (e.g., a disease associated with abnormal cell proliferation) comprising orally administering a cytidine analog provided herein (e.g., 5-azacytidine) for release substantially in the stomach, wherein the methods avoid adverse effects associated with administering a cytidine deaminase inhibitor (e.g., THU) by not co-administering the cytidine deaminase inhibitor with the cytidine analog. In particular embodiments, a cytidine deaminase inhibitor (e.g., THU) is co-administered with the cytidine analog in an amount of, e.g., less than about 500 mg/d, less than about 200 mg/d, less than about 150 mg/d, less than about 100 mg/d, less than about 50 mg/d, less than about 25 mg/d, less than about 10 mg/d, less than about 5 mg/d, less than about 1 mg/d, or less than about 0.1 mg/d.

In certain embodiments, methods provided herein comprise treating a disorder provided herein, including a hematologic disorder, by administering an oral dosage form comprising a cytidine analog to a subject in need thereof. In particular embodiments, oral dosage forms provided herein comprising 5-azacytidine are used to treat subjects having hematologic disorders. Hematologic disorders include, e.g., abnormal growth of blood cells which can lead to dysplastic changes in blood cells and hematologic malignancies such as various leukemias. Examples of hematologic disorders include, but are not limited to, acute myeloid leukemia (AML), acute promyelocytic leukemia (APML), acute lymphoblastic leukemia (ALL), chronic myelogenous leukemia (CML), chronic lymphocytic leukemia (CLL), myelodysplastic syndromes (MDS), and sickle cell anemia, among others. Other disorders that can be treated using the methods provided herein include, e.g., multiple myeloma (MM) and non-Hodgkin's lymphoma (NHL).

In certain embodiments, methods provided herein comprise treating AML by administering an oral dosage form comprising a cytidine analog to a subject in need thereof. AML is the most common type of acute leukemia that occurs in adults. Several inherited genetic disorders and immunodeficiency states are associated with an increased risk of AML. These include disorders with defects in DNA stability, leading to random chromosomal breakage, such as Bloom's syndrome, Fanconi's anemia, Li-Fraumeni kindreds, ataxia-telangiectasia, and X-linked agammaglobulinemia.

In certain embodiments, methods provided herein comprise treating APML by administering an oral dosage form comprising a cytidine analog to a subject in need thereof. APML represents a distinct subgroup of AML. This subtype is characterized by promyelocytic blasts containing the 15;17 chromosomal translocation. This translocation leads to the generation of the fusion transcript comprised of the retinoic acid receptor and a sequence PML.

In certain embodiments, methods provided herein comprise treating ALL by administering an oral dosage form comprising a cytidine analog to a subject in need thereof. ALL is a heterogenerous disease with distinct clinical features displayed by various subtypes. Reoccurring cytogenetic abnormalities have been demonstrated in ALL. The most common cytogenetic abnormality is the 9;22 translocation. The resultant Philadelphia chromosome represents poor prognosis of the subject.

In certain embodiments, methods provided herein comprise treating CML by administering an oral dosage form comprising a cytidine analog to a subject in need thereof. CML is a clonal myeloproliferative disorder of a pluripotent stem cell. CML is characterized by a specific chromosomal abnormality involving the translocation of chromosomes 9 and 22, creating the Philadelphia chromosome. Ionizing radiation is associated with the development of CML.

In certain embodiments, methods provided herein comprise treating MDS by administering an oral dosage form comprising a cytidine analog to a subject in need thereof. In certain embodiments, MDS includes one or more of the following myelodysplastic syndrome subtypes: refractory anemia, refractory anemia with ringed sideroblasts (if accompanied by neutropenia or thrombocytopenia or requiring transfusions), refractory anemia with excess blasts, refractory anemia with excess blasts in transformation, and chronic myelomonocytic leukemia. In certain embodiments, the MDS is higher-risk MDS. In certain embodiments, the methods provided herein comprise administering an oral dosage form comprising a cytidine analog to a subject in need thereof to increase the survival (e.g., prolong the life) of a subject with MDS.

In certain embodiments, methods provided herein comprise treating NHL by administering an oral dosage form comprising a cytidine analog to a subject in need thereof. Non-Hodgkin's Lymphomas (NHL) represent a heterogeneous group of malignancies of the lymphoid system. According to the WHO classification of hematological and lymphoid tumors, these diseases are classified as B-cell and T-cell neoplasms. B-cell lymphomas account for about 90% of all lymphomas, and the two most common histological disease entities are follicular lymphoma and diffuse large B-cell lymphoma. Approximately 55,000 to 60,000 new cases of NHL are diagnosed annually in the U.S. See, e.g., Ansell, S. M., et al., *Mayo Clin. Proc.*, 2005, 80(8):1087-97.

In certain embodiments, methods provided herein comprise treating MM by administering an oral dosage form comprising a cytidine analog to a subject in need thereof. Multiple myeloma is one of the most commonly diagnosed hematologic malignancies. In 2007, in the U.S. alone, there were roughly 20,000 new MM cases and 10,000 deaths due to MM. The disease is characterized by, inter alia, an accumulation of malignant plasma cells in the bone marrow, which can lead to the overproduction of an immunoglobulin, e.g., a monoclonal immunoglobulin G or A. These immunoglobulins, also known as paraproteins, can be detected in the urine and blood of patients with MM. Consequences of MM include anemia, the development of destructive bony lesions, and renal insufficiency. See, e.g., Rao, K. V., *American Journal of Health-System Pharmacy*, 2007, 64(17): 1799-1807.

In certain embodiments, methods provided herein comprise treating CLL by administering an oral dosage form comprising a cytidine analog to a subject in need thereof. Chronic lymphocytic lymphoma (CLL) is a malignancy of mature B lymphocytes and is the most prevalent lymphoid malignancy in the U.S. The WHO classification of B lymphocytic neoplasms groups B cell malignancies according to the presumed normal counterpart of the malignant cells. CLL is diagnosed by immunophenotype analysis of lymphocytes from the blood, bone marrow, or lymph nodes. See, e.g., Zent, C. S., et al., *Current Oncology Reports*, 2007, 9:345-52.

Certain embodiments herein provide methods for delivering a cytidine analog to a subject comprising administering to the subject in need thereof an oral formulation comprising a cytidine analog. In particular embodiments, oral formulations comprise (1) a therapeutically effective amount of a cytidine analog; and (2) an optional drug release controlling component capable of releasing the cytidine analog substantially in the stomach after a subject ingests the oral formulation comprising the cytidine analog. Certain embodiments herein provide a method for enhancing the oral bioavailability of a cytidine analog in a subject. Certain embodiments herein provide a method of increasing the oral bioavailability of a cytidine analog comprising orally administering a pharmaceutical composition provided herein. In certain methods provided herein, a pharmaceutical composition provided herein is orally administered to a subject, contacts the biological fluids of the subject's body, and is absorbed in the upper gastrointestinal tract, such as, for example, substantially in the stomach.

Certain embodiments herein provide a method of achieving a particular exposure value provided herein by administering an oral formulation comprising a cytidine analog (e.g., 5-azacytidine) provided herein. Certain embodiments herein provide a method of achieving a particular oral bioavailability value provided herein by administering an oral formulation comprising a cytidine analog (e.g., 5-azacytidine) provided herein. Certain embodiments herein provide a method of achieving a particular AUC value provided herein by administering an oral formulation comprising a cytidine analog (e.g., 5-azacytidine) provided herein. Certain embodiments herein provide a method of achieving a particular Cmax value provided herein by administering an oral formulation comprising a cytidine analog (e.g., 5-azacytidine) provided herein. Certain embodiments herein provide a method of achieving a particular Tmax value provided herein by administering an oral formulation comprising a cytidine analog (e.g., 5-azacytidine) provided herein.

Certain embodiments herein provide methods of treating a condition involving undesirable or uncontrolled cell proliferation by administering an oral formulation comprising a cytidine analog (e.g., 5-azacytidine) as provided herein. Such conditions include, e.g., benign tumors, various types of cancers such as primary tumors and tumor metastasis, hematological disorders (e.g. leukemia, myelodysplastic syndrome and sickle cell anemia), restenosis (e.g. coronary, carotid, and cerebral lesions), abnormal stimulation of endothelial cells (arteriosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants.

In certain embodiments, cells in a benign tumor retain their differentiated features and do not divide in a completely uncontrolled manner. A benign tumor may be localized and/or nonmetastatic. Specific types of benign tumors that can be treated using the methods, compositions, and formulations provided herein include, e.g., hemangiomas, hepatocellular adenoma, cavernous hemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In certain embodiments, cells in a malignant tumor become undifferentiated, do not respond to the body's growth control signals, and/or multiply in an uncontrolled manner. The malignant tumor may be invasive and capable of spreading to distant sites (metastasizing). Malignant tumors may be divided into two categories: primary and secondary. Primary tumors arise directly from the tissue in which they are found. A secondary tumor, or metastasis, is a tumor which is originated elsewhere in the body but has now spread to a distant organ. The common routes for metastasis are direct growth into adjacent structures, spread through the vascular or lymphatic systems, and tracking along tissue planes and body spaces (peritoneal fluid, cerebrospinal fluid, etc.).

Methylation can lead to the silencing of genes critical to cellular control (i.e., epigenetic gene silencing), and can be an early event in the development of malignant tumors including, e.g., colorectal cancer or lung cancer. See, e.g., M. V. Brock et al., *N. Engl. J. Med.*, 2008, 358(11):1118-28; P. M. Das et al., *Mol. Cancer,* 2006, 5(28); G. Gifford et al., *Clin. Cancer Res.,* 2004, 10:4420-26; J. G. Herman et al., *N. Engl. J. Med.*, 2003, 349:2042-54; A. M. Jubb et al., *J. Pathology*, 2001, 195:111-34. Accordingly, in certain embodiments, methods herein provide using oral formulations provided herein to prevent or reverse epigenetic gene silencing, e.g., by reversing abnormal DNA methylation. In specific embodiments, oral formulations provided herein are used for early intervention to prevent the development of cancer in patients at risk of developing cancer, e.g., familial polyposis or lung cancer, wherein a cause of the cancer is epigenetic gene silencing. In particular embodiments, such early intervention would be impractical by means other than oral administration (e.g., IV or SC administration). In specific embodiments, oral formulations provided herein are used for early intervention to prevent the recurrence of cancer in patients at risk for early relapse, e.g., colorectal cancer or non-small-cell lung cancer. In certain embodiments, the early intervention is achieved via prolonged oral dosing schedules, using formulations and/or methods as described herein. Certain embodiments provide methods for administering oral formulations provided herein to reverse the effect of gene silencing, e.g., in patients at risk of gene silencing due to epigenetic changes. In particular embodiments, methods provided herein further comprise administering an HDAC inhibitor compound (e.g., to restore chromatin to a transcriptionally active configuration after reversing abnormal DNA methylation). In particular embodiments, the HDAC inhibitor compound is entinostat (SNDX-275; formerly MS-275), an oral HDAC inhibitor that acts synergistically with targeted therapies and is selective for cancer-relevant HDAC isoforms 1, 2, and 3. In particular embodiments, a synergistic effect is achieved by co-administering 5-azacytidine and an HDAC inhibitor (e.g., etinostat) for the treatment of solid tumors (e.g., NSCLC) or hematological malignancies (e.g., MDS, CMMoL, or AML).

In certain embodiments, specific types of cancers or malignant tumors, either primary or secondary, that can be treated using the methods, compositions, and formulations provided herein include, e.g., leukemia, breast cancer, skin cancer, bone cancer, prostate cancer, liver cancer, lung cancer (e.g., non-small-cell lung cancer and small-cell lung cancer), brain cancer, cancer of the larynx, gall bladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronmas, intestinal ganglioneuromas, hyperplastic corneal nerve tumor, marfanoid habitus tumor, Wilm's tumor, seminoma, ovarian tumor, leiomyoma tumor, cervical dysplasia and in situ carcinoma, neuroblastoma, retinoblastoma, medulloblastoma, soft tissue sarcoma, malignant carcinoid, topical skin lesion, mycosis fungoides, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

Particular embodiments herein provide using the methods, compositions, and formulations provided herein to treat abnormal cell proliferation due to, e.g., insults to body tissue during surgery for a variety of surgical procedures, including, e.g., joint surgery, bowel surgery, and cheloid scarring. Proliferative responses associated with organ transplantation that may be treated using the methods, compositions, and formulations provided herein include those proliferative responses contributing to potential organ rejections or associated complications. Specifically, these proliferative responses may occur during transplantation of the heart, lung (e.g., non-small-cell lung cancer and small-cell lung cancer), liver, kidney, and other body organs or organ systems.

In certain embodiments, the amount of the cytidine analog in the formulations provided herein, the methods of administration thereof, or the methods of treatment as set forth herein, is a specific dosage amount as provided herein. In certain embodiments, oral azacitidine dosages, methods of administration thereof, or methods of treatment of at least one condition, including but not limited to MDS and AML, may range, e.g., between about 50 mg/m$^2$/day and about 2,000 mg/m$^2$/day, between about 100 mg/m$^2$/day and about 1,000 mg/m$^2$/day, between about 100 mg/m$^2$/day and about 500 mg/m$^2$/day, or between about 120 mg/m$^2$/day and about 250 mg/m$^2$/day. In certain embodiments, particular dosages are, e.g., about 120 mg/m$^2$/day, about 140 mg/m$^2$/day, about 150 mg/m$^2$/day, about 180 mg/m$^2$/day, about 200 mg/m$^2$/day, about 220 mg/m$^2$/day, about 240 mg/m$^2$/day, about 250 mg/m$^2$/day, about 260 mg/m$^2$/day, about 280 mg/m$^2$/day, about 300 mg/m$^2$/day, about 320 mg/m$^2$/day, about 350 mg/m$^2$/day, about 380 mg/m$^2$/day, about 400 mg/m$^2$/day, about 450 mg/m$^2$/day, or about 500 mg/m$^2$/day.

In certain embodiments, appropriate biomarkers may be used to determine or predict the effect of the pharmaceutical compositions comprising cytidine analogs on the disease state and to provide guidance to the dosing schedule. For example, particular embodiments herein provide a method of determining whether a patient diagnosed with MDS has an increased probability of obtaining a greater benefit from treatment with a pharmaceutical composition comprising a cytidine analog by assessing the patient's nucleic acid methylation status. In particular embodiments, the cytidine analog is azacitidine. In particular embodiments, the nucleic acid is DNA or RNA. In particular embodiments, the greater benefit is an overall survival benefit. In particular embodiments, the methylation status is examined in one or more genes, e.g., genes associated with MDS or AML. Specific embodiments involve methods for determining whether baseline DNA methylation levels influence overall survival in patients with MDS (e.g., higher risk MDS) treated with azacitidine. Specific embodiments provide methods for determining whether gene promoter methylation levels influence overall survival in patients with MDS (e.g., higher risk MDS).

For example, specific embodiments herein provide methods for evaluating the influence of gene methylation on prolonged survival in patients with MDS (e.g., higher risk MDS). In particular embodiments, such evaluation is used to predict overall survival in patients with MDS (e.g., higher risk MDS), e.g., upon treatment with a pharmaceutical composition comprising a cytidine analog, as provided herein. In particular embodiments, such evaluation is used for therapeutic decision-making. In specific embodiments, such therapeutic decision-making includes planning or adjusting a patient's treatment, e.g., the dosing regimen, amount, and/or duration of administration of the cytidine analogue.

Certain embodiments provide methods of identifying individual patients diagnosed with MDS having an increased probability of obtaining an overall survival benefit from cytidine analog treatment, using analysis of methylation levels, e.g., in particular genes. In specific embodiments, lower levels of nucleic acid methylation are associated with an increased probability of obtaining improved overall survival following azacitidine treatment. In particular embodiments, the increased probability of obtaining improved overall survival following treatment is at least a 5% greater probability, at least a 10% greater probability, at least a 20% greater probability, at least a 30% greater probability, at least a 40% greater probability, at least a 50% greater probability, at least a 60% greater probability, at least a 70% greater probability, at least an 80% greater probability, at least a 90% greater probability, at least at least a 100% greater probability, at least a 125% greater probability, at least a 150% greater probability, at least a 175% greater probability, at least a 200% greater probability, at least a 250% greater probability, at least a 300% greater probability, at least a 400% greater probability, or at least a 500% greater probability of obtaining improved overall survival following treatment, e.g., using a pharmaceutical composition comprising a cytidine analog as provided herein. In particular embodiments, the greater probability of obtaining improved overall survival following treatment is a greater probability as compared to the average probability of a particular comparison population of patients diagnosed with MDS. In specific embodiments, the comparison population is a group of patients classified with a particular myelodysplastic subtype, as described herein. In one embodiment, the comparison population consists of patients having higher risk MDS. In particular embodiments, the comparison population consists of a particular IPSS cytogenetic subgroup.

In particular embodiments, nucleic acid (e.g., DNA or RNA) hypermethylation status may be determined by any method known in the art. In certain embodiments, DNA hypermethylation status may be determined using the bone marrow aspirates of patients diagnosed with MDS, e.g., by using quantitative real-time methylation specific PCR ("qMSP"). In certain embodiments, the methylation analysis may involve bisulfite conversion of genomic DNA. For example, in certain embodiments, bisulfite treatment of DNA is used to convert non-methylated CpG sites to UpG, leaving methylated CpG sites intact. See, e.g., Frommer, M., et al., *Proc. Nat'l Acad. Sci. USA* 1992, 89:1827-31. Commercially available kits may be used for such bisulfite treatment. In certain embodiments, to facilitate methylation PCR, primers are designed as known in the art, e.g., outer primers which amplify DNA regardless of methylation status, and nested primers which bind to methylated or non-methylated sequences within the region amplified by the first PCR. See, e.g., Li et al., *Bioinformatics* 2002, 18:1427-31. In certain embodiments, probes are designed, e.g., probes which bind to the bisulfite-treated DNA regardless of methylation status. In certain embodiments, CpG methylation is detected, e.g., following PCR amplification of bisulfite-treated DNA using outer primers. In certain embodiments, amplified product from the initial PCR reaction serves as a template for the nested PCR reaction using methylation-specific primers or non-methylation-specific primers. In certain embodiments, a standard curve is established to determine the percentage of methylated molecules in a particular sample. Methods for detecting nucleic acid methylation (e.g., RNA or DNA methylation) are known in art. See, e.g., Laird, P. W., Nature Rev. Cancer 2003, 3:253-66; Belinsky, S. A., Nature Rev. Cancer 2004, 4:1-11.

In certain embodiments, statistical analyses are performed to assess the influence of particular methylation levels with the potential benefit of treatment with a particular pharmaceutical composition comprising a cytidine analog. In certain embodiments, the influence of methylation on overall survival is assessed, e.g., using Cox proportional hazards models and Kaplan-Meier (KM) methodology.

In certain embodiments, any gene associated with MDS and/or AML may be examined for its methylation status in a patient. Particular genes include, but are not limited to, CKDN2B (p15), SOCS1, CDH1 (E-cadherin), TP73, and CTNNA1 (alpha-catenin). Particular genes associated with MDS and/or AML, which would be suitable for use in the methods disclosed here, are known in the art.

1. Methods Comprising Co-Administering One or More Additional Therapeutic Agents with the Oral Formulations Disclosed Herein Certain embodiments herein provide methods of treating diseases or disorders disclosed herein (e.g., diseases or disorders involving abnormal cell proliferation), wherein the methods comprise co-administering an oral formulation disclosed herein (such as, for example, an oral formulation comprising 5-azacytidine) with one or more additional therapeutic agents (such as, for example, a cancer therapeutic agent) to yield a synergistic therapeutic effect. Particular co-administered therapeutic agents useful in the methods disclosed herein are disclosed throughout the specification. In particular embodiments, the additional therapeutic agent is co-administered in an amount that is a therapeutically effective amount. In particular embodiments, the additional therapeutic agent is co-administered in a separate dosage form from the cytidine analog dosage form with which it is co-administered. In particular embodiments, the additional therapeutic agent is co-administered in a dosage form (e.g., a single unit dosage form) together with the cytidine analog with which it is co-administered. In such cases, the cytidine analog (e.g., azacitidine) and the additional therapeutic agent may be co-formulated together in the same dosage form using methods of co-formulating active pharmaceutical ingredients, including methods disclosed herein and methods known in the art.

Incorporation By Reference: All disclosures (e.g., patents, publications, and web pages) referenced throughout this specification are incorporated by reference in their entireties. In addition, the following disclosures are also incorporated by reference herein in their entireties: (1) 2008 ASCO poster abstract by B. S. Skikne, M. R. Ward, A. Nasser, L. Aukerman, G. Garcia-Manero; and (2) G. Garcia-Manero, M. L. Stoltz, M. R. Ward, H. Kantarjian, and S. Sharma, Leukemia, 2008, 22, 1680-84.

VII. EXAMPLES

A. Example 1

5-Azacytidine tablets were manufactured using direct tablet compression followed by optional seal film-coating and/or enteric film-coating, as described below. Table 3 lists the excipients used in each of the tablet formulations. Table 4 describes the formula composition of the tablets using weights. Table 5 describes the formula composition of the tablets using percentages.

Formulation 1 was manufactured without the seal-coating step, which may have resulted in an enteric coat that contained a "leaky" enteric coating. Talc was only used in the enteric coating suspension for Formulation 1.

Except for Formulation 1, a common blend with 20% drug load of 5-azacytidine was used to manufacture all tablets. Vitamin E TPGS (d-alpha-tocopheryl polyethylene glycol 1000 succinate) was added to certain of the formulations to enhance absorption of 5-azacytidine. Vitamin E TPGS was not used in Formulation 6.

Figure 1:
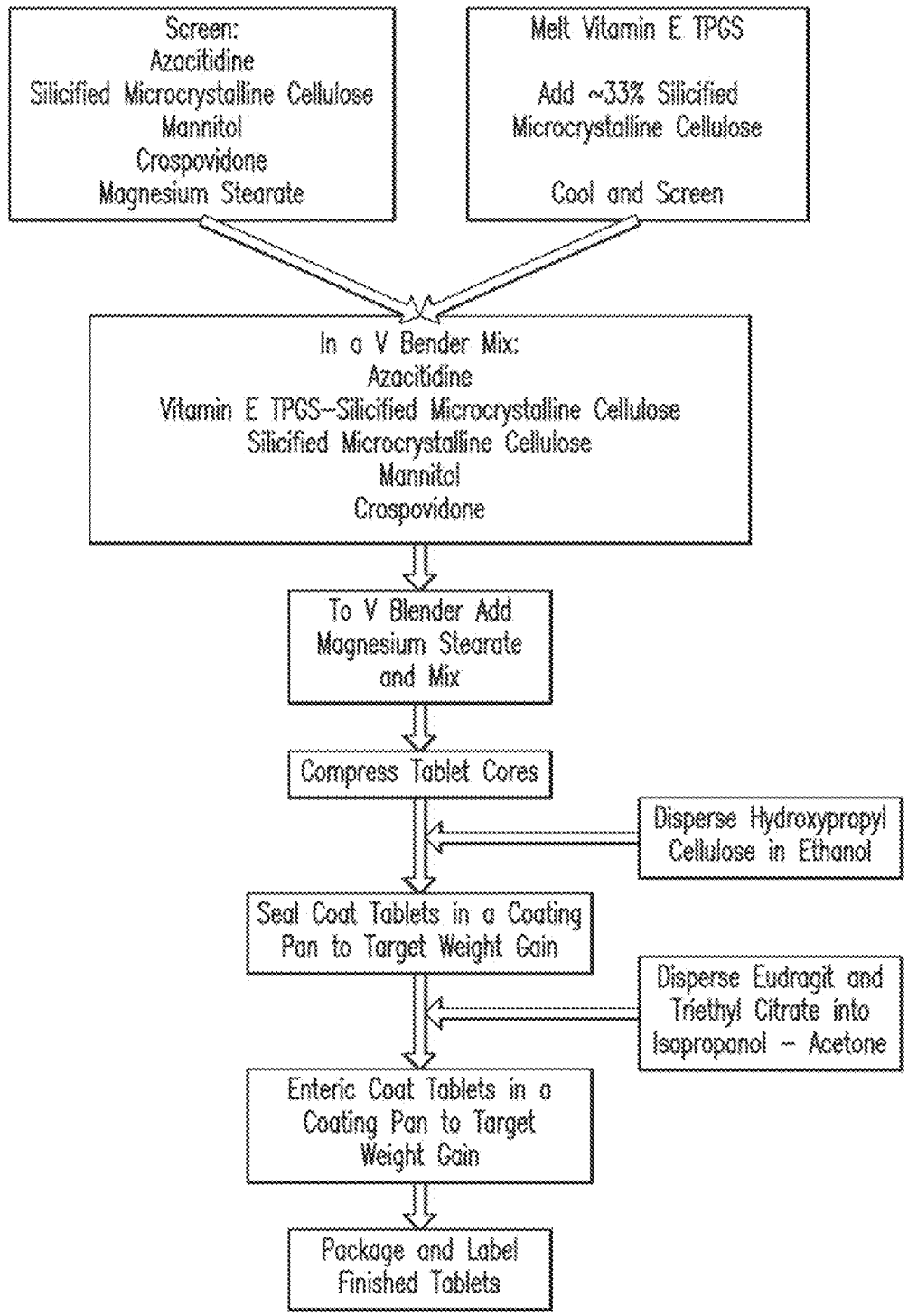
FIG. 1 represents processes and steps that may be used to make particular tablets comprising azacitidine for oral dosing; in specific embodiments, one or more steps may be optionally omitted.

Tablets were manufactured using the process described FIG. 1, except for Formulation 1 (which did not undergo the seal-coating step). Formulations 3 and 6 did not undergo the enteric film-coating step, and Formulation 6 did not contain Vitamin E TPGS. The process is generally described as follows:

Mannitol, silicified microcrystalline cellulose, crospovidone, magnesium stearate and azacitidine were individually screened to ensure de-aggregation of any agglomerates. Vitamin E TPGS was melted in a stainless steel vessel to which was then added a portion of the silicified microcrystalline cellulose (not done in Formulation 6). The Vitamin E TPGS-silicified microcrystalline cellulose mixture was allowed to cool and then screened. Azacitidine, Vitamin E TPGS-silicified microcrystalline cellulose mix, remaining silicified microcrystalline cellulose, mannitol and crospovidone were mixed in a V-blender. Magnesium stearate was added to the V-blender followed by additional mixing. The resulting blend was compressed into tablets using standard concave tooling.

Hydroxypropyl cellulose was dispersed into ethanol. The hydroxypropyl cellulose preparation was used to spray coat the tablet cores to prepare seal coated tablets.

EUDRAGIT and triethyl citrate were dispersed into an isopropanol-acetone mixed solvent system. EUDRAGIT-triethyl citrate preparation was used to spray coat the seal coated tablet.

TABLE 3

Components of Azacitidine Tablets

| Component | Function | Quality Standard |
|---|---|---|
| Azacitidine | API | In-House |
| Mannitol | Bulking Agent | USP |
| Silicified Microcrystalline Cellulose | Binding Agent | NF |
| d-alpha-tocopheryl polyethylene glycol 1000 succinate (Vitamin E TPGS) | Permeation Enhancer | NF |
| Polyvinyl Polypyrrolidone (Crospovidone) | Disintegrant | NF |
| Magnesium Stearate | Lubricant | NF |
| Hydroxypropyl Cellulose | Seal Film Coat | NF |
| Ethanol[a] | Coating Solvent | USP |
| Methacrylic Acid Copolymer (Eudragit S100, Eudragit LIDO-55 or Eudragit L100) | Enteric Film Coat | NF |
| Triethyl Citrate | Plasticizer | NF |
| Talc | Anti-Caking | USP |
| Isopropanol[a] | Coating Solvent | USP |
| Acetone | Coating Solvent | NF |

[a]Removed during processing (used as solvent for film-coating polymers).

TABLE 4

Formula Composition of Azacitidine Tablets (Weight)

Quantity per Unit Tablet (mg)

| Component | Formulation #1 Leaky coating (pH > 7.0) | Formulation #2 Enteric-coated (pH > 7.0) | Formulation #3 Immediate Release w/vitamin E | Formulation #4 Enteric-coated (pH > 5.0) | Formulation #5 Enteric-coated (pH > 5.5) | Formulation #6 Immediate Release w/o vitamin E |
|---|---|---|---|---|---|---|
| Azacitidine[a] | 20.0 | 20.0 | 60.0 | 60.0 | 60.0 | 60.0 |
| Mannitol, USP | 59.7 | 43.2 | 129.6 | 129.6 | 129.6 | 135.6 |
| Silicified Microcrystalline Cellulose, NF | 13.9 | 30.0 | 90.0 | 90.0 | 90.0 | 90.0 |
| Crospovidone, NF | 2.8 | 3.0 | 9.0 | 9.0 | 9.0 | 9.0 |
| Magnesium Stearate, NF | 1.6 | 1.8 | 5.4 | 5.4 | 5.4 | 5.4 |
| Vitamin E TPGS, NF | 2.0 | 2.0 | 6.0 | 6.0 | 6.0 | 0 |
| Core Tablet Total | 100.0 | 100.0 | 300.0 | 300.0 | 300.0 | 300.0 |
| Hydroxypropyl Cellulose, NF | N/A | 4.0 | 12.0 | 12.0 | 12.0 | 12.0 |
| Ethanol[b] | N/A | — | — | — | — | — |
| Seal-Coated Tablet Total | N/A | 104.0 | 312.0 | 312.0 | 312.0 | 312.0 |
| Eudragit S-100 | 3.7-5.9 | 7.0-8.0 | N/A | N/A | N/A | N/A |
| Eudragit L 100-55 | N/A | N/A | N/A | 21.8-25.0 | N/A | N/A |
| Eudragit L 100 | N/A | N/A | N/A | N/A | 28.1-31.2 | N/A |
| Triethyl Citrate | 0.3-0.5 | 1.0-2.0 | N/A | 3.0-6.0 | 3.0-6.0 | N/A |
| Talc | 1.0-1.6 | N/A | N/A | N/A | N/A | N/A |
| Isopropanol[b] | — | — | N/A | — | — | N/A |
| Acetone[b] | — | — | N/A | — | — | N/A |
| Total Theoretical Weight | 106.5 | 113.0 | 312.0 | 335.4 | 341.64 | 312.0 |

[a] Assuming 100% purity.
[b] Removed during processing.

TABLE 5

Formula Composition of Azacitidine Tablets (Percent)

Quantity per Unit Tablet (mg)

| Component | Formulation #1 Leaky coating (pH > 7.0) | Formulation #2 Enteric-coated (pH > 7.0) | Formulation #3 Immediate Release w/vitamin E | Formulation #4 Enteric-coated (pH > 5.0) | Formulation #5 Enteric-coated (pH > 5.5) | Formulation #6 Immediate Release w/o vitamin E |
|---|---|---|---|---|---|---|
| Azacitidine[a] | 20.0 | 20.0 | 20.0 | 20.0 | 20.0 | 20.0 |
| Mannitol, USP | 59.7 | 43.2 | 43.2 | 43.2 | 43.2 | 45.2 |
| Silicified Microcrystalline Cellulose, NF | 13.9 | 30.0 | 30.0 | 30.0 | 30.0 | 30.0 |
| Crospovidone, NF | 2.8 | 3.0 | 3.0 | 3.0 | 3.0 | 3.0 |
| Magnesium Stearate, NF | 1.6 | 1.8 | 1.8 | 1.8 | 1.8 | 1.8 |
| Vitamin E TPGS, NF | 2.0 | 2.0 | 2.0 | 2.0 | 2.0 | 0.0 |
| Core Tablet Total | 100.0 | 100.0 | 100.0 | 100.0 | 100.0 | 100.0 |
| Hydroxypropyl Cellulose, NF | N/A | 4.0 | 4.0 | 4.0 | 4.0 | 4.0 |
| Ethanol[b] | N/A | — | — | — | — | — |
| Seal-Coated Tablet Total | | 104.0 | 104.0 | 104.0 | 104.0 | 104.0 |
| Eudragit S-100 | 3.7-5.9 | 7.0-8.0 | N/A | N/A | N/A | N/A |
| Eudragit L 100-55 | N/A | N/A | N/A | 7.0-8.0 | N/A | N/A |
| Eudragit L 100 | N/A | N/A | N/A | N/A | 9.0-10.0 | N/A |
| Triethyl Citrate | 0.3-0.5 | 1.0-2.0 | N/A | 1.0-2.0 | 1.0-2.0 | N/A |
| Talc | 1.0-1.6 | N/A | N/A | N/A | N/A | N/A |

TABLE 5-continued

Formula Composition of Azacitidine Tablets (Percent)

| | Quantity per Unit Tablet (mg) | | | | | |
|---|---|---|---|---|---|---|
| Component | Formulation #1 Leaky coating (pH > 7.0) | Formulation #2 Enteric-coated (pH > 7.0) | Formulation #3 Immediate Release w/vitamin E | Formulation #4 Enteric-coated (pH > 5.0) | Formulation #5 Enteric-coated (pH > 5.5) | Formulation #6 Immediate Release w/o vitamin E |
| Isopropanol [b] | — | — | N/A | — | — | — |
| Acetone [b] | — | — | N/A | — | — | — |

[a] Assuming 100% purity.
[b] Removed during processing

B. Example 2

Studies were performed to evaluate the effect of aqueous film coating on hydrolytic degradation of azacitidine. Azacitidine tablets were film-coated using aqueous-based solvents without affecting levels of degradation. As demonstrated in Table 6, significant levels of azacitidine degradation products were not observed after aqueous film coating.

TABLE 6

Effect of Aqueous Film Coating on Azacitidine

| Test | Uncoated Core Tablet | Coated Tablet |
|---|---|---|
| Assay (% Label Claim) | Ave = 103.1 | Ave = 99.6 |
| Related Substances (% Area) | | |
| N-Formylguanylribosylurea | 0.2 | 0.1 |
| Guanylribosylurea | 0.7 | 0.7 |
| Unspecified | ND | ND |
| Total | 0.9 | 0.8 |
| Moisture Content (% w/w) | NMT 2.5 | 2.2 |

ND = Not detected;
NMT = No more than

C. Example 3

As described in Example 1, the following six formulations, described in Table 7 and elsewhere in the present specification, were prepared and used in clinical studies as described in the Examples below:

TABLE 7

Formulations of Azacitidine used in clinical studies

| Formulation Number | Azacitidine in Formulation | Description |
|---|---|---|
| #1 | 20 mg | "Leaky" enteric-coated tablet |
| #2 | 20 mg | Enteric-coated tablet, core sealed |
| #3 | 60 mg | Seal-coated, immediate release tablet with vitamin E |
| #4 | 60 mg | Enteric film-coated tablet, target dissolution at pH > 5.5 |
| #5 | 60 mg | Enteric film-coated tablet, target dissolution at pH > 6.0 |
| #6 | 60 mg | Seal-coated, immediate release tablet without vitamin E |

D. Example 4

In a multiple dose escalation study (MTD study; CL005), patients with MDS or AML were selected (Selection criteria: ECOG PS 0-2, adequate organ function, age >18 years). The patients were dosed with multiple 28-day cycles of azacitidine. The study had a 3+3 design. During Cycle 1, all patients were dosed subcutaneously with azacitidine at 75 mg/m$^2$×7 days. During subsequent cycles (dosing on Day 1-7 for each cycle), the patients were dosed orally with azacitidine at doses listed in Table 8. PK data were collected during Cycles 1 and 2 on Day 1 and 7, and during Cycles 4, 5, and 7, on Day 7. PD data were collected during each cycle, and hematological responses and/or improvement rates were assessed for each treatment cycle to determine biologically active dose (BAD). To date, seven cohorts of patients (3 subjects/cohort) have been studied and none of the patients have shown dose limited toxicity (DLT). The oral dose and formulation used for each cohort are listed in Table 8.

TABLE 8

Oral Azacitidine Doses and Formulations

| Cohort # Dosage | Oral Formulation | Subject Demographics (Patient No.- gender, age, dx) | # Subjects Treated/Evaluable for DLT | # Subjects with DLT |
|---|---|---|---|---|
| Cohort 1 120 mg | Formulation #2 (20 mg tablets) | 02001 - M, 78, MDS<br>02002 - M, 66, MDS RAEB-2<br>04001 - M, 56, MDS RAEB-1 | 3/3 | 0 |
| Cohort 2 120 mg | Formulation #1 (20 mg tablets) | 02003 - M, 73, AML<br>02004 - M, 61, MDS<br>04002 - M, 73, MDS RAEB-1<br>02005 - M, 66, MDS RAEB-1 | 4/3 | 0 |
| Cohort 3 180 mg | Formulation #1 (20 mg tablets) | 04004 - F, 70, AML<br>02006 - M, 61, AML<br>03001 - F, 70, MDS RAEB-2 | 3/3 | 0 |

TABLE 8-continued

Oral Azacitidine Doses and Formulations

| Cohort #<br>Dosage | Oral<br>Formulation | Subject Demographics<br>(Patient No.-<br>gender, age, dx) | # Subjects<br>Treated/Evaluable<br>for DLT | # Subjects<br>with DLT |
|---|---|---|---|---|
| Cohort 4<br>240 mg | Formulation<br>#3 (60 mg<br>tablets) | 02007 - M, 76, CMML<br>02008 - M, 80, MDS RAEB-1<br>02009 - M, 83, MDS RAEB-2 | 3/3 | 0 |
| Cohort 5<br>300 mg | Formulation<br>#3 (60 mg<br>tablets) | 04005 - M, 68, MDS RCMD<br>02011 - M, 92, MDS RAEB-1<br>02012 - M, 62, MDS RCMD | 3/3 | 0 |
| Cohort 6<br>360 mg | Formulation<br>#3 (60 mg<br>tablets) | 02013 - F, 66, MDS RAEB-1<br>03002 - M, 65, MDS RAEB-1<br>01001 - F, 63, MDS RCMD | 3/3 | 0 |
| Cohort 5<br>480 mg | Formulation<br>#3 (60 mg<br>tablets) | 01002 - M, 70, MDS RARS<br>01003 - F, 75, MDS RCMD | 2/0* | 0 |

*Cycle 2 ongoing

Figure 2:
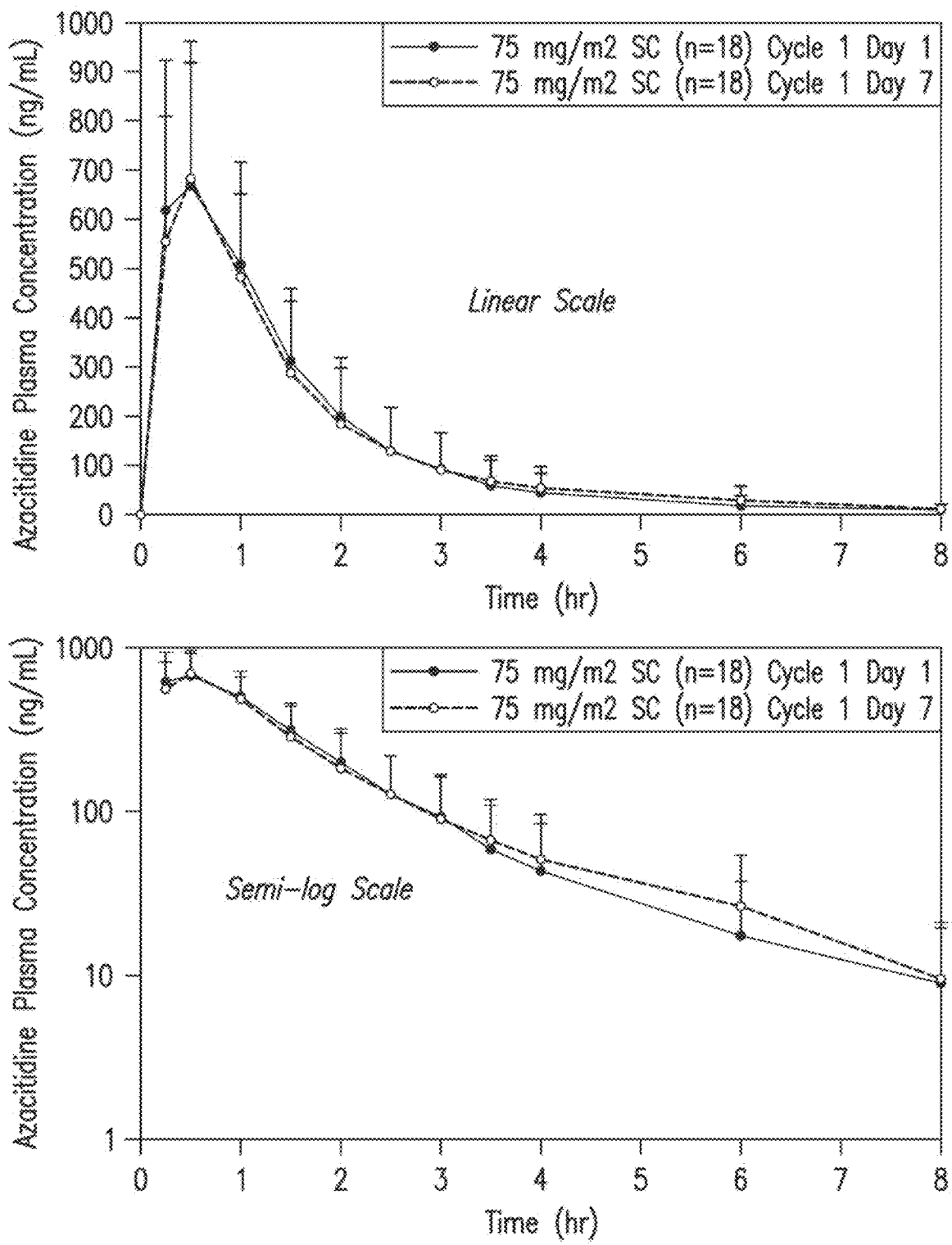
FIG. 2 represents human PK profiles following 75 mg/m$^2$ SC dosing of azacitidine on Days 1 and 7 in a multiple dose escalation study (n=18). The X-axis represents time; the Y-axis represents azacitidine plasma concentrations (mean±SD).

PK profiles for Cycle 1, following 75 mg/m² SC dose of azacitidine, are presented in FIG. 2. Pharmacokinetic parameters calculated from azacitidine plasma concentrations following SC doses at 75 mg/m² are presented in Table 9.

TABLE 9

PK parameters from Cycle 1, following SC doses at 75 mg/m²

| | | AUC(0-t)<br>(ng * hr/mL) | AUC(0-inf)<br>(ng * hr/mL) | Cmax<br>(ng/mL) | Tmax<br>(hr) | Lambda_z<br>(1/hr) | t1/2<br>(hr) | Cloral<br>(L/hr) | Vdoral<br>(L) |
|---|---|---|---|---|---|---|---|---|---|
| Day 1 | Mean (n = 18) | 1135 | 1170 | 741 | 0.49 | 0.58 | 1.53 | 143 | 318 |
| | SD | 514 | 533 | 293 | 0.27 | 0.29 | 0.80 | 53 | 223 |
| | Minimum | 505 | 538 | 224 | 0.23 | 0.22 | 0.61 | 45 | 90 |
| | Median | 991 | 1030 | 674 | 0.50 | 0.56 | 1.24 | 156 | 265 |
| | Maximum | 2821 | 2950 | 1310 | 1.08 | 1.14 | 3.15 | 253 | 788 |
| | CV % | 45 | 46 | 39 | 54 | 49 | 52 | 37 | 70 |
| Day 7 | Mean (n = 18) | 1135 | 1210 | 697 | 0.51 | 0.62 | 1.73 | 133 | 368 |
| | SD | 477 | 463 | 252 | 0.17 | 0.39 | 1.28 | 43 | 376 |
| | Minimum | 510 | 686 | 254 | 0.25 | 0.16 | 0.47 | 48 | 98 |
| | Median | 1020 | 1116 | 716 | 0.50 | 0.55 | 1.26 | 148 | 162 |
| | Maximum | 2718 | 2783 | 1050 | 1.00 | 1.49 | 4.30 | 223 | 1383 |
| | CV % | 42 | 38 | 36 | 34 | 62 | 74 | 33 | 102 |

Plasma PK profiles following SC (75 mg/m²) and various PO doses are compared and presented in FIG. 3. An increase in oral dose did not result in dose-proportional increase in exposure of azacitidine.

Methylation PD data in cycles 1 and 2, from blood (PBL) and bone marrow (BM) samples, were obtained. The PD data collected from individual patients from Cohort 4 (Formulation #3, oral dose 240 mg) are presented in FIGS. 4A-4D and FIGS. 5A-5D.

Subject number 02004 of cohort 2 (61-year-old male with MDS, MDACC) was treated with a SC cycle of azacitidine, followed by initial oral doses of 120 mg azacitidine (Formulation #1). The patient received oral doses of 120 mg×7 d azacitidine as in Formulation #1 during Cycles 2-6, followed by oral doses of 180 mg×7 d azacitidine during Cycles 7-12. In this patient, following a 75 mg/m² SC dose of azacitidine, the AUC value was 1000 ng*hr/mL. Following a 180 mg oral dose of azacitidine, the AUC value was 330 ng*hr/mL, approximately 33% of the exposure observed for the SC dose (oral bioavailability=30%).

The PD response data from patient 02004 is presented in FIGS. 6A-6D. Platelets (K/uL), Hgb (g/dL), ANC (K/uL), and Relative BM Blast (%) are plotted vs. sampling dates over the course of the study. The patient demonstrated a morphologic complete response (CR).

For patient 02004, Hgb (10.8 g/dL at a screening, 11.1 g/dL at Day 1), Platelets (140 K/uL at both screening and Day 1), ANC (1.46 K/uL at screening and 1.12 K/uL at Day 1), and BM Blast (2%) values at baseline and Day 1 were above normal or close to normal. This patient had no transfusion (RBC or PLT) prior to enrollment into the study and to day required no transfusions (RBC or PLC) during the study. Per IWG 2006 criteria, the patient achieved complete response (CR) (from Days 45-74 satisfying all CR criteria for 28 consecutive days). The patient achieved morphologic complete response per the IWG AML criteria. However, with regard to the ANC condition for the IWG 2000 CR criteria, the patient did not meet the criteria for a complete response (3 days short of the duration requirement of 56 consecutive days).

Figure 5A:
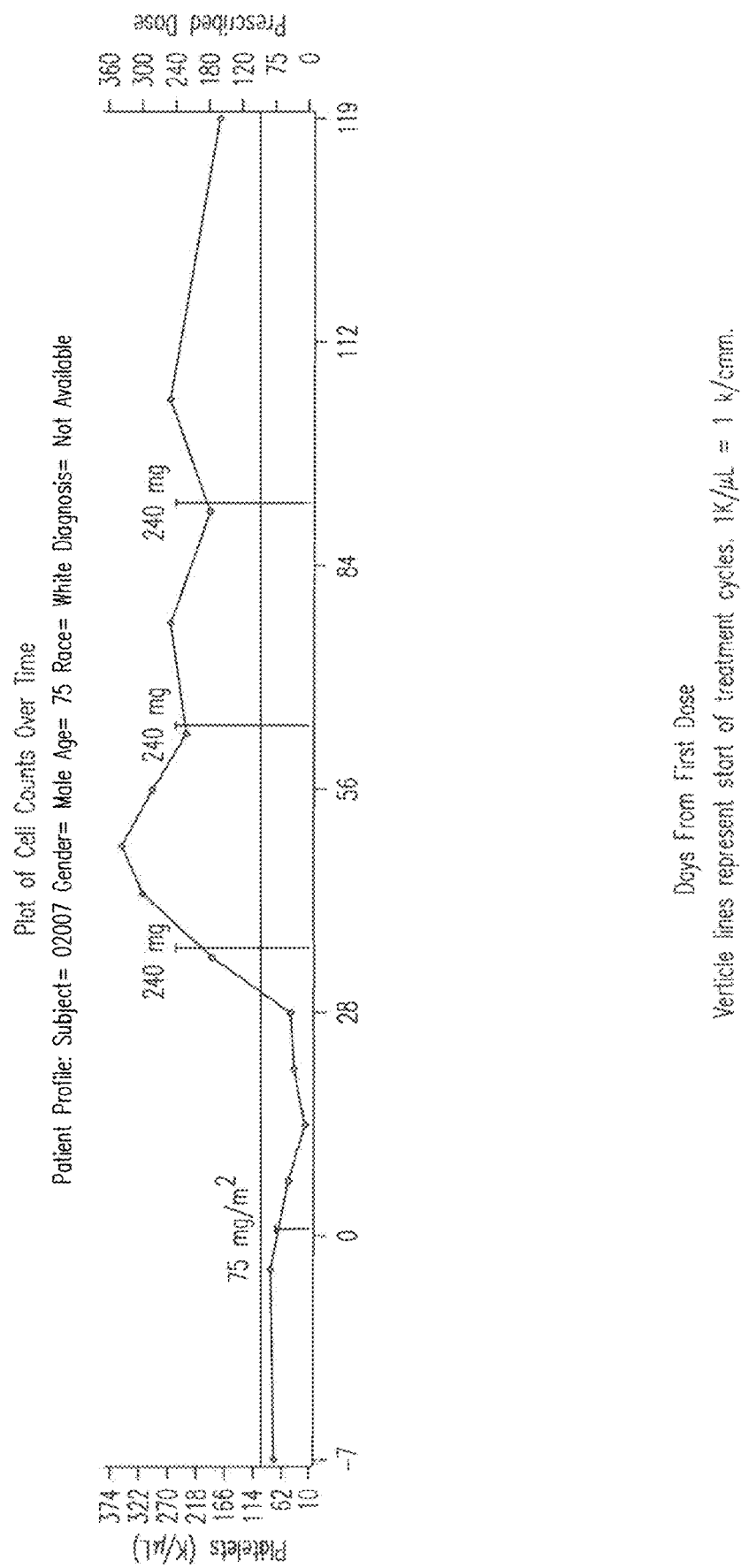
Figure 5B:
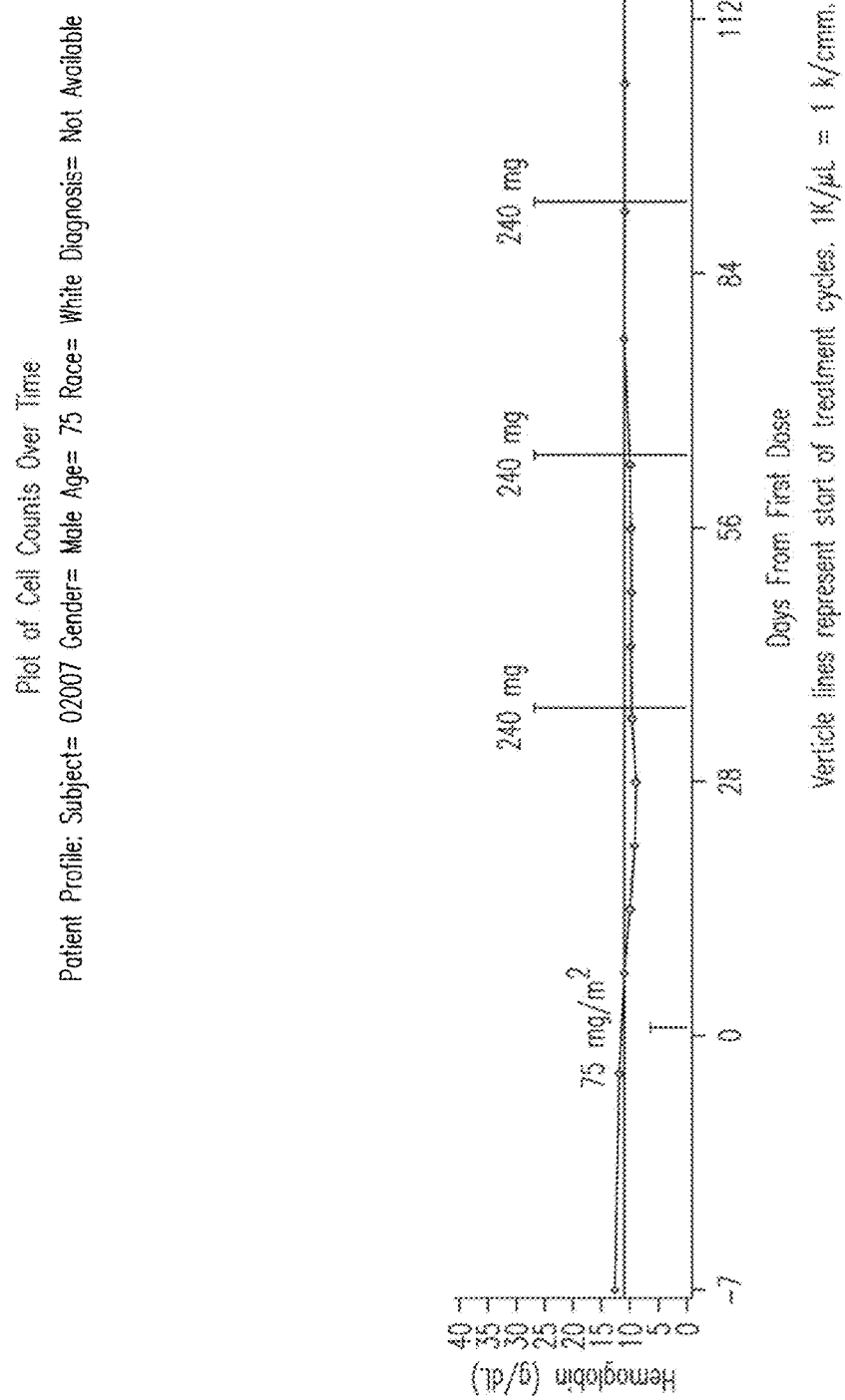
Figure 5C:
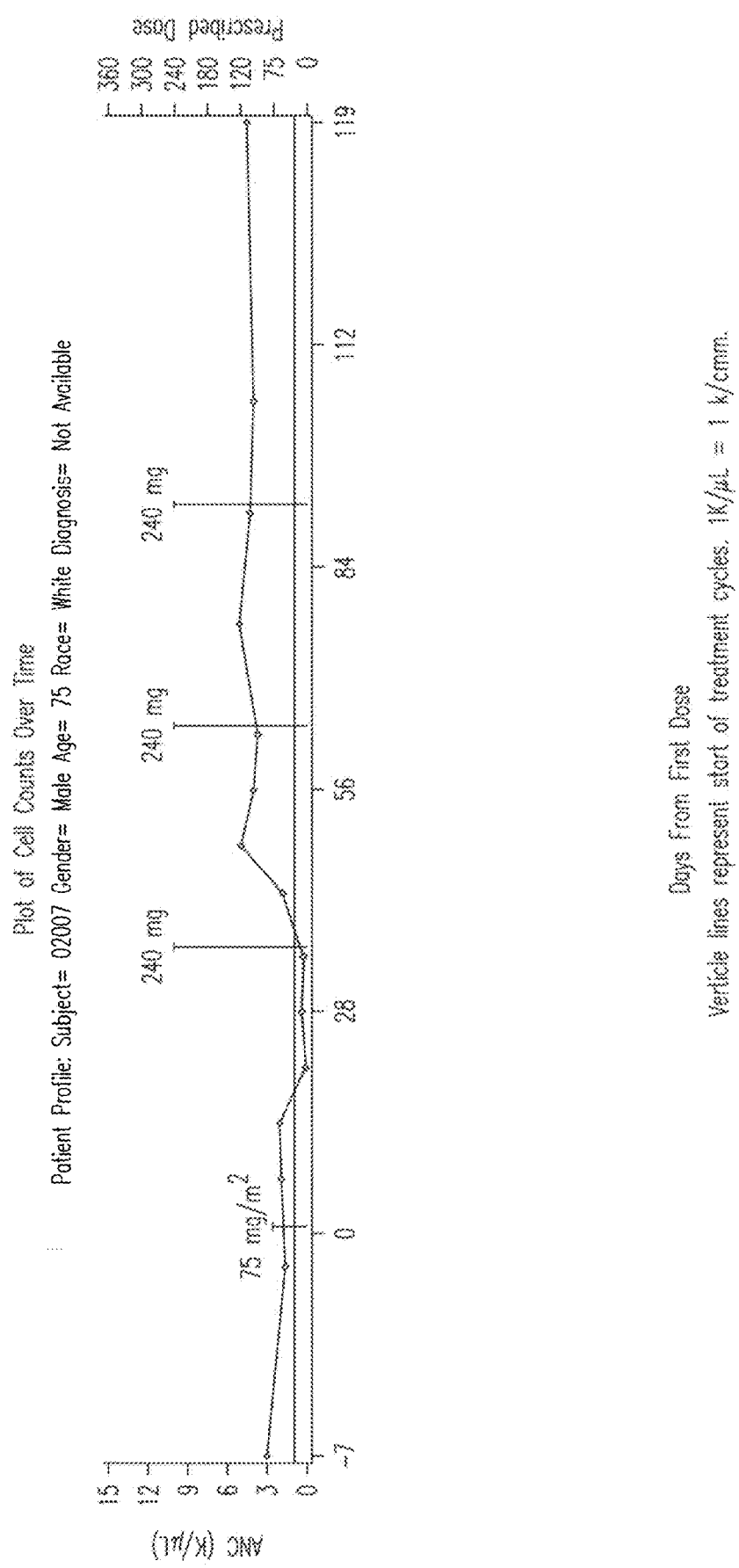
Figure 5D:
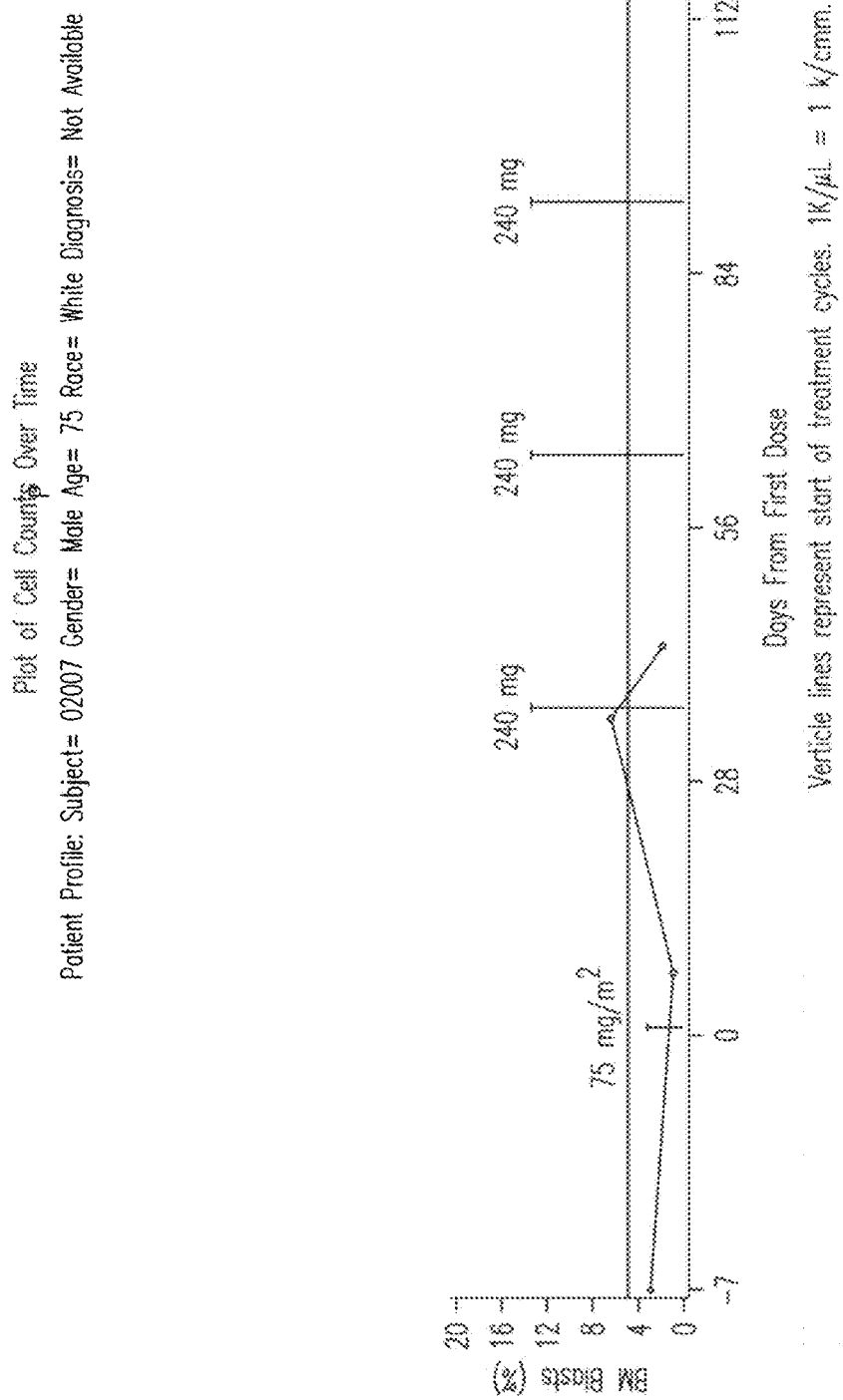
Figure 6A:
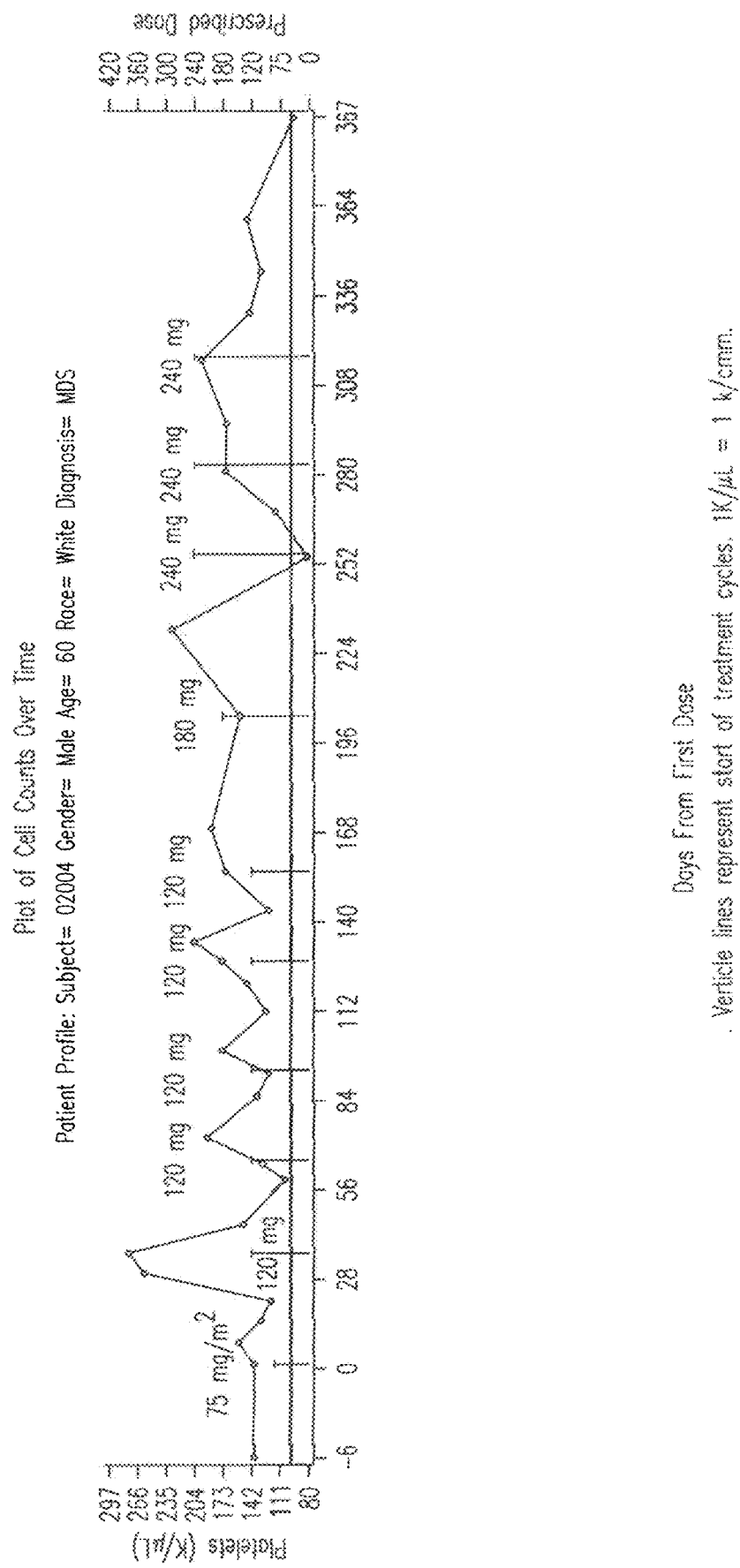
Figure 6B:
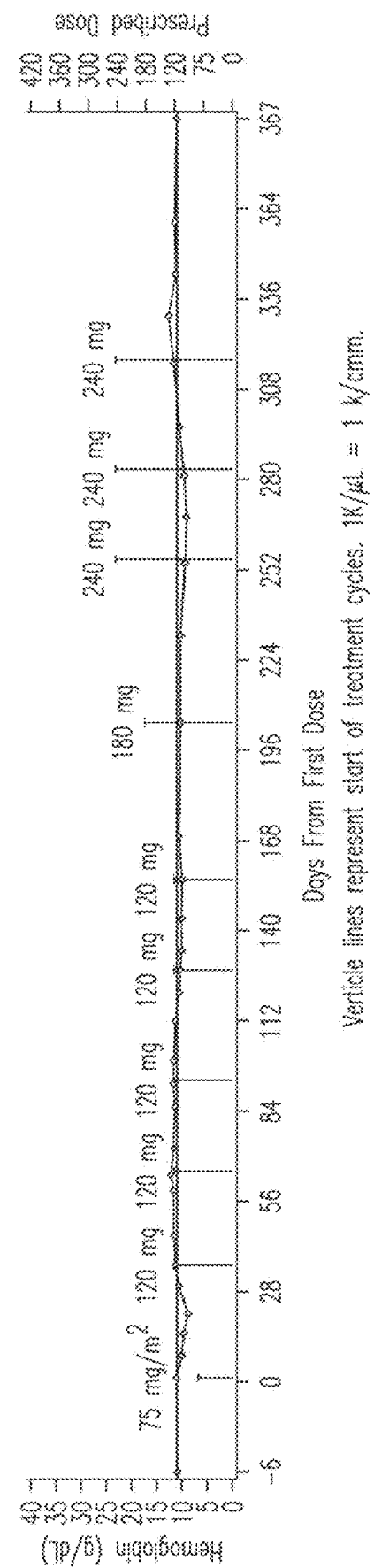
Figure 6C:
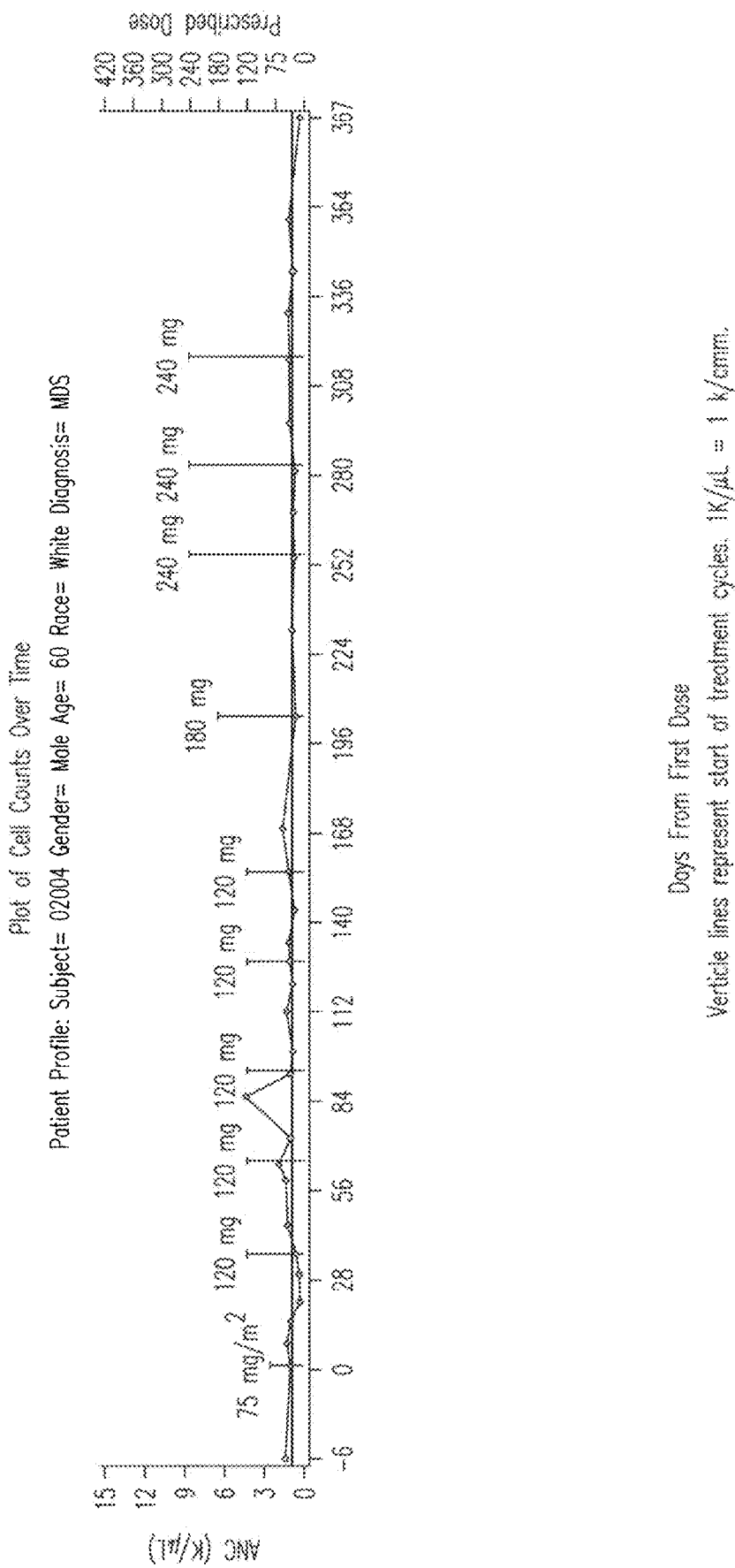
Figure 6D:
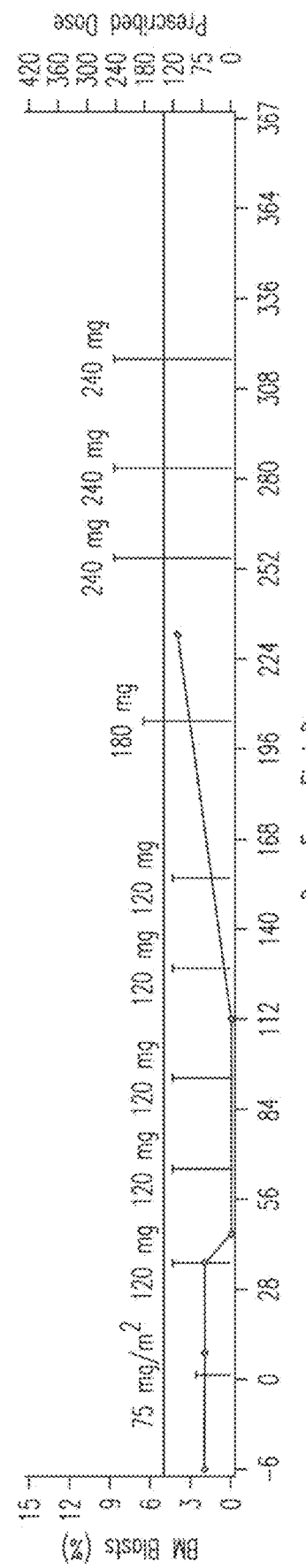

For patient 02007, as shown in FIGS. 5A and 5C, Grade 4 thrombocytopenia and neutropenia developed during the first cycle of treatment with subcutaneous azacitidine when given at 75 mg/m² for 7 days. The onset of the cytopenias occurred between days 14 and 21 at time points consistent with the existing safety profile of azacitidine when administered 75 mg/m² for 7 days as a SC injection. In contrast, the administration of oral azacitidine starting with cycle 2 did not result in grade 3 or 4 cytopenias yet still produced an increase in platelets above the baseline levels. This data supports, e.g., the conclusion that certain oral dosage forms provided herein permit the delivery of azacitidine at lower doses over a more prolonged period of time, and that certain oral dosage forms provided herein alter the safety profile of the cytidine analog.

Assessment of IWG criteria for certain patients in the MTD study is presented below in Table 10. The data demonstrate, inter alia, patient improvement following administration of azacitidine formulated for release substantially in the stomach.

TABLE 10

MTD Study; Assessment of IWG Criteria

| Patient No. | IWG Assessment |
|---|---|
| 02004 | Fairly healthy at baseline: hgb (11.1 g/dL Cycle 1, Day 1); PLT (140 K/μL Cycle 1, Day 1); ANC (1.12 K/μL at Cycle 1, Day 1); BM blasts (2%) values at baseline above normal or close to normal<br>CR per IWG 2006 (Days 45-98)<br>Morphologic CR per the IWG AML criteria (Diagnosis is MDS) |
| 02007 | HI-P major improvement per IWG 2000 (Days 35-202)<br>Morphologic CR per the revised IWG AML criteria on Days 43-188 and on some other days (ANC = 1.89 K/μL, but normal at BL = 2.99 and 1.68; PLT = 314 K/μL; BM = 2, but normal at BL = 3) (Diagnosis is CMML) |
| 02008 | HI-P major improvement per IWG 2000 (Days 34-110) |
| 02009 | Marrow CR (Days 7-111+) per IWG 2006 |
| 02011 | Marrow CR (Days 7-177+) per IWG 2006<br>Morphologic CR per the revised IWG AML criteria on Day 21 (ANC = 1.18 K/μL; PLT = 119 K/μL, but normal at BL = 162 & 194; BM = 3) (Diagnosis is MDS) |

Immediate release oral formulations comprising azacitidine demonstrated bioavailability in patients. Observations thus far suggest positive clinical activity in patients treated with oral azacitidine formulations. No safety issues have thus far been observed with the doses and schedules described above.

E. Example 5

An oral azacitidine clinical study, referred to as the Rapid Aza Clinical Evaluation (RACE) study (CL008), was performed; a summary of the study design is depicted in FIG. 7. Several oral formulations were evaluated in this study. A "3+7" cohort of patients was enrolled in the study, i.e., three patients were initially tested per formulation, and the cohorts could increase in size up to ten patients. Cohorts were enrolled in parallel. PK data was collected periodically, as indicated in Table 11.

TABLE 11

RACE Study - PK Study Design; PK Cycle 1, Days 1, 3, 5, 15, 17 & 19, and Cycle 2, Day 7

| Treatment Day | Dose |
|---|---|
| PK Phase (Cycle 1) | |
| Day 1 | 75 mg/m² SC |
| Day 3 ± 1* | 180 mg Oral |
| Day 5 ± 1* | 360 mg Oral |
| Day 15 ± 1* | 75 mg/m² SC |
| Day 17 ± 1* | Oral dose calculated to achieve approximately 80% exposure relative to the 75 mg/m² SC dose up to a maximum dose of 1,200 mg. |
| Day 19 ± 1* | Oral dose calculated to achieve approximately 120% exposure relative to the 75 mg/m² SC dose up to a maximum dose of 1,200 mg. |
| Treatment Phase (Cycles 2-7) | |
| Days 1-7 | Oral dose calculated to achieve approximately 100% exposure relative to the 75 mg/m² SC dose up to a maximum dose of 1,200 mg. |

*Dose administered ±1 day, as long at least 48 hours between doses

Results for Formulation #4: The plasma PK profile for one subject who received Formulation 4 (i.e., enteric film-coated tablets for release in upper gastrointestinal region) is depicted in FIG. 8. Values for AUC (0-t) (ng*hr/mL) were as follows: SC administration of 75 mg/m² (124 mg)=2390 (day 1) and 2440 (day 15); Oral administration of 180 mg=234; Oral administration of 360 mg=197; and Oral administration of 1200 mg=66.5 (day 17) and 297 (day 19). Tmax for oral administration was reached between 2.5 hr and 3.0 hr. A linear increase of exposure (AUC0-inf) was not observed following 180, 360, and 1200 mg oral doses. Relative oral bioavailability ranged between 0.8 to 6.7%.

Results for Formulation #6: The plasma PK profile for one subject who received Formulation 6 (i.e., seal-coated immediate release tablets without vitamin E) is depicted in FIG. 9. Values for AUC(0-∞) (ng*hr/mL) were as follows: SC administration of 75 mg/m² (120 mg)=1720 (day 1) and 1640 (day 15); Oral administration of 180 mg=231; Oral administration of 360 mg=280; and Oral administration of 1200 mg=543 (day 17) and 467 (day 19). Tmax for oral administration was reached between 0.5 hr and 1.0 hr. A linear increase of exposure (AUC 0-co) was observed following 180, 360, and 1200 mg oral doses, although the increase was not proportional with dose. Following the 1200 mg oral doses, AUC was approximately 30% of AUC following SC dosing (i.e., about 500 and about 1,700, respectively).

Data from this study indicated that azacitidine was absorbed following oral administration of immediate release formulations comprising azacitidine. As compared to SC administration of azacitidine, the immediate release azacitidine formulations provided a superior percent exposure (e.g., about 30%) than enteric-coated azacitidine formulations. Data supports single or multiple daily dosing of oral azacitidine.

F. Example 6

Based on data from clinical studies involving different azacitidine formulations and dosage amounts, plots were prepared comparing different formulations with respect to, e.g., their resulting PK profiles, AUC values, Cmax values, relative oral bioavailability values, and exposure values. Oral formulations involved in the comparisons include Formulation #3 ("F3"); Formulation #4 ("F4"); and Formulation #6 ("F6"); these oral formulations are described elsewhere herein (e.g., in Examples 1 and 3).

Comparisons of Formulation Nos. 3, 4, and 6

FIG. 10 compares PK profiles (using a linear scale) following administration of azacitidine via SC (75 mg/m²; n=18) and oral administration. For Formulation #3, a total of 360 mg azacitidine was orally administered (n=6); for Formulation #4, a total of 360 mg azacitidine was orally administered (n=3); for Formulation #6, a total of 360 mg azacitidine was orally administered (n=5). The plot illustrates immediate release characteristics of Formulations #3 and #6, as compared to Formulation #4, which was enteric coated. FIG. 11 provides the same data, plotted on a semi-log scale.

Patients were dosed with azacitidine SC (75 mg/m$^2$) and orally with Formulations #3, #4, or #6 ("F3"; "F4"; and "F6"; described elsewhere herein) with a total of 180 mg, 240 mg, 300 mg, 360 mg, 540 mg, 600 mg, 720 mg, 900 mg, 1080 mg, or 1200 mg azacitidine administered per patient. Results showed that azacitidine is absorbed following oral administration. As described below, particular values were measured and compared, including AUC values, Cmax values, relative oral bioavailability values, and exposure values (oral) compared to SC.

FIG. 12 displays AUC values (ng*hr/mL; mean±SD) following azacitidine administration. FIG. 13 displays Cmax values (ng/mL; mean±SD) following azacitidine administration. For Formulation #4 (enteric coated), over the dose range of 180 mg to 1200 mg, an increase in dose did not translate into an increase in exposure, and absorption was poor. For Formulation #3 (immediate release tablets with vitamin E), over the dose range of 180 mg to 1200 mg, an increase in dose translated into an increase in exposure. For Formulation #6 (immediate release tablets without vitamin E), over the dose range of 180 mg to 1200 mg, an increase in dose translated into an increase in exposure. Tmax for immediate-release Formulations #3 and #6 were similar: For Formulation #3, median Tmax was 1.1 hr (range 0.5, 2.5 hr); For Formulation #6, median Tmax was 1.0 hr (range 0.5, 3.0 hr).

FIG. 14 displays relative oral bioavailability (%; mean±SD) following oral dosing with Formulations #3, #4, and #6, at various azacitidine dosage levels. At dosage levels less than or equal to 360 mg azacitidine, Formulation #4 (enteric coated) had a mean relative oral bioavailability of less than 4%. At dosage levels less than or equal to 360 mg azacitidine, Formulation #3 (immediate release with vitamin E) had a mean relative oral bioavailability ranging from 11% to 21%. At dosage levels less than or equal to 360 mg azacitidine, Formulation #6 (immediate release without vitamin E) had a mean relative oral bioavailability ranging from 11% to 14%.

FIG. 15 displays exposure (% as compared to SC; mean±SD) following oral dosing with Formulations #3, #4, and #6, at various azacitidine dosage levels. At dosage levels less than or equal to 360 mg azacitidine, Formulation #4 (enteric coated) had a mean exposure of less than 8%. At dosage levels less than or equal to 360 mg azacitidine, Formulation #3 (immediate release with vitamin E) had a mean exposure ranging from 18% to 37%. At dosage levels less than or equal to 360 mg azacitidine, Formulation #6 (immediate release without vitamin E) had a mean exposure ranging from 20% to 31%. As compared to enteric-coated Formulation #4, the immediate-release Formulations #3 and #6 provided superior exposure compared to SC (about 30% at total dosage amount of 360 mg).

Comparisons of Formulation Nos. 3 and 6

FIG. 16 displays a linear scale profiles of azacitidine plasma concentration (ng/ml) versus time (hr) for Formulation #3 and #6 at a dosage level of 180 mg (n=6). FIG. 17 displays linear scale profiles of azacitidine plasma concentration (ng/ml) versus time (hr) for Formulation #3 and #6 at a dosage level of 360 mg (n=6).

FIG. 18 displays a plot of individual ("ind") and mean azacitidine AUC(0-inf) (ng*hr/ml) versus azacitidine dose (mg) for Formulation #3 and #6, with linear regression analysis. Linear regression equations for F3 and F6 are also indicated on the plot. Using those equations, for a selected dose, the expected AUC(0-inf) (ng*hr/ml) were calculated. Calculated values are provided in Table 12.

TABLE 12

Expected AUC(0-inf) Calculated for Formulation #3 and #6

| Azacitidine Dose (mg) | AUC(0-inf) (ng * hr/ml) | |
|---|---|---|
| | Formulation #6 | Formulation #3 |
| 240 | 263 | 338 |
| 360 | 296 | 363 |
| 480 | 328 | 388 |
| 600 | 361 | 413 |
| 720 | 393 | 438 |
| 1200 | 523 | 538 |

F6 linear regression equation: y = 0.2706 x + 198.19
F3 linear regression equation: y = 0.2079 x + 288.07

FIG. 19 displays a comparison of azacitidine percent relative oral bioavailability (mean±SD) versus azacitidine dose (mg), following dosing with Formulation #3 or #6, for azacitidine oral dosage amounts including 180 mg, 240 mg, 300 mg, 360 mg, 480 mg, 600 mg, 720 mg, 900 mg, 1020 mg, 1080 mg, 1140 mg, and 1200 mg. At doses greater than or equal to 1020 mg, the mean relative oral bioavailability for Formulation #6 ranged from 9% to 14%, and the mean relative oral bioavailability for Formulation #3 ranged from 10% to 21%.

FIG. 20 displays a comparison of azacitidine percent oral exposure as compared to SC azacitidine dosing (mean±SD) versus azacitidine dose (mg), following oral administration of Formation #3 or #6. Azacitidine oral dosage amounts included 180 mg, 240 mg, 300 mg, 360 mg, 480 mg, 600 mg, 720 mg, 900 mg, 1020 mg, 1080 mg, 1140 mg, and 1200 mg. At doses with n>1, the mean exposures of Formulation #6 and #3, as compared to SC, were similar.

G. Example 7

DNA methylation was employed as a biomarker to monitor responses in patients treated with azacitidine in the clinical studies described herein. Analysis was performed with an Infinium Assay (commercially available from Illumina, Inc., San Diego, Calif.). The Infinium Assay combined with BeadChips allows large-scale interrogation of variations in the human genome. For example, the Infinium HumanMethylation27 BeadChip enables interrogation of 27,578 CpG loci, covering over 14,000 genes. The DNA Methylation Assay protocol included the following steps: (1) bisulfite conversion; (2) DNA amplification; (3) DNA fragmentation; (4) DNA precipitation; (5) DNA hybridization to BeadChip; (6) extension and staining on BeadChip; and (7) imaging of BeadChip.

The assay for methylation was used to detect methylation status at individual CpG loci by typing bisulfite-converted DNA. Methylation protected C from conversion, whereas unmethylated C was converted to T. A pair of bead-bound probes was used to detect the presence of T or C by hybridization followed by single-base extension with a labeled nucleotide. Up to twelve samples were profiled in parallel. Blood and bone marrow samples were collected and DNA methylation was analyzed in parallel.

H. Example 8

A study is performed to examine whether baseline DNA and/or RNA methylation levels influence overall survival (OS) as well as the interaction between gene promotor methylation levels and treatment (e.g., azacitidine or conventional care regimens ("CCR")). Methylation is determined for 5 genes previously evaluated in MDS or AML: CDKN2B (p15), SOCS1, CDH1 (E-cadherin), TP73, and CTNNA1 (alpha-catenin), in pre-treatment bone marrow aspirates of patients enrolled in a clinical study using quantitative real-time methylation specific PCR (qMSP). The influence of methylation on OS is assessed using Cox proportional hazards models and Kaplan-Meier (KM) methodology.

The number of patients (e.g., for azacitidine and CCR) having nucleic acid sufficient for analysis of these 5 genes is determined. Methylation is detected in a specific percentage of patients for CDKN2B, SOCS1, CDH1, TP73, and CTNNA1. Differences in methylation levels between the treatment arms are determined. The OS benefit for cytidine analog (e.g., azacitidine) treatment is determined for patients who are positive and negative for methylation at these 5 genes. It is determined whether the presence of methylation is associated with improvement in OS in the CCR group (prognostic indicator of good outcome). The existence and magnitude of any effect is compared to the cytidine analog group, which may suggest an interaction between DNA and/or RNA methylation and treatment.

OS improvement is assessed with cytidine analog (e.g., azacitidine) treatment in patients with methylation at any of these 5 genes, and HR of death for methylation is determined. The frequency of methylation of particular genes allows for examination of the influence of methylation level on OS and treatment effect. For example, for particular genes, lower levels of methylation may be associated with the longest OS and the greatest OS benefit from cytidine analog treatment, compared with the absence of methylation. Influence of methylation level on OS may be assessed in each IPSS cytogenetic subgroup (good, intermediate, and poor). For example, the influence of methylation on OS may be strongest in the "poor" risk group, where risk of death is greatest.

Such data and analysis may indicate, e.g., that patients with lower levels of methylation may derive greater benefit from treatment with pharmaceutical compositions comprising a cytidine analog (e.g., azacitidine). Molecular biomarkers may be important in MDS, e.g., as indicators of disease prognosis and predictors of response to epigenetic therapy.

I. Example 9

Clinical studies are conducted to assess the ability of an oral formulation comprising a cytidine analog, such as 5-azacytidine, to treat patients having lung cancer, e.g., non-small-cell lung cancer (NSCLC). Such studies may include, e.g., an assessment of the ability to stop or reverse the growth of particular NSCLC cell types in patients having NSCLC). In certain clinical studies, patients are tested for particular NSCLC cell types, e.g., A549, H1975, H522, H23, H460, and H1299, prior to administration of the oral formulation. In certain clinical studies, patients with cell types known or believed to benefit preferentially from cytidine analog (e.g., 5-azacytidine) administration may be enrolled. In certain clinical studies, patients having NSCLC are enrolled without analysis of particular NSCLC cell type. In certain clinical studies, patients having any type of NSCLC cells are candidates for treatment with an oral formulation provided herein.

In certain clinical studies, patients from any of the three main NSCLC groups may be enrolled, i.e., (1) patients with tumors that are surgically resectable; (2) patients with either locally or regionally advanced lung cancer; or (3) patients with distant metastases at the time of diagnosis. In certain clinical studies, patients may be currently undergoing additional treatment for NSCLC, including, e.g., surgery, chemotherapy, or radiation therapy.

In certain clinical studies, patients who are administered an oral formulation comprising a cytidine analog (e.g., 5-azacytidine) may also be administered one or more additional therapeutic agents, examples of which are disclosed herein. The additional therapeutic agent(s) may be administered in the same oral formulation as the cytidine analog, or may be co-administered (e.g., via PO, SC or IV administration) in combination with an oral formulation comprising the cytidine analog. The appropriate amount and dosing schedule for an additional therapeutic agent is determined for a particular patient using methods known in the art.

An association between gene methylation and recurrence of NSCLC tumors is known in the art. See, e.g., M. V. Brock et al., *N. Engl. J. Med.*, 2008, 358(11):1118-28. Accordingly, in certain clinical studies provided herein, patients are screened prior to enrollment and/or monitored during the trial for DNA or RNA methylation levels, which indicate a potential response to treatment with an oral formulation comprising a cytidine analog (e.g., 5-azacytidine). In certain clinical studies, patients with high levels of DNA methylation (e.g., CpG island methylation) and/or an increased potential for transcriptional silencing of tumor-suppressor genes may be administered a cytidine analog (e.g., 5-azacytidine) known or believed to prevent or reverse hypermethylation (e.g., by reducing the activity of one or more DNA methyltransferase enzymes). In such studies, patients may also be co-administered one or more additional therapeutic agents known or believed to reduce epigenetic silencing, such as, e.g., compounds that inhibit histone deacetylase enzymes (HDACs), which regulate the acetylation and deacetylation of histone residues that increase or decrease gene expression. See, e.g., J. G. Herman & S. B. Baylin, *N. Engl. J. Med.*, 2003, 349:2042-54; P. A. Jones & S. B. Baylin, *Nature Rev. Gen.*, 2002, 3:415-28. Suitable HDAC inhibitors for co-administration in the clinical studies disclosed herein are known in the art and/or described herein (e.g., entinostat or vorinostat).

The amount of cytidine analog (e.g., 5-azacytidine) in the oral formulations administered during the clinical studies depends, e.g., on the individual characteristics of the patient, including, inter alia, the stage and progression of the patient's NSCLC, the patient's age and weight, the patient's prior treatment regimens, and other variables, as known in the art. In certain clinical studies, potential starting doses may be, e.g., about 60 mg, about 120 mg, about 180 mg, about 240 mg, about 300 mg, about 360 mg, about 420 mg, about 480 mg, about 540 mg, about 600 mg, about 660 mg, about 720 mg, about 780 mg, about 840 mg, about 900 mg, about 960 mg, about 1020 mg, or greater than about 1020 mg of the cytidine analog (e.g., 5-azacytidine) daily for a specified time period, e.g., about 1 week, about 1.5 weeks, about 2 weeks, about 2.5 weeks, about 3 weeks, about 3.5 weeks, about 1 month, about 1.5 months, about 2 months, or a longer time period. Other potential starting doses and time periods are disclosed herein. Cycles may be repeated as desired, e.g., over a period of one or more months, as disclosed herein. After a certain number of cycles, the dosage may be increased to increase the beneficial effect, provided such an increase will not cause undesirable toxicity effects. Patients may be treated for a minimum number of cycles, as disclosed herein. Complete or partial response may require additional treatment cycles. Treatment may be continued as long as the patient continues to benefit.

J. Example 10

Clinical studies are conducted to assess the ability of an oral formulation comprising a cytidine analog, such as 5-azacytidine, to treat patients having an ovarian cancer (including, e.g., the ability to stop or reverse the growth of cancer cells in patients having an ovarian cancer). Particular ovarian cancers include, but are not limited to, ovarian epithelial cancer, ovarian germ cell tumors, and ovarian low malignant potential tumors. In certain clinical studies, patients are screened for the presence of a particular type of ovarian cancer prior to administration of the oral formulation. In certain clinical studies, patients with a type of ovarian cancer known or believed to benefit preferentially from cytidine analog (e.g., 5-azacytidine) administration may be enrolled. In certain clinical studies, patients having ovarian cancer are enrolled without screening for particular ovarian cancer types. In certain clinical studies, patients having any type of ovarian cancer are candidates for treatment with an oral formulation provided herein. In certain clinical studies, patients may be currently undergoing additional treatment for ovarian cancer, including, e.g., surgery, chemotherapy, or radiation therapy.

In certain clinical studies, patients who are administered an oral formulation comprising a cytidine analog (e.g., 5-azacytidine) may also be administered one or more additional therapeutic agents, examples of which are disclosed herein (e.g., carboplatin). The additional therapeutic agent(s) may be administered in the same oral formulation as the cytidine analog, or may be co-administered (e.g., via PO, SC or IV administration) in combination with an oral formulation comprising a cytidine analog. The appropriate amount and dosing schedule for an additional therapeutic agent is determined for a particular patient using methods known in the art.

An association between gene methylation and ovarian cancer is known in the art. See, e.g., G. Gifford et al., *Clin. Cancer Res.*, 2004, 10:4420-26. Accordingly, in certain clinical studies provided herein, patients are screened prior to enrollment and/or monitored during the trial for DNA or RNA methylation levels, which indicate a potential response to treatment with an oral formulation comprising a cytidine analog (e.g., 5-azacytidine). In certain clinical studies, patients with high levels of DNA methylation (e.g., CpG island methylation) and/or an increased potential for transcriptional silencing of tumor-suppressor genes may be administered a cytidine analog (e.g., 5-azacytidine) known or believed to prevent or reverse hypermethylation (e.g., by reducing the activity of one or more DNA methyltransferase enzymes). In such studies, patients may also be co-administered one or more additional therapeutic agents known or believed to reduce epigenetic silencing, such as, e.g., compounds that inhibit histone deacetylase enzymes (HDACs), which regulate the acetylation and deacetylation of histone residues that increase or decrease gene expression. See, e.g., J. G. Herman & S. B. Baylin, *N. Engl. J. Med.*, 2003, 349:2042-54; P. A. Jones & S. B. Baylin, *Nature Rev. Gen.*, 2002, 3:415-28. Suitable HDAC inhibitors for co-administration in the clinical studies disclosed herein are known in the art and/or described herein (e.g., entinostat or vorinostat).

The amount of cytidine analog (e.g., 5-azacytidine) in the oral formulations administered during the clinical studies depends, e.g., on the individual characteristics of the patient, including, inter alia, the type, stage, and progression of the patient's ovarian cancer, the patient's age and weight, the patient's prior treatment regimens, and other variables, as known in the art. In certain clinical studies, potential starting doses may be, e.g., about 60 mg, about 120 mg, about 180 mg, about 240 mg, about 300 mg, about 360 mg, about 420 mg, about 480 mg, about 540 mg, about 600 mg, about 660 mg, about 720 mg, about 780 mg, about 840 mg, about 900 mg, about 960 mg, about 1020 mg, or greater than about 1020 mg of the cytidine analog (e.g., 5-azacytidine) daily for a specified time period, e.g., about 1 week, about 1.5 weeks, about 2 weeks, about 2.5 weeks, about 3 weeks, about 3.5 weeks, about 1 month, about 1.5 months, about 2 months, or a longer time period. Other potential starting doses and time periods are disclosed herein. Cycles may be repeated as desired, e.g., over a period of one or more months, as disclosed herein. After a certain number of cycles, the dosage may be increased to increase the beneficial effect, provided such an increase will not cause undesirable toxicity effects. Patients may be treated for a minimum number of cycles, as disclosed herein. Complete or partial response may require additional treatment cycles. Treatment may be continued as long as the patient continues to benefit.

K. Example 11

Clinical studies are conducted to assess the ability of an oral formulation comprising a cytidine analog, such as 5-azacytidine, to treat patients having a pancreatic cancer (including, e.g., the ability to stop or reverse the growth of cancer cells in patients having pancreatic cancer). In certain clinical studies, patients are screened prior to enrollment for a particular type of pancreatic cancer prior to administration of the oral formulation. Cellular classifications of pancreatic cancers are known in the art and include, e.g., duct cell carcinoma; acinar cell carcinoma; papillary mucinous carcinoma; signet ring carcinoma; adenosquamous carcinoma; undifferentiated carcinoma; mucinous carcinoma; giant cell carcinoma; mixed type (ductal-endocrine or acinar-endocrine); small cell carcinoma; cystadenocarcinoma (serous and mucinous types); unclassified; pancreatoblastoma; papillary-cystic neoplasm (Frantz tumor); invasive adenocarcinoma associated with cystic mucinous neoplasm or intraductal papillary mucinous neoplasm; mucinous cystic tumor with dysplasia; intraductal papillary mucinous tumor with dysplasia; and pseudopapillary solid tumor. In certain clinical studies, patients are screened prior to enrollment for a particular stage of pancreatic cancer (e.g., the size of the tumor in the pancreas, whether the cancer has spread, and if so, to what parts of the body) prior to administration of the oral formulation. In certain clinical studies, pancreatic cancer patients believed to benefit preferentially from cytidine analog (e.g., 5-azacytidine) administration may be enrolled. In certain clinical studies, patients having pancreatic cancer are enrolled without screening for particular pancreatic cancer types. In certain clinical studies, patients having any type of pancreatic cancer are candidates for treatment with an oral formulation provided herein. In certain clinical studies, patients may be currently undergoing additional treatment for pancreatic cancer, including, e.g., surgery, chemotherapy, or radiation therapy.

In certain clinical studies, patients who are administered an oral formulation comprising a cytidine analog (e.g., 5-azacytidine) may also be administered one or more additional therapeutic agents, examples of which are disclosed herein (e.g., gemcitabine). The additional therapeutic agent(s) may be administered in the same oral formulation as the cytidine analog, or may be co-administered (e.g., via PO, SC or IV administration) in combination with an oral formulation comprising a cytidine analog. The appropriate amount and dosing schedule for an additional therapeutic agent is determined for a particular patient using methods known in the art.

In certain clinical studies provided herein, patients are screened prior to enrollment and/or monitored during the trial for DNA or RNA methylation levels, which indicate a potential response to treatment with an oral formulation comprising a cytidine analog (e.g., 5-azacytidine). In certain clinical studies, patients with high levels of DNA methylation (e.g., CpG island methylation) and/or an increased potential for transcriptional silencing of tumor-suppressor genes may be administered a cytidine analog (e.g., 5-azacytidine) known or believed to prevent or reverse hypermethylation (e.g., by reducing the activity of one or more DNA methyltransferase enzymes). In such studies, patients may also be co-administered one or more additional therapeutic agents known or believed to reduce epigenetic silencing, such as, e.g., compounds that inhibit histone deacetylase enzymes (HDACs), which regulate the acetylation and deacetylation of histone residues that increase or decrease gene expression. See, e.g., J. G. Herman & S. B. Baylin, *N. Engl. J. Med.*, 2003, 349:2042-54; P. A. Jones & S. B. Baylin, *Nature Rev. Gen.*, 2002, 3:415-28. Suitable HDAC inhibitors for co-administration in the clinical studies disclosed herein are known in the art and/or described herein (e.g., entinostat or vorinostat).

The amount of cytidine analog (e.g., 5-azacytidine) in the oral formulations administered during the clinical studies depends, e.g., on the individual characteristics of the patient, including, inter alia, the type, stage, and progression of the patient's pancreatic cancer, the patient's age and weight, the patient's prior treatment regimens, and other variables, as known in the art. In certain clinical studies, potential starting doses may be, e.g., about 60 mg, about 120 mg, about 180 mg, about 240 mg, about 300 mg, about 360 mg, about 420 mg, about 480 mg, about 540 mg, about 600 mg, about 660 mg, about 720 mg, about 780 mg, about 840 mg, about 900 mg, about 960 mg, about 1020 mg, or greater than about 1020 mg of the cytidine analog (e.g., 5-azacytidine) daily for a specified time period, e.g., about 1 week, about 1.5 weeks, about 2 weeks, about 2.5 weeks, about 3 weeks, about 3.5 weeks, about 1 month, about 1.5 months, about 2 months, or a longer time period. Other potential starting doses and time periods are disclosed herein. Cycles may be repeated as desired, e.g., over a period of one or more months, as disclosed herein. After a certain number of cycles, the dosage may be increased to increase the beneficial effect, provided such an increase will not cause undesirable toxicity effects. Patients may be treated for a minimum number of cycles, as disclosed herein. Complete or partial response may require additional treatment cycles. Treatment may be continued as long as the patient continues to benefit.

L. Example 12

Clinical studies are conducted to assess the ability of an oral formulation comprising a cytidine analog, such as 5-azacytidine, to treat patients having a colorectal cancer (including, e.g., the ability to stop or reverse the growth of cancer cells in patients having a colorectal cancer). In certain clinical studies, patients are screened prior to enrollment for a particular type of colorectal cancer prior to administration of the oral formulation. Histologic types of colon cancers are known in the art and include, e.g., adenocarcinoma; muci-nous (colloid) adenocarcinoma; signet ring adenocarcinoma; scirrhous tumors; and neuroendocrine tumors. The World Health Organization classification of tumors of the colon and rectum include (1) Epithelial Tumors, which include: Adenoma (e.g., tubular, villous, tubulovillous, and serrated); Intraepithelial neoplasia (dysplasia) associated with chronic inflammatory diseases (e.g., low-grade glandular intraepithelial neoplasia and high-grade glandular intraepithelial neoplasia); Carcinoma (e.g., adenocarcinoma, mucinous adenocarcinoma, signet-ring cell carcinoma, small cell carcinoma, adenosquamous carcinoma, medullary carcinoma, and undifferentiated carcinoma); Carcinoid (well-differentiated neuroendocrine neoplasm) (e.g., enterochromaffin (EC)-cell, serotonin-producing neoplasm, L-cell, glucagon-like peptide and pancreatic polypeptide/peptide YY (PYY)-producing tumor, and others); and Mixed carcinoma-adenocarcinoma; and (2) Nonepithelial Tumors, which include: Lipoma; Leiomyoma; Gastrointestinal stromal tumor; Leiomyosarcoma; Angiosarcoma; Kaposi sarcoma; Melanoma; and others; as well as Malignant lymphomas (e.g., marginal zone B-cell lymphoma of mucosa-associated lymphoid tissue type, mantle cell lymphoma, diffuse large B-cell lymphoma, Burkitt lymphoma, and Burkitt-like/atypical Burkitt lymphoma. In certain clinical studies, patients are screened prior to enrollment for a particular stage of colorectal cancer (e.g., the size of the tumor in the colon or rectum, whether the cancer has spread, and if so, to what parts of the body) prior to administration of the oral formulation. In certain clinical studies, colorectal cancer patients believed to benefit preferentially from cytidine analog (e.g., 5-azacytidine) administration may be enrolled. In certain clinical studies, patients having a colorectal cancer are enrolled without screening for particular colorectal cancer types. In certain clinical studies, patients having any type of colorectal cancer are candidates for treatment with an oral formulation provided herein. In certain clinical studies, patients may be currently undergoing additional treatment for colorectal cancer, including, e.g., surgery, chemotherapy, or radiation therapy.

In certain clinical studies, patients who are administered an oral formulation comprising a cytidine analog (e.g., 5-azacytidine) may also be administered one or more additional therapeutic agents, examples of which are disclosed herein. The additional therapeutic agent(s) may be administered in the same oral formulation as the cytidine analog, or may be co-administered (e.g., via PO, SC or IV administration) in combination with an oral formulation comprising a cytidine analog. The appropriate amount and dosing schedule for an additional therapeutic agent is determined for a particular patient using methods known in the art.

An association between gene methylation and colorectal cancer is known in the art. See, e.g., A. M. Jubb et al., *J. Pathol.*, 2001, 195:111-134. Accordingly, in certain clinical studies provided herein, patients are screened prior to enrollment and/or monitored during the trial for DNA or RNA methylation levels, which indicate a potential response to treatment with an oral formulation comprising a cytidine analog (e.g., 5-azacytidine). In certain clinical studies, patients with high levels of DNA methylation (e.g., CpG island methylation) and/or an increased potential for transcriptional silencing of tumor-suppressor genes may be administered a cytidine analog (e.g., 5-azacytidine) known or believed to prevent or reverse hypermethylation (e.g., by reducing the activity of one or more DNA methyltransferase enzymes). In such studies, patients may also be co-administered one or more additional therapeutic agents known or believed to reduce epigenetic silencing, such as, e.g., compounds that inhibit histone deacetylase enzymes (HDACs), which regulate the acetylation and deacetylation of histone residues that increase or decrease gene expression. See, e.g., J. G. Herman & S. B. Baylin, *N. Engl. J. Med.*, 2003, 349:2042-54; P. A. Jones & S. B. Baylin, *Nature Rev. Gen.*, 2002, 3:415-28. Suitable HDAC inhibitors for co-administration in the clinical studies disclosed herein are known in the art and/or described herein (e.g., entinostat or vorinostat).

The amount of cytidine analog (e.g., 5-azacytidine) in the oral formulations administered during the clinical studies depends, e.g., on the individual characteristics of the patient, including, inter alia, the type, stage, and progression of the patient's colorectal cancer, the patient's age and weight, the patient's prior treatment regimens, and other variables, as known in the art. In certain clinical studies, potential starting doses may be, e.g., about 60 mg, about 120 mg, about 180 mg, about 240 mg, about 300 mg, about 360 mg, about 420 mg, about 480 mg, about 540 mg, about 600 mg, about 660 mg, about 720 mg, about 780 mg, about 840 mg, about 900 mg, about 960 mg, about 1020 mg, or greater than about 1020 mg of the cytidine analog (e.g., 5-azacytidine) daily for a specified time period, e.g., about 1 week, about 1.5 weeks, about 2 weeks, about 2.5 weeks, about 3 weeks, about 3.5 weeks, about 1 month, about 1.5 months, about 2 months, or a longer time period. Other potential starting doses and time periods are disclosed herein. After a certain number of cycles, the dosage may be increased to increase the beneficial effect, provided such an increase will not cause undesirable toxicity effects. Patients may be treated for a minimum number of cycles, as disclosed herein. Complete or partial response may require additional treatment cycles. Treatment may be continued as long as the patient continues to benefit.

The present disclosure has been described in connection with certain embodiments and examples; however, unless otherwise indicated, the claimed invention should not be unduly limited to such specific embodiments and examples.

What is claimed is:

1. A pharmaceutical composition for oral administration comprising 180 mg to 360 mg of 5-azacytidine and at least one pharmaceutically acceptable excipient, wherein the composition is a non-enteric coated tablet, and wherein a therapeutically effective amount of 5-azacytidine is not absorbed through oral mucosa upon administration to a human subject.

2. The composition of claim 1, wherein the tablet is an immediate release tablet.

3. The composition of claim 2, wherein the amount of 5-azacytidine is 300 mg.

4. The composition of claim 2, wherein the amount of 5-azacytidine is 200 mg.

5. The composition of claim 1, wherein the tablet does not comprise a methacrylic acid copolymer.

6. The composition of claim 5, wherein the amount of 5-azacytidine is 300 mg.

7. The composition of claim 5, wherein the amount of 5-azacytidine is 200 mg.

8. The composition of claim 2, wherein the tablet does not comprise a methacrylic acid copolymer.

9. The composition of claim 8, wherein the amount of 5-azacytidine is 300 mg.

10. The composition of claim 8, wherein the amount of 5-azacytidine is 200 mg.

11. The composition of claim 1, wherein the tablet does not comprise triethyl citrate.

12. The composition of claim 2, wherein the tablet does not comprise triethyl citrate.

13. The composition of claim 3, wherein the tablet does not comprise triethyl citrate.

14. The composition of claim 4, wherein the tablet does not comprise triethyl citrate.

15. The composition of claim 1, wherein the tablet does not comprise polymethacrylate.

16. The composition of claim 2, wherein the tablet does not comprise polymethacrylate.

17. The composition of claim 3, wherein the tablet does not comprise polymethacrylate.

18. The composition of claim 4, wherein the tablet does not comprise polymethacrylate.

19. The composition of claim 1, wherein the tablet comprises a non-enteric coating comprising hydroxypropyl methyl cellulose.

20. The composition of claim 2, wherein the tablet comprises a non-enteric coating comprising hydroxypropyl methyl cellulose.

21. The composition of claim 3, wherein the tablet comprises a non-enteric coating comprising hydroxypropyl methyl cellulose.

22. The composition of claim 4, wherein the tablet comprises a non-enteric coating comprising hydroxypropyl methyl cellulose.

* * * * *